United States Patent
Coe et al.

(10) Patent No.: US 9,540,383 B2
(45) Date of Patent: Jan. 10, 2017

(54) PYRROLOPYRIMIDINES AS THERAPEUTIC AGENTS FOR THE TREATMENT OF DISEASES

(71) Applicant: GlaxoSmithKline LLC, Wilmington, DE (US)

(72) Inventors: Diane Mary Coe, Stevenage (GB); Stephen Allan Smith, Stevenage (GB)

(73) Assignee: GlaxoSmithKline LLC, Wilmington, DE (US)

(*) Notice: Subject to any disclaimer, the term of this patent is extended or adjusted under 35 U.S.C. 154(b) by 0 days.

(21) Appl. No.: 14/443,932

(22) PCT Filed: Nov. 18, 2013

(86) PCT No.: PCT/US2013/070472
§ 371 (c)(1),
(2) Date: May 19, 2015

(87) PCT Pub. No.: WO2014/081645
PCT Pub. Date: May 30, 2014

(65) Prior Publication Data
US 2015/0284396 A1    Oct. 8, 2015

Related U.S. Application Data

(60) Provisional application No. 61/774,087, filed on Mar. 7, 2013, provisional application No. 61/728,390, filed on Nov. 20, 2012.

(51) Int. Cl.
*A61K 31/519* (2006.01)
*C07D 487/04* (2006.01)
*A61K 39/00* (2006.01)

(52) U.S. Cl.
CPC ............. *C07D 487/04* (2013.01); *A61K 39/00* (2013.01)

(58) Field of Classification Search
CPC .................................................. C07D 487/04
See application file for complete search history.

(56) References Cited

U.S. PATENT DOCUMENTS

| | | | |
|---|---|---|---|
| 5,962,479 A | 10/1999 | Chen | |
| 6,376,501 B1 | 4/2002 | Isobe et al. | |
| 6,552,192 B1 | 4/2003 | Hanuset et al. | |
| 7,125,880 B1 | 10/2006 | Chen | |
| 7,390,890 B2 | 6/2008 | Furneaux et al. | |
| 7,642,350 B2 | 1/2010 | Pryde | |
| 7,977,344 B2 | 7/2011 | Lazarides et al. | |
| 8,067,413 B2 | 11/2011 | Bonnert et al. | |
| 8,067,426 B2 | 11/2011 | Biggadike et al. | |
| 8,563,717 B2 | 10/2013 | Bazin-Lee et al. | |
| 8,575,181 B2 | 11/2013 | Campos et al. | |
| 8,575,340 B2 | 11/2013 | Bazin-Lee et al. | |
| 8,703,754 B2 | 4/2014 | Gibbon et al. | |
| 8,765,772 B2 | 7/2014 | Biggadike et al. | |
| 8,802,684 B2 | 8/2014 | Bazin-Lee et al. | |
| 9,173,872 B2 | 11/2015 | Coe et al. | |
| 2001/0020030 A1 | 9/2001 | Stewart et al. | |
| 2002/0037886 A1 | 3/2002 | Andersson et al. | |
| 2003/0187261 A1 | 10/2003 | Havlicek et al. | |
| 2003/0191086 A1 | 10/2003 | Hanus et al. | |
| 2003/0220365 A1 | 11/2003 | Stewart et al. | |

(Continued)

FOREIGN PATENT DOCUMENTS

| | | | |
|---|---|---|---|
| EP | 0773023 A1 | 5/1997 | |
| EP | 1043021 A1 | 7/1999 | |

(Continued)

OTHER PUBLICATIONS

U.S. Appl. No. 14/443,903 (Coe et al.) filed May 19, 2015.
U.S. Appl. No. 14/443,924 (Coe et al.) filed May 19, 2015.
Akira, S., Toll-like receptors: critical proteins linking innate and acquired immunity. Nat. Immuno. 2001; 2(8); 675-680.
Allergic Rhinitis-Prevention (http://www.webmd.com/allergies/tc/allergic-rhinitis-prevention); WebMD: Allergic Health Center; Jun. 30, 2011.
Asthma Prevention (http://www.webmd.com/asthma/guide/asthma-prevention); WebMD: Asthma Health Center; May 13, 2012.

(Continued)

*Primary Examiner* — Brian McDowell
(74) *Attorney, Agent, or Firm* — Leah M. Octavio; Andrea V. Lockenour

(57) ABSTRACT

Compounds of formula (I) and salts thereof:

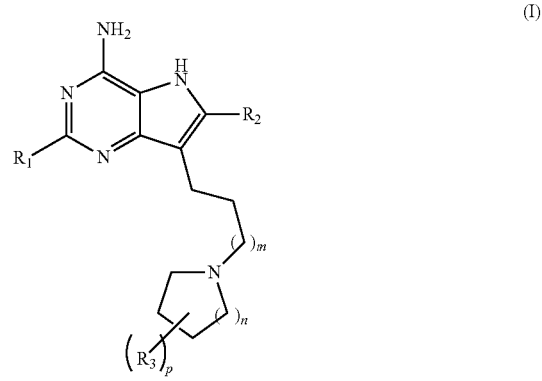

wherein $R_1$ is n-$C_{4-6}$alkyl or $C_{1-2}$alkoxy$C_{1-2}$alkyl-; $R_2$ is hydrogen or methyl; each $R_3$ is hydroxy, halo or n-$C_{1-3}$alkyl; m is an integer having a value of 2 to 4; n is an integer having a value of 0 to 3; and p is an integer having a value of 0 to 2, are inducers of human interferon. Compounds which induce human interferon may be useful in the treatment of various disorders, for example the treatment of allergic diseases and other inflammatory conditions, for example allergic rhinitis and asthma, infectious diseases and cancer, and may also be useful as vaccine adjuvants.

18 Claims, No Drawings

(56) References Cited

U.S. PATENT DOCUMENTS

| | | |
|---|---|---|
| 2003/0236216 A1 | 12/2003 | Devos et al. |
| 2004/0063658 A1 | 4/2004 | Roberts et al. |
| 2005/0054590 A1 | 3/2005 | Averett |
| 2006/0029642 A1 | 2/2006 | Miljkovic et al. |
| 2006/0052403 A1 | 3/2006 | Isobe et al. |
| 2006/0148805 A1 | 7/2006 | Chen et al. |
| 2006/0264448 A1 | 11/2006 | Pryde |
| 2007/0190071 A1 | 8/2007 | Kurimoto et al. |
| 2007/0197478 A1 | 8/2007 | Jones et al. |
| 2007/0225303 A1 | 9/2007 | Ogita et al. |
| 2007/0275984 A1 | 11/2007 | Imogai et al. |
| 2008/0008682 A1 | 1/2008 | Chong et al. |
| 2008/0269240 A1 | 10/2008 | Hashimoto et al. |
| 2008/0300244 A1 | 12/2008 | Bonnert et al. |
| 2009/0047249 A1 | 2/2009 | Graupe et al. |
| 2009/0082332 A1 | 3/2009 | Abbot et al. |
| 2009/0099216 A1 | 4/2009 | Millichip et al. |
| 2009/0105212 A1 | 4/2009 | Isobe et al. |
| 2009/0118263 A1 | 5/2009 | Hashimoto et al. |
| 2009/0131458 A1 | 5/2009 | Lazarides et al. |
| 2009/0143400 A1 | 6/2009 | McInally et al. |
| 2009/0192153 A1 | 7/2009 | Hashimoto et al. |
| 2009/0202484 A1 | 8/2009 | Chong et al. |
| 2009/0233948 A1 | 9/2009 | Evans et al. |
| 2009/0324551 A1 | 12/2009 | Carson et al. |
| 2009/0325877 A1 | 12/2009 | Grunt et al. |
| 2010/0010016 A1 | 1/2010 | Gangjee |
| 2010/0075995 A1 | 3/2010 | Biggadike et al. |
| 2010/0087443 A1 | 4/2010 | Bonnert et al. |
| 2010/0093998 A1 | 4/2010 | Isobe et al. |
| 2010/0099870 A1 | 4/2010 | Isobe et al. |
| 2010/0120799 A1 | 5/2010 | Lazarides et al. |
| 2010/0130491 A1 | 5/2010 | Bonnert et al. |
| 2010/0240623 A1 | 9/2010 | Cook et al. |
| 2011/0135671 A1 | 6/2011 | Bazin-Lee et al. |
| 2011/0229500 A1 | 9/2011 | Biggadike et al. |
| 2011/0269781 A1 | 11/2011 | Lazarides et al. |
| 2012/0035193 A1 | 2/2012 | Biggadike et al. |
| 2012/0135963 A1 | 5/2012 | Johnson |
| 2012/0171229 A1 | 7/2012 | Zepp et al. |
| 2012/0264768 A1 | 10/2012 | Gangee |
| 2012/0283438 A1 | 11/2012 | Lazarides et al. |
| 2012/0315291 A1 | 12/2012 | Bazin-Lee et al. |
| 2014/0056928 A1 | 2/2014 | Coe et al. |
| 2014/0288099 A1 | 9/2014 | Ambery et al. |
| 2014/0336175 A1 | 11/2014 | Biggaike et al. |
| 2015/0225403 A1 | 8/2015 | Coe et al. |

FOREIGN PATENT DOCUMENTS

| | | |
|---|---|---|
| EP | 1348707 A1 | 10/2003 |
| EP | 1939198 A1 | 3/2007 |
| EP | 1939199 A1 | 7/2008 |
| EP | 2138497 A1 | 12/2009 |
| RU | 2221799 C2 | 1/2004 |
| WO | 9533750 A1 | 12/1995 |
| WO | WO-9749706 A1 | 12/1997 |
| WO | WO-99/40091 A1 | 8/1999 |
| WO | WO-00/43394 A1 | 7/2000 |
| WO | 0149688 A1 | 7/2001 |
| WO | 0183472 A1 | 11/2001 |
| WO | WO-03/053970 A1 | 7/2003 |
| WO | 2004018496 A1 | 3/2004 |
| WO | 2004029054 A1 | 4/2004 |
| WO | 2005002520 A2 | 1/2005 |
| WO | 2011017611 A1 | 2/2005 |
| WO | 2005020892 A2 | 3/2005 |
| WO | 2005025583 A2 | 3/2005 |
| WO | 2005079195 A2 | 9/2005 |
| WO | 2005097800 A1 | 10/2005 |
| WO | WO-2005/110410 A2 | 11/2005 |
| WO | WO-2006/030031 A1 | 3/2006 |
| WO | 2006117670 A1 | 11/2006 |
| WO | 2007013964 A1 | 2/2007 |
| WO | 2007028129 A1 | 3/2007 |
| WO | 2007034881 A1 | 3/2007 |
| WO | WO-2007/024944 A1 | 3/2007 |
| WO | 2007041863 A1 | 4/2007 |
| WO | 2007093901 A1 | 8/2007 |
| WO | 2007110868 A1 | 10/2007 |
| WO | 2007138084 A1 | 12/2007 |
| WO | 2007142755 A2 | 12/2007 |
| WO | 2008004948 A1 | 1/2008 |
| WO | 2008101867 A1 | 8/2008 |
| WO | WO-2008/100457 A2 | 8/2008 |
| WO | 2008114008 A1 | 9/2008 |
| WO | WO-2008/154221 A2 | 12/2008 |
| WO | 2009019505 A1 | 2/2009 |
| WO | WO-2009/023179 A2 | 2/2009 |
| WO | 2009078798 A1 | 6/2009 |
| WO | WO-2010/006025 A1 | 1/2010 |
| WO | 2010013132 A1 | 2/2010 |
| WO | 2010018130 A1 | 2/2010 |
| WO | 2010018131 A1 | 2/2010 |
| WO | 2010018133 A1 | 2/2010 |
| WO | 2010018134 A1 | 2/2010 |
| WO | WO-2010/083725 A1 | 7/2010 |
| WO | 2011098451 A1 | 8/2011 |
| WO | 2011098452 A1 | 8/2011 |
| WO | 2012009258 A2 | 1/2012 |
| WO | 2012106343 A2 | 8/2012 |
| WO | 2014081643 A1 | 5/2014 |
| WO | 2014081644 A1 | 5/2014 |
| WO | 2014081645 A1 | 5/2014 |
| WO | 2015124591 A1 | 8/2015 |

OTHER PUBLICATIONS

Berge, S.M., et al. J. Pharmaceutical Science, Published 1977, vol. 66, pp. 1-19.

Borden E.C., et al., Interferons at age 50: past, current and future impact on biomedicine, Nat Rev Drug Discov., Dec. 2007, 6(12), 975-990.

Czarniecki, M. Small Molecule Modulators of Toll-like Receptors, Nov. 13, 2008, vol. 51(21), 6621-6626.

Corren, J., et al.; A Randomized, Controlled, Phase 2 Study of AMG 317, an IL-4Rα Antagonist, in Patients with Asthma; Am. J. Respir. Crit. Care Med.; 2010; vol. 181; pp. 788-796.

Cryz, S.J. et al.; Immunotherapy and Vaccines; Ullmann's Encyclopedia of Industrial Chemistry; 2000; vol. 18; pp. 647-722.

Dermer, G.B. Another. Anniversary for the War on Cancer. Bio/Technology, 1994, 12, 320.

Freshney, R,I., et al., "Culture of Animal Cells." A Manual of Basic Technique, Alan R. Liss, Inc., 1983, New York, 1-7.

Flood-Page, P. et al.; A Study to Evaluate Safety and Efficacy of Mepolizumab in Patients with Moderate Persistent Asthma; Am. J. Respir. Crit. Care Med.; Dec. 1, 2007; vol. 176, No. 11; pp. 1062-1071.

Gautschi, O., et al. "Aurora Kinases as Anticancer Drug Targets." Clin Cancer Res., Mar. 15, 2008, 14(6), 1639-1648.

Gauvreau, G.M. et al.; Effects of Interleukin-13 Blockade on Allergen-induced Airway Responses in Mild Atopic Asthma; Am. J. Respir. Crit. Care Med.; Nov. 5, 2010; doi:1 0.1164/rccm.201 008-121 OOC.

Golub, T.R., et al. "Molecular Classification of Cancer: Class Discovery and Class Prediction by Gene Expression Monitoring." Science, Oct. 15, 1999, 286, 531-537.

Gould P.L.; Salt Selection for Basic Drugs; International Journal of Pharmaceutics; 1986; 33; 201-217.

Haldar, P., et al., Mepolizumab and Exacerbations of Refractory Eosinophilic Asthma; The New England Journal of Medicine; 2009; vol. 360(10); pp. 973-984.

Hirota, K., et al.; "Discovery of 8-Hydroxyadenines as a Novel Type of Interferon Inducer"; J. Med. Chem.; 2002; vol. 45, No. 25; pp. 5419-5422; American Chemical Society.

Huber, J.P. et al.; Cutting Edge: Type I IFN Reverses Human Th2 Commitment and Stability by Suppressing GATA3; The Journal of Immunology; 2010; vol. 185; pp. 813-817.

Hussein, W.M., et al. Toll-like receptor agonists: a patent review (2011-2013); Expert Opinion on Therapeutic Patents, Jan. 24, 2014, pp. 1-18.

(56) References Cited

OTHER PUBLICATIONS

Isobe, Y., et al.; Synthesis and Biological Evaluation of Novel 9-Substituted-8-hydroxyadenrine Derivatives as Potent Interferon Inducers; J. Med. Chem.; 2006; vol. 49, No. 6; pp. 2088-2095; American Chemical Society.

Kariyawasam, H.H., Et al.; Effects of Anti-IL-13 (Novartis QAX576) on Inflammatory Responses Following Nasal Allergen Challenge (NAC); Am. J. Respir. Crit. Care Med.; 2009; vol. 179; A3642.

Kurimoto, A., et al.; Prodrugs of 9-Benzyl-8-hydroxy-2-(2-hydroxyethylthio)adenine: Potent Interferon Inducing Agents in Monkeys; Chem. Pharm. Bull.; 2004; vol. 52, No. 4; pp. 466-469; Pharmaceutical Society of Japan.

Liu, Y-J., IPC: Profesional Type 1 Interferon-Producing Cells and Plasmacytoid Dendridic Cell Precursors, Ann. Rev. Immunol., 2005; 23:275-306.

Ma, R., Additive effects of CpG ODN and R-848 as adjuvants on augmenting immune responses to HBsAg vaccination, Biochem. Biophys., Res. Commun., 2007; 361:537-542.

McMahon G., et al. VEGF Receptor Signaling in Tumor Angiogenesis, The Oncologist, 2000, 5(Suppl1), pp. 3-10.

Mountzios, G., et al. "Aurora kinases as targets for cancer therapy." Cancer Treatment Reviews, 2008, 34, 175-182.

Pinedo, H.M., et al. Translational Research: The Role of VEGH in Tumor Angiogenesis. The Oncologist, 2000, 5 (Suppl1), pp. 1-2.

Pyne, S., et al. "Spingosine Kinase Inhibitors and Cancer: Seeking the Golden Sword of Hercules." Cancer Research, 2011, 71, 6576-6582.

Roemer, T., et al. "Auxiliary factors: a chink in the armor of MRSA resistance to β-lactam antibiotics." Current Opinion in Microbiology, 2013, 16, 538-548.

Simon, H-U., et al,; Clinical and immunological effects of low-dose IFN-α treatment in patients with corticosteroid-resistant asthma; Allergy; 2003; vol. 58; pp. 1250-1255.

Simone, J.V. Cecil Textbook of Medicine, edited by Bennet J.C. and Plum F., 20th edition, vol. 1, 1996, 1004-1010.

Snyder, J.W., et al. "Common bacteria whose susceptibility to antimicrobials is no longer predictable." J. Med. Liban, Pub Med Abstract, 2000, 48(4), 208-214.

Sugar, A.M. et al. "Comparson of Three Methods of Antifungal Susceptibilty Testing wth the Proposed NCCLS Standard Broth Microdilution Assay: Lack of Phenol Red." Diagno Microbiol Infect Dis, 1995, 21, 129-133.

Swarbrick, J., et al. Encyclopedia of Pharmaceutical Technology, Published 1996, vol. 13, pp. 453-499.

Tao, B., Treatment of allergic airway inflammation arid hyper-responsiveness by imiquimod modulating transcription factors T-bet and GATA-3, Chin. Med. J. 2006; 119(8): 640-648.

Turner W. et al. "Recent Advances in the Medicinal Chemisty of Antifungal Agents." Current Pharmaceutical Design, 1996, 2, 209-224.

Leaker, et al., *Am. J. Respir. Grit, Care Med.*, "The Effects of The Novel Toll-Like Receptor 7 (TLR7) Agonist AZD 88.48 On Allergen-Induced Responses in Patients With Mild Asthma," 185:A4184 (2012).

PYRROLOPYRIMIDINES AS THERAPEUTIC AGENTS FOR THE TREATMENT OF DISEASES

This application is filed pursuant to 35 U.S.C. §371 as a United States National Phase Application of International Patent Application No. PCT/US2013/070472 filed Nov. 18, 2013, which claims priority from Provisional Application No. 61/774,087 filed Mar. 7, 2013 and from Provisional Application No. 61/728,390 filed Nov. 20, 2012.

TECHNICAL FIELD OF THE INVENTION

The present invention relates to compounds, processes for their preparation, compositions containing them, to their use in the treatment of various disorders in particular allergic diseases and other inflammatory conditions for example allergic rhinitis and asthma, infectious diseases, and cancer, and as vaccine adjuvants.

BACKGROUND OF THE INVENTION

Vertebrates are constantly threatened by the invasion of microorganisms and have evolved mechanisms of immune defence to eliminate infective pathogens. In mammals, this immune system comprises two branches; innate immunity and acquired immunity. The first line of host defence is the innate immune system, which is mediated by macrophages and dendritic cells. Acquired immunity involves the elimination of pathogens at the late stages of infection and also enables the generation of immunological memory. Acquired immunity is highly specific, due to the vast repertoire of lymphocytes with antigen-specific receptors that have undergone gene rearrangement.

Central to the generation of an effective innate immune response in mammals are mechanisms which bring about the induction of interferons and other cytokines which act upon cells to induce a number of effects. In man, the type I interferons are a family of related proteins encoded by genes on chromosome 9 and encoding at least 13 isoforms of interferon alpha (IFNα) and one isoform of interferon beta (IFNβ). Interferon was first described as a substance which could protect cells from viral infection (Isaacs & Lindemann, *J. Virus Interference. Proc. R. Soc. Lon. Ser. B. Biol. Sci.* 1957: 147, 258-267). Recombinant IFNα was the first approved biological therapeutic and has become an important therapy in viral infections and in cancer. As well as direct antiviral activity on cells, interferons are known to be potent modulators of the immune response, acting on cells of the immune system (Gonzalez-Navajas J. M. et al *Nature Reviews Immunology,* 2012; 2, 125-35).

Toll-like receptors (TLRs) are a family of ten Pattern Recognition Receptors described in man (Gay, N. J. et al, *Annu. Rev. Biochem.,* 2007: 46, 141-165). TLRs are expressed predominantly by innate immune cells where their role is to monitor the environment for signs of infection and, on activation, mobilise defence mechanisms aimed at the elimination of invading pathogens. The early innate immune-responses triggered by TLRs limit the spread of infection, while the pro-inflammatory cytokines and chemokines that they induce lead to recruitment and activation of antigen presenting cells, B cells, and T cells. The TLRs can modulate the nature of the adaptive immune-responses to give appropriate protection via dendritic cell-activation and cytokine release (Akira S. et al, *Nat. Immunol.,* 2001: 2, 675-680). The profile of the response seen from different TLR agonists depends on the cell type activated.

TLR7 is a member of the subgroup of TLRs (TLRs 3, 7, 8, and 9), localised in the endosomal compartment of cells which have become specialised to detect non-self nucleic acids. TLR7 plays a key role in anti-viral defence via the recognition of ssRNA (Diebold S. S. et al, *Science,* 2004: 303, 1529-1531; and Lund J. M. et al, PNAS, 2004: 101, 5598-5603). TLR7 has a restricted expression-profile in man and is expressed predominantly by B cells and plasmacytoid dendritic cells (pDC), and to a lesser extent by monocytes. Plasmacytoid DCs are a unique population of lymphoid-derived dendritic cells (0.2-0.8% of Peripheral Blood Mononuclear Cells (PBMCs)) which are the primary type I interferon-producing cells secreting high levels of interferon-alpha (IFNα) and interferon-beta (IFNβ) in response to viral infections (Liu Y-J, *Annu. Rev. Immuno.,* 2005: 23, 275-306).

Administration of a small molecule compound which could stimulate the innate immune response, including the activation of type I interferons and other cytokines via Toll-like receptors, could become an important strategy for the treatment or prevention of human diseases. Small molecule agonists of TLR7 have been described which can induce interferon alpha in animals and in man (Takeda K et al, *Annu. Rev. Immuno.,* 2003: 21, 335-76). TLR7 agonists include imidazoquinoline compounds such as imiquimod and resiquimod, oxoadenine analogues and also nucleoside analogues such as loxoribine and 7-thia-8-oxoguanosine which have long been known to induce interferon alpha (Czarniecki. M., *J. Med, Chem.,* 2008: 51, 6621-6626; Hedayat M. et al, *Medicinal Research Reviews,* 2012: 32, 294-325). This type of immunomodulatory strategy has the potential to identify compounds which may be useful in the treatment of allergic diseases (Moisan J. et al, *Am. J. Physiol. Lung Cell Mol. Physio.,* 2006: 290, L987-995), viral infections (Horcroft N. J. et al, *J. Antimicrob. Chemther,* 2012: 67, 789-801), cancer (Krieg A., *Curr. Oncol. Rep.,* 2004: 6(2), 88-95), other inflammatory conditions such as irritable bowel disease (Rakoff-Nahoum S., *Cell.,* 2004, 23, 118(2): 229-41), and as vaccine adjuvants (Persing et al. *Trends Microbiol.* 2002: 10 (10 Suppl), S32-7). More specifically, allergic diseases are associated with a Th2-biased immune-response to allergens. Th2 responses are associated with raised levels of IgE, which, via its effects on mast cells, promotes a hypersensitivity to allergens, resulting in the symptoms seen, for example, in asthma and allergic rhinitis. In healthy individuals the immune-response to allergens is more balanced with a mixed Th2/Th1 and regulatory T cell response. TLR7 ligands have been shown to reduce Th2 cytokine and enhance Th1 cytokine release in vitro and to ameliorate Th2-type inflammatory responses in allergic lung models in vivo (Duechs M. J., *Pulmonary Pharmacology & Therapeutics,* 2011: 24, 203-214; Fili L. et al, *J. All. Clin. Immuno.,* 2006: 118, 511-517; Tao et al, Chin. Med. 1, 2006: 119, 640-648; Van L. P. *Eur. J. Immuno.,* 2011: 41, 1992-1999). Thus TLR7 ligands have the potential to rebalance the immune-response seen in allergic individuals and lead to disease modification. Recent clinical studies with the TLR7 agonist have shown repeated intranasal stimulation of TLR7 to produce a sustained reduction in the responsiveness to allergen in patients with both allergic rhinitis and allergic asthma (Greiff L. *Respiratory Research,* 2012: 13, 53; Leaker B. R. et al, *Am. J. Respir. Crit. Care Med.,* 2012: 185, A4184).

In the search for novel small molecule inducers of human interferon IFNα an assay strategy has been developed to characterise small molecule (regardless of mechanism) which is based on stimulation of primary human donor cells or whole blood with compounds, and is disclosed herein.

SUMMARY OF THE INVENTION

In a first aspect, the present invention is directed to compounds of formula (I) and salts thereof:

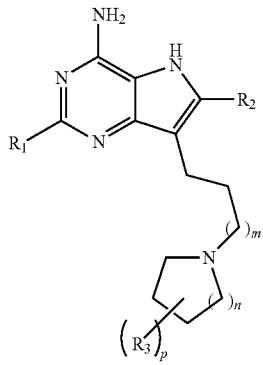

(I)

wherein:
$R_1$ is n-$C_{4-6}$alkyl or $C_{1-2}$alkoxy$C_{1-2}$alkyl-;
$R_2$ is hydrogen or methyl;
each $R_3$ is hydroxy, halo or n-$C_{1-3}$alkyl;
m is an integer having a value of 2 to 4;
n is an integer having a value of 0 to 3;
p is an integer having a value of 0 to 2.

Certain compounds of the invention have been shown to be inducers of human interferon and may possess a desirable developability profile compared to known inducers of human interferon. In addition, certain compounds of the invention may show selectivity for IFNα with respect to TNFα. Compounds which induce human interferon may be useful in the treatment of various disorders, for example the treatment of allergic diseases and other inflammatory conditions, for example allergic rhinitis and asthma, the treatment of infectious diseases and cancer. Accordingly, the invention is further directed to pharmaceutical compositions comprising a compound of formula (I), or a pharmaceutically acceptable salt thereof. The present invention is further directed to methods of treatments of disorders associated therewith using a compound of formula (I) or a pharmaceutically acceptable salt thereof, or a pharmaceutical composition comprising a compound of formula (I) or a pharmaceutically acceptable salt thereof.

The compounds of the invention may also have use as vaccine adjuvants. Consequently, the present invention is further directed to a vaccine composition comprising a compound of formula (I), or a pharmaceutically acceptable salt thereof, and an antigen or antigen composition.

Certain compounds of the invention are potent immunomodulators and accordingly, care should be exercised in their handling.

DETAILED DESCRIPTION OF THE INVENTION

In a first aspect, the present invention is directed to compounds of formula (I) and salts thereof:

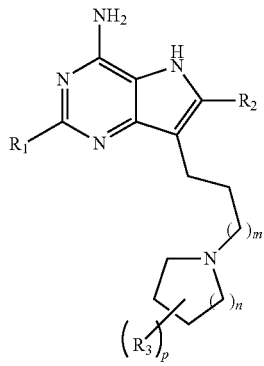

(I)

wherein:
$R_1$ is n-$C_{4-6}$alkyl or $C_{1-2}$alkoxy$C_{1-2}$alkyl-;
$R_2$ is hydrogen or methyl;
each $R_3$ is hydroxy, halo or n-$C_{1-3}$alkyl;
m is an integer having a value of 2 to 4;
n is an integer having a value of 0 to 3;
p is an integer having a value of 0 to 2.

In a further aspect, $R_1$ is n-butyl.
In a further aspect, $R_1$ is ethoxymethyl.
In a further aspect, $R_1$ is 2-methoxyethyl.
In a further aspect, $R_2$ is hydrogen.
In a further aspect, $R_2$ is methyl.
In a further aspect, m is an integer having a value of 2, 3 or 4.
In a further aspect, n is an integer having a value of 1 or 2.
In a further aspect, p is 0.
In a further aspect, $R_3$ is hydroxy or halo.
In a further aspect, p is 1 and $R_3$ is hydroxy or fluoro.
In a further aspect, p is 2 and $R_3$ is fluoro.

Examples of compounds of formula (I) are provided in the following group, and form a further aspect of the invention:
2-Butyl-7-(6-(piperidin-1-yl)hexyl)-5H-pyrrolo[3,2-d]pyrimidin-4-amine;
2-Butyl-7-(5-(piperidin-1-yl)pentyl)-5H-pyrrolo[3,2-d]pyrimidin-4-amine;
2-Butyl-7-(4-(piperidin-1-yl)butyl)-5H-pyrrolo[3,2-d]pyrimidin-4-amine;
2-(Ethoxymethyl)-7-(6-(piperidin-1-yl)hexyl)-5H-pyrrolo[3,2-d]pyrimidin-4-amine;
2-(2-Methoxyethyl)-7-(6-(piperidin-1-yl)hexyl)-5H-pyrrolo[3,2-d]pyrimidin-4-amine;
2-Butyl-6-methyl-7-(6-(piperidin-1-yl)hexyl)-5H-pyrrolo[3,2-d]pyrimidin-4-amine;
2-Butyl-6-methyl-7-(5-(piperidin-1-yl)pentyl)-5H-pyrrolo[3,2-d]pyrimidin-4-amine;
2-Butyl-6-methyl-7-(4-(piperidin-1-yl)butyl)-5H-pyrrolo[3,2-d]pyrimidin-4-amine;
2-Butyl-7-(5-(pyrrolidin-1-yl)pentyl)-5H-pyrrolo[3,2-d]pyrimidin-4-amine;
2-Butyl-7-(6-(pyrrolidin-1-yl)hexyl)-5H-pyrrolo[3,2-d]pyrimidin-4-amine;
2-Pentyl-7-(6-(piperidin-1-yl)hexyl)-5H-pyrrolo[3,2-d]pyrimidin-4-amine;
7-(5-(Azepan-1-yl)pentyl)-2-butyl-5H-pyrrolo[3,2-d]pyrimidin-4-amine;
7-(4-(Azepan-1-yl)butyl)-2-butyl-6-methyl-5H-pyrrolo[3,2-d]pyrimidin-4-amine;
2-Butyl-6-methyl-7-(6-(pyrrolidin-1-yl)hexyl)-5H-pyrrolo[3,2-d]pyrimidin-4-amine;

7-(6-(Azetidin-1-yl)hexyl)-2-butyl-6-methyl-5H-pyrrolo[3,2-d]pyrimidin-4-amine;
2-Butyl-6-methyl-7-(5-(pyrrolidin-1-yl)pentyl)-5H-pyrrolo[3,2-d]pyrimidin-4-amine;
7-(5-(Azetidin-1-yl)pentyl)-2-butyl-5H-pyrrolo[3,2-d]pyrimidin-4-amine;
7-(5-(Azetidin-1-yl)pentyl)-2-butyl-6-methyl-5H-pyrrolo[3,2-d]pyrimidin-4-amine;
2-Butyl-6-methyl-7-(4-(pyrrolidin-1-yl)butyl)-5H-pyrrolo[3,2-d]pyrimidin-4-amine;
2-Butyl-7-(5-(4,4-difluoropiperidin-1-yl)pentyl)-5H-pyrrolo[3,2-d]pyrimidin-4-amine;
2-Butyl-7-(5-(4-fluoropiperidin-1-yl)pentyl)-5H-pyrrolo[3,2-d]pyrimidin-4-amine;
7-(5-(4-Fluoropiperidin-1-yl)pentyl)-2-(2-methoxyethyl)-5H-pyrrolo[3,2-d]pyrimidin-4-amine;
1-(5-(4-Amino-2-butyl-5H-pyrrolo[3,2-d]pyrimidin-7-yl)pentyl)piperidin-4-ol;
(R)-2-Butyl-7-(5-(3-fluoropyrrolidin-1-yl)pentyl)-5H-pyrrolo[3,2-d]pyrimidin-4-amine;
(S)-2-Butyl-7-(5-(3-fluoropyrrolidin-1-yl)pentyl)-5H-pyrrolo[3,2-d]pyrimidin-4-amine;
(R)-7-(5-(3-Fluoropyrrolidin-1-yl)pentyl)-2-(2-methoxyethyl)-5H-pyrrolo[3,2-d]pyrimidin-4-amine;
(S)-7-(5-(3-Fluoropyrrolidin-1-yl)pentyl)-2-(2-methoxyethyl)-5H-pyrrolo[3,2-d]pyrimidin-4-amine;
(S)-1-(5-(4-Amino-2-butyl-5H-pyrrolo[3,2-d]pyrimidin-7-yl)pentyl)pyrrolidin-3-ol; and
1-(5-(4-Amino-2-butyl-5H-pyrrolo[3,2-d]pyrimidin-7-yl)pentyl)azetidin-3-ol;
7-(6-(Azepan-1-yl)hexyl)-2-(2-methoxyethyl)-5H-pyrrolo[3,2-d]pyrimidin-4-amine;
2-Butyl-7-(6-(4-fluoropiperidin-1-yl)hexyl)-5H-pyrrolo[3,2-d]pyrimidin-4-amine;
(R)-2-Butyl-7-(6-(3-fluoropyrrolidin-1-yl)hexyl)-5H-pyrrolo[3,2-d]pyrimidin-4-amine;
(S)-2-Butyl-7-(6-(3-fluoropyrrolidin-1-yl)hexyl)-5H-pyrrolo[3,2-d]pyrimidin-4-amine;
(S)-2-Butyl-7-(5-(2-methylpyrrolidin-1-yl)pentyl)-5H-pyrrolo[3,2-d]pyrimidin-4-amine;
(R)-2-Butyl-7-(5-(2-methylpyrrolidin-1-yl)pentyl)-5H-pyrrolo[3,2-d]pyrimidin-4-amine;
2-Butyl-7-(5-(3-methylazetidin-1-yl)pentyl)-5H-pyrrolo[3,2-d]pyrimidin-4-amine;
2-Butyl-7-(5-(3-fluoroazetidin-1-yl)pentyl)-5H-pyrrolo[3,2-d]pyrimidin-4-amine;
2-Butyl-6-methyl-7-(6-(pyrrolidin-1-yl)hexyl)-5H-pyrrolo[3,2-d]pyrimidin-4-amine;
2-Butyl-7-(5-(4-fluoropiperidin-1-yl)pentyl)-6-methyl-5H-pyrrolo[3,2-d]pyrimidin-4-amine;
(S)-2-Butyl-7-(5-(3-fluoropyrrolidin-1-yl)pentyl)-6-methyl-5H-pyrrolo[3,2-d]pyrimidin-4-amine;
(R)-2-Butyl-7-(5-(3-fluoropyrrolidin-1-yl)pentyl)-6-methyl-5H-pyrrolo[3,2-d]pyrimidin-4-amine;
2-Butyl-7-(5-(3-fluoroazetidin-1-yl)pentyl)-6-methyl-5H-pyrrolo[3,2-d]pyrimidin-4-amine;
2-(2-Methoxyethyl)-7-(5-(pyrrolidin-1-yl)pentyl)-5H-pyrrolo[3,2-d]pyrimidin-4-amine,
and salts thereof.

As used herein, the term "alkyl" refers to a saturated, straight hydrocarbon chain having the specified number of member atoms. For example, n-$C_{4-6}$ alkyl refers to a saturated, straight hydrocarbon chain having from 4 to 6 carbon atoms. Unless otherwise stated, alkyl groups are unsubstituted. The term "alkyl" includes, but is not limited to, n-butyl.

As used herein, the term "alkoxy" refers to a saturated, straight hydrocarbon chain having the specified number of member atoms linked be a single bond to an oxygen atom. For example, $C_{1-2}$alkoxy refers to an alkoxy group having 1 or 2 carbon atoms, which would be referred to as methoxy or ethoxy respectively.

As used herein, the term "halo" refers to fluoro, chloro, bromo and iodo.

It is to be understood that references herein to compounds of the invention mean a compound of formula (I) as the free base, or as a salt, for example a pharmaceutically acceptable salt.

In one aspect of the invention, a compound of formula (I) is in the form of a free base.

Salts of the compounds of formula (I) include pharmaceutically acceptable salts and salts which may not be pharmaceutically acceptable but may be useful in the preparation of compounds of formula (I) and pharmaceutically acceptable salts thereof. In one aspect of the invention, a compound of formula (I) is in the form of a pharmaceutically acceptable salt. Salts may be derived from certain inorganic or organic acids.

Examples of salts are pharmaceutically acceptable salts. Pharmaceutically acceptable salts include acid addition salts. For a review on suitable salts see Berge et al., *J. Pharm. Sci.*, 66:1-19 (1977).

Examples of pharmaceutically acceptable acid addition salts of a compound of formula (I) include inorganic acids such as, for example, hydrochloric acid, hydrobromic acid, orthophosphoric acid, nitric acid, phosphoric acid, or sulphuric acid, or with organic acids such as, for example, methanesulphonic acid, ethanesulphonic acid, p-toluenesulphonic acid, acetic acid, propionic acid, lactic acid, citric acid, fumaric acid, malic acid, succinic acid, salicylic acid, maleic acid, glycerophosphoric acid, tartaric, benzoic, glutamic, aspartic, benzenesulphonic, naphthalenesulphonic such as 2-naphthalenesuphonic, hexanoic acid or acetylsalicylic acid.

The invention includes within its scope all possible stoichiometric and non-stoichiometric forms of the salts of the compounds of formula (I). For example, a dimaleate or hemi-succinate salt of the compound of formula (I).

Salts may be formed using techniques well-known in the art, for example by precipitation from solution followed by filtration, or by evaporation of the solvent.

Typically, a pharmaceutically acceptable acid addition salt can be formed by reaction of a compound of formula (I) with a suitable acid (such as hydrobromic, hydrochloric, sulphuric, maleic, p-toluenesulphonic, methanesulphonic, naphthalenesulphonic or succinic acids), optionally in a suitable solvent such as an organic solvent, to give the salt which is usually isolated for example by crystallisation and filtration.

It will be appreciated that many organic compounds can form complexes with solvents in which they are reacted or from which they are precipitated or crystallised. These complexes are known as "solvates". For example, a complex with water is known as a "hydrate". Solvents with high boiling points and/or solvents with a high propensity to form hydrogen bonds such as water, ethanol, iso-propyl alcohol, and N-methyl pyrrolidinone may be used to form solvates. Methods for the identification of solvated include, but are not limited to, NMR and microanalysis. Solvates of the compounds of formula (I) are within the scope of the invention. As used herein, the term solvate encompasses solvates of both a free base compound as well as any salt thereof.

Certain of the compounds of the invention may contain chiral atoms and/or multiple bonds, and hence may exist in one or more stereoisomeric forms. The present invention encompasses all of the stereoisomers of the compounds of the invention, including optical isomers, whether as individual stereoisomers or as mixtures thereof including racemic modifications. Any stereoisomer may contain less than 10% by weight, for example less than 5% by weight, or less than 0.5% by weight, of any other stereoisomer. For example, any optical isomer may contain less than 10% by weight, for example less than 5% by weight, or less than 0.5% by weight, of its antipode.

Certain of the compounds of the invention may exist in tautomeric forms. It will be understood that the present invention encompasses all of the tautomers of the compounds of the invention whether as individual tautomers or as mixtures thereof.

The compounds of the invention may be in crystalline or amorphous form. Furthermore, some of the crystalline forms of the compounds of the invention may exist as polymorphs, all of which are included within the scope of the present invention. The most thermodynamically stable polymorphic form or forms of the compounds of the invention are of particular interest.

Polymorphic forms of compounds of the invention may be characterised and differentiated using a number of conventional analytical techniques, including, but not limited to, X-ray powder diffraction (XRPD), infrared spectroscopy (IR), Raman spectroscopy, differential scanning calorimetry (DSC), thermogravimetric analysis (TGA) and solid-state nuclear magnetic resonance (ssNMR).

The present invention also includes all suitable isotopic variations of a compound of formula (I) or a pharmaceutically acceptable salt thereof. An isotopic variation of a compound of formula (I), or a pharmaceutically acceptable salt thereof, is defined as one in which at least one atom is replaced by an atom having the same atomic number but an atomic mass different from the atomic mass usually found in nature. Examples of isotopes that can be incorporated into compounds of the invention include isotopes of hydrogen, carbon, nitrogen, oxygen, fluorine and chlorine such as $^{2}H$, $^{3}H$, $^{13}C$, $^{14}C$, $^{15}N$, $^{17}O$, $^{18}O$, $^{18}F$ and $^{36}Cl$, respectively. Certain isotopic variations of a compound of formula (I) or a salt or solvate thereof, for example, those in which a radioactive isotope such as $^{3}H$ or $^{14}C$ is incorporated, are useful in drug and/or substrate tissue distribution studies. Tritiated, i.e., $^{3}H$, and carbon-14, i.e., $^{14}C$, isotopes are particularly preferred for their ease of preparation and detectability. Further, substitution with isotopes such as deuterium, i.e., $^{2}H$, may afford certain therapeutic advantages resulting from greater metabolic stability, for example, increased in vivo half-life or reduced dosage requirements and hence may be preferred in some circumstances. Isotopic variations of a compound of formula (I), or a pharmaceutically salt thereof, can generally be prepared by conventional procedures such as by the illustrative methods or by the preparations described in the Examples hereafter using appropriate isotopic variations of suitable reagents.

It will be appreciated from the foregoing that included within the scope of the invention are solvates, hydrates, isomers and polymorphic forms of the compounds of formula (I) and salts and solvates thereof.

Compound Preparation

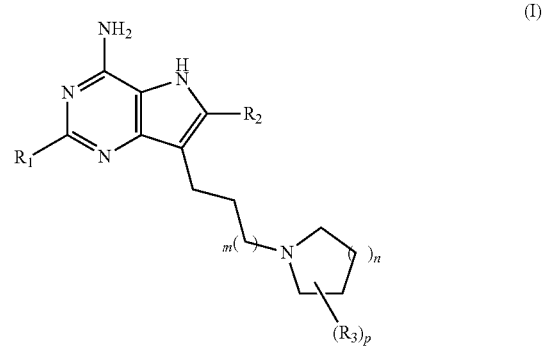

Accordingly, there is provided a process for the preparation of a compound of formula (I), which process comprises the deprotection of a compound of formula (II):

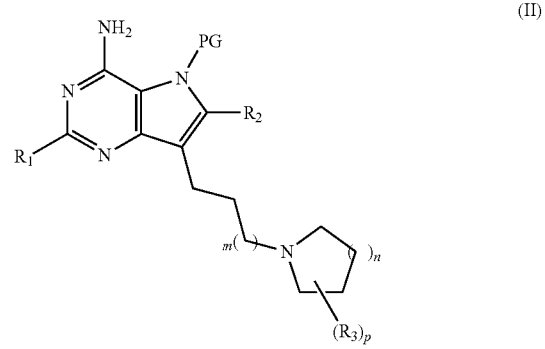

wherein $R_1$, $R_2$, $R_3$, m, n and p are as defined hereinbefore for a compound of formula (I) and PG is a protecting group, such as benzyloxymethyl (BOM), 2-(trimethylsilyl)ethoxymethyl (SEM) or p-toluenesufonyl and thereafter, if required, preparing a salt of the compound so-formed.

For example, a compound of formula (II) wherein PG is equivalent to BOM is dissolved in a suitable solvent, for example methanol or ethanol, and passed over a suitable catalyst, for example 10% palladium on carbon in the presence of hydrogen, at a suitable temperature, for example 20-60° C. in an apparatus such as the Thales H-Cube™. The product (I) is isolated by removal of the solvent and purification if required.

For example, a compound of formula (II) wherein PG is SEM is dissolved in a suitable solvent, for example tetrahydrofuran, and reacted with tetrabutylammonium fluoride and ethylenediamine at a suitable temperature, for example 70° C. The product (I) is isolated by removal of the solvent and purification if required.

A compound of formula (II) may be prepared by reaction of a compound of formula (III):

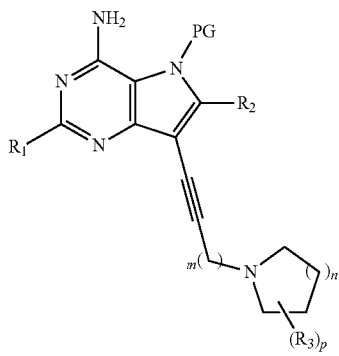

wherein $R_1$, $R_2$, $R_3$, m, n and p are as hereinbefore defined for a compound of formula (I) with hydrogen in the presence of a catalyst.

For example a compound of formula (III) is dissolved in a suitable solvent for example methyl alcohol or ethyl alcohol, and passed over a suitable catalyst, for example 10% palladium on carbon, in the presence of hydrogen at a suitable temperature, for example 20-60° C., in a suitable flow hydrogenation apparatus such as the Thales H-Cube™. The product (II) is isolated by removal of the solvent and purification if required.

When the protecting group is the benzyloxymethyl (BOM) group the reaction to reduction the alkyne can result in the simultaneous removal of the protecting group to afford compounds of formula (I) directly.

A compound of formula (III) may be prepared by reaction of a compound of formula (IV):

wherein $R_1$ and $R_2$ are as hereinbefore defined for a compound of formula (I) and Y is a leaving group for example a halogen such as iodine or bromine or an alkyl sulfonate such as a trifluoromethane sulfonate with a compound of formula (V):

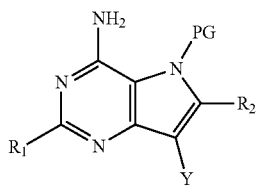

wherein $R_3$, m, n and p are defined for a compound of formula (I).

For example a compound of formula (IV), a compound of formula (V) are dissolved in a suitable solvent, for example N,N-dimethylformamide, in the presence of copper(I) iodide, a suitable catalyst, for example bis(triphenylphosphine)palladium(II) dichloride and a suitable base, for example triethylamine, and heated at a suitable temperature, for example 20-55° C. for a suitable period of time, for example 0.5-17 hours. The product (III) is isolated after an aqueous work-up and purification.

A compound of formula (V) may be prepared by reaction of a compound of formula (VI):

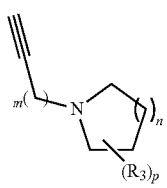

wherein m is defined for a compound of formula (I) and X is a leaving group such as a halogen, for example chlorine, bromine or iodine, or an alkyl sulfonate, for example p-toluenesulfonate, with a compound of formula (VII):

wherein $R_3$, n and p are as defined for a compound of formula (I).

For example a compound of formula (VI), a compound of formula (VII) and a suitable base, for example sodium hydrogen carbonate, are dissolved in a suitable solvent, for example N,N-dimethylformamide, and heated at a suitable temperature, for example 80-100° C. for a suitable period of time, for example 16-18 hours. The product (V) is isolated after aqueous work-up and purification, for example by isolation of a suitable crystalline salt, for example the oxalate salt.

Compounds of formula (VI) and formula (VII) are either commercially available or may be prepared by methods described in the literature.

Alternatively a compound of formula (III) may be prepared by reaction of a compound of formula (VIIIA) or formula (VIIIB):

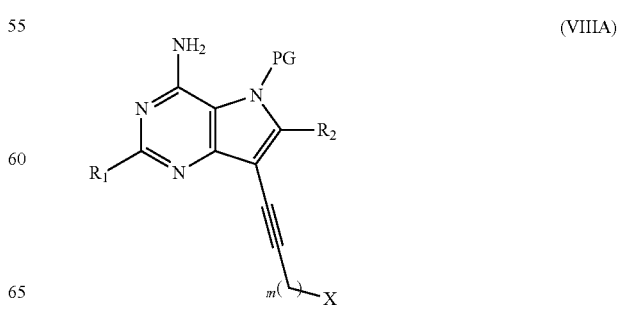

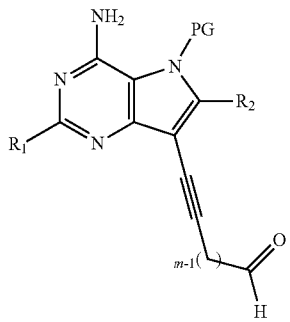

(VIIIB)

wherein $R_1$, $R_2$ and m are as hereinbefore defined for a compound of formula (I) and X is a leaving group as defined for compounds of formula (VI) with a compound of formula (VII).

For example a compound of formula (VIIIA), a compound of formula (VII) and a suitable base, for example triethylamine, are dissolved in a suitable solvent, for example acetontrile and heated at a suitable temperature, for example 60-80° C. for a suitable period of time, for example 16-26 hours. The product (III) is isolated after an aqueous work-up and purification.

For example a suitable reducing agent, for example sodium triacetoxyborohydride, is added to a mixture of a compound of formula (VIIIB), a compound of formula (VII) and a drying agent, for example 4 Å molecular sieves, in a suitable solvent, for example dichloromethane, and stirred at a suitable temperature, for example 20° C., for a suitable period of time, for example 1-2 hours. The product (III) is isolated after an aqueous work-up and purification.

Compounds of formula (VIIIA) can be prepared by reaction of compounds of formula (IV) with compounds of formula (VI). For example a compound of formula (IV), a compound of formula (VI) are dissolved in a suitable solvent, for example N,N-dimethylformamide, in the presence of copper(I) iodide, a suitable catalyst, for example bis(triphenylphosphine)palladium(II) dichloride and a suitable base, for example triethylamine, and heated at a suitable temperature, for example 20° C. for a suitable period of time, for example 18-20 hours. The product (VIIIA) is isolated after an aqueous work-up and purification.

Compounds of formula (VIIIB) can be prepared by reaction of compounds of formula (IX):

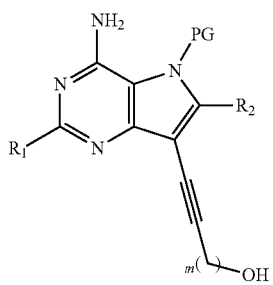

(IX)

wherein $R_1$, $R_2$ and m are as hereinbefore defined for a compound of formula (I) with an oxidising agent, for example tetrapropylammonium perruthenate in the presence of 4-methylmorpholine N-oxide.

For example a compound of formula (IX), a suitable oxidant, for example tetrapropylammonium perruthenate in the presence of 4-methylmorpholine N-oxide, in a suitable solvent, for example a mixture of dichloromethane and acetonitrile, was stirred at a suitable temperature, for example 20° C., for a suitable period of time, for example 2 hours. The reaction mixture is filtered and the product (VIIIB) isolated by removal of the solvent and purification if required.

Compounds of formula (IX) can be prepared by reaction of compounds of formula (IV) with appropriate alkyn-1-ols. For example a compound of formula (IV), the alkyn-1-ol are dissolved in a suitable solvent, for example N,N-dimethylformamide, in the presence of copper(I) iodide, a suitable catalyst, for example bis(triphenylphosphine)palladium(II) dichloride and a suitable base, for example triethylamine, and heated at a suitable temperature, for example 20° C. for a suitable period of time, for example 18-20 hours. The product (IX) is isolated after an aqueous work-up and purification.

Alternatively compounds of formula (II) may be prepared by reaction of compounds of formula (X):

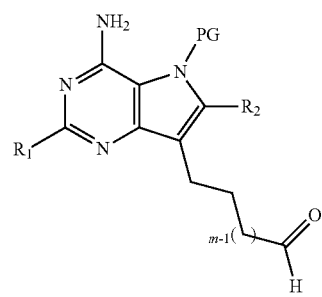

(X)

wherein $R_1$, $R_2$ and m are as hereinbefore defined for a compound of formula (I)

For example a suitable reducing agent, for example sodium triacetoxyborohydride, is added to a mixture of a compound of formula (X), a compound of formula (VII) and a drying agent, for example 4 Å molecular sieves, in a suitable solvent, for example dichloromethane, and stirred at a suitable temperature, for example 20° C., for a suitable period of time, for example 1-2 hours. The product (II) is isolated after an aqueous work-up and purification.

Compounds of formula (X) may be prepared by reaction of compounds of formula (XI):

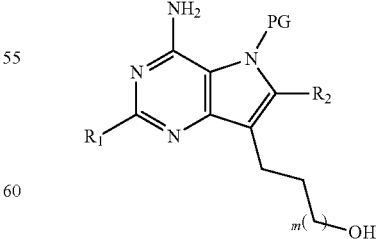

(XI)

wherein $R_1$, $R_2$ and m are as hereinbefore defined for a compound of formula (I)

For example a compound of formula (XI), a suitable oxidant, for example tetrapropylammonium perruthenate in the presence of 4-methylmorpholine N-oxide, in a suitable solvent, for example a mixture of dichloromethane and acetonitrile, was stirred at a suitable temperature, for example 20° C., for a suitable period of time, for example 2 hours. The product (X) isolated by removal of the solvent and purification if required.

Compounds of formula (XI) may be prepared by reaction of compounds of formula (IX) with hydrogen in the presence of a catalyst. For example a compound of formula (IX) is dissolved in a suitable solvent, for example ethanol, and passed over a suitable catalyst, for example 10% palladium on carbon in the presence of hydrogen, at a suitable temperature, for example 20-60° C. in an apparatus such as the Thales H-Cube™. The product (XI) is isolated by removal of the solvent and purification if required.

Compounds of formula (IV) may be prepared by reaction of compounds of formula (XII):

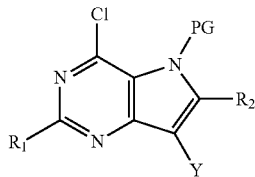

(XII)

wherein $R_1$ and $R_2$ are as hereinbefore defined for a compound of formula (I) and Y is defined for a compound of formula (IV) with a solution of ammonia.

For example a solution of aqueous ammonia (0.88) is added to a solution of a compound of formula (XII) in a suitable solvent, for example iso-propyl alcohol. The resultant mixture is then heated in a microwave heater at a suitable temperature, for example 120-150° C. for a suitable period of time, for example 1-2 hours. The product (IV) is isolated after an aqueous work-up and purification.

Compounds of formula (XII) may be prepared by reaction of compounds of formula (XIII):

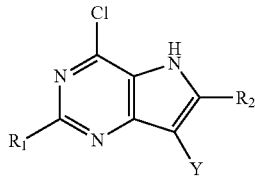

(XIII)

wherein $R_1$ and $R_2$ are as hereinbefore defined for a compound of formula (I) with a compound of formula (XIV):

(XIV)

wherein compound of formula (XIV) is a suitable precursor to the protecting group PG, for example benzyl chloromethyl ether or (2-(chloromethoxy)ethyl)trimethylsilane.

For example, a compound of formula (XIII) in a suitable solvent, for example N,N-dimethylformamide or tetrahydrofuran, is treated with a suitable base, for example a suspension of sodium hydride in oil. A compound of formula (XIV), for example benzyl chloromethyl ether or (2-(chloromethoxy)ethyl)trimethylsilane is added and the reaction mixture is stirred at a suitable temperature, for example 20° C. for a suitable period of time, for example 1-4 hours. The product (XII) is isolated after an aqueous work-up and purification.

Compounds of formula (XIII) may be prepared by reaction of compounds of formula (XV):

(XV)

wherein $R_1$ and $R_2$ are as hereinbefore defined for a compound of formula (I) with a halogenating reagent, for example N-iodosuccinimide.

For example a compound of formula (XV) is dissolved in a suitable solvent, for example tetrahydrofuran, is reacted with N-iodosuccinimide at suitable temperature, for example 20° C. for a suitable period of time, for example 1-2 hours. The product (XIII) is isolated after an aqueous work-up and purification.

Compounds of formula (XV) may be prepared by reaction of compounds of formula (XVI):

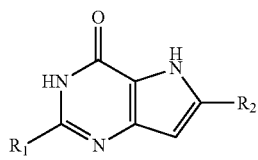

(XVI)

wherein $R_1$ and $R_2$ are as hereinbefore defined for a compound of formula (I) with a chlorinating reagent, for example phosphorus oxychloride.

For example a compound of formula (XVI) is suspended in phosphorus oxychloride and heated at a suitable temperature, for example 120° C. for a suitable period of time, for example 3-4 hours. Excess phosphorus oxychloride may be removed in vacuo then the residue is poured onto ice and the pH of the mixture adjusted to 7-9. The product is then extracted into a suitable organic solvent, for example ethyl acetate. The product (XV) is isolated by removal of the solvent and purification if required.

Compounds of formula (XVI) may be prepared by reaction of compounds of formula (XVII):

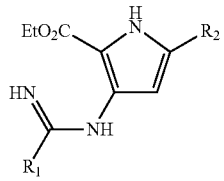

(XVII)

wherein $R_1$ and $R_2$ are as hereinbefore defined for a compound of formula (I) with a suitable base, for example sodium hydroxide.

For example a solution of compounds of formula (XVII) in a suitable solvent, for example ethyl alcohol, is treated with an aqueous solution of sodium hydroxide and the reaction mixture stirred at a suitable temperature, for example 80-100° C. for a suitable period of time, for example 4-18 hours. The product (XVI) is isolated after an aqueous work-up and purification.

Compounds of formula (XVII) can be prepared by reaction of compounds of formula (XVIII):

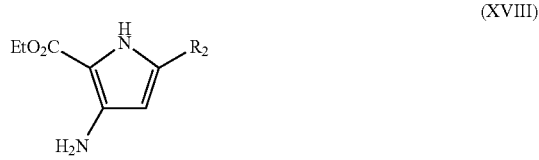

(XVIII)

with compounds of formula (XIX):

(XIX)

wherein $R_1$ and $R_2$ are as hereinbefore defined for a compound of formula (I).

For example, a suspension of a compound of formula (XVIII) in a compound of formula (XIX) is treated with a solution of hydrogen chloride in a suitable solvent, for example a solution of hydrogen chloride in 1,4-dioxane and is heated at a suitable temperature, 50-70° C. for a suitable period of time, for example 16-18 hours. The product (XVIII) is isolated after filtration after the addition of a suitable solvent, for example tert-butyl methyl ether.

Alternatively compound of formula (XVI) can be prepared by reaction of compounds of formula (XVIII) with compounds of formula (XX):

(XX)

wherein $R_1$ is as hereinbefore defined for a compound of formula (I).

For example, a mixture of compounds of formula (XVIII) and compounds of formula (XX) are heated in a suitable solvent, for example o-xylene, at a suitable temperature, for example reflux, for a suitable period of time, for example, 3 days. After cooling to ambient temperature the product (XVI) is isolated after filtration.

Compounds of formulae (VI), (VII), (XIV), (XVIII), (XIX) and (XX) are either known in the literature or are commercially available, for example from Sigma-Aldrich, UK, or may be prepared by analogy with known procedures, for example those disclosed in standard reference texts of synthetic methodology such as *J. March, Advanced Organic Chemistry, 6th Edition* (2007), WileyBlackwell, or *Comprehensive Organic Synthesis* (Trost B. M. and Fleming I., (Eds.), Pergamon Press, 1991), each incorporated herein by reference as it relates to such procedures.

Examples of other protecting groups that may be employed in the synthetic routes described herein and the means for their removal can be found in T W. Greene '*Protective Groups in Organic Synthesis*', 4th Edition, J. Wiley and Sons, 2006, incorporated herein by reference as it relates to such procedures.

For any of the hereinbefore described reactions or processes, conventional methods of heating and cooling may be employed, for example temperature-regulated oil-baths or temperature-regulated hot-blocks, and icesalt baths or dry iceacetone baths respectively. Conventional methods of isolation, for example extraction from or into aqueous or non-aqueous solvents may be used. Conventional methods of drying organic solvents, solutions, or extracts, such as shaking with anhydrous magnesium sulphate, or anhydrous sodium sulphate, or passing through a hydrophobic frit, may be employed.

Conventional methods of purification, for example crystallisation and chromatography, for example silica chromatography or reverse-phase chromatography, may be used as required. Crystallisation may be performed using conventional solvents such as ethyl acetate, methanol, ethanol, or butanol, or aqueous mixtures thereof. It will be appreciated that specific reaction times temperatures may typically be determined by reaction-monitoring techniques, for example thin-layer chromatography and LC-MS.

Where appropriate individual isomeric forms of the compounds of the invention may be prepared as individual isomers using conventional procedures such as the fractional crystallisation of diastereoisomeric derivatives or chiral high performance liquid chromatography (chiral HPLC).

The absolute stereochemistry of compounds may be determined using conventional methods, such as X-ray crystallography.

Methods of Use

Examples of disease states in which the compounds of formula (I) and pharmaceutically acceptable salts thereof have potentially beneficial effects include allergic diseases and other inflammatory conditions for example allergic rhinitis and asthma, infectious diseases, and cancer.

As modulators of the immune response the compounds of formula (I) and pharmaceutically acceptable salts thereof may also be useful in the treatment and/or prevention of immune-mediated disorders, including but not limited to inflammatory or allergic diseases such as asthma, allergic rhinitis and rhinoconjuctivitis, food allergy, hypersensitivity lung diseases, eosinophilic pneumonitis, delayed-type hypersensitivity disorders, atherosclerosis, pancreatitis, gastritis, colitis, osteoarthritis, psoriasis, sarcoidosis, pulmonary fibrosis, respiratory distress syndrome, bronchiolitis, chronic obstructive pulmonary disease, sinusitis, cystic fibrosis, actinic keratosis, skin dysplasia, chronic urticaria, eczema and all types of dermatitis.

The compounds of formula (I) and pharmaceutically acceptable salts thereof may also be useful in the treatment and/or prevention of reactions against respiratory infections, including but not limited to airways viral exacerbations and tonsillitis. The compounds may also be useful in the treatment and/or prevention of autoimmune diseases including but not limited to rheumatoid arthritis, psoriatic arthritis, systemic lupus erythematosus, Sjöegrens disease, ankylosing spondylitis, scleroderma, dermatomyositis, diabetes, graft rejection, including graft-versus-host disease, inflammatory bowel diseases including, but not limited to, Crohn's disease and ulcerative colitis.

The compounds of formula (I) and pharmaceutically acceptable salts thereof may also be useful in the treatment of infectious diseases including, but not limited to, those caused by hepatitis viruses (e.g. hepatitis B virus, hepatitis C virus), human immunodeficiency virus, papillomaviruses, herpesviruses, respiratory viruses (e.g. influenza viruses, respiratory syncytial virus, rhinovirus, metapneumovirus, parainfluenzavirus, SARS), and West Nile virus. The compounds of formula (I) and pharmaceutically acceptable salts thereof may also be useful in the treatment of microbial infections caused by, for example, bacteria, fungi, or protozoa. These include, but are not limited to, tuberculosis, bacterial pneumonia, aspergillosis, histoplasmosis, candidosis, pneumocystosis, leprosy, chlamydia, cryptococcal disease, cryptosporidosis, toxoplasmosis, leishmania, malaria, and trypanosomiasis.

The compounds of formula (I) and pharmaceutically acceptable salts thereof may also be useful in the treatment of various cancers, in particular the treatment of cancers that are known to be responsive to immunotherapy and including, but not limited to, renal cell carcinoma, lung cancer, breast cancer, colorectal cancer, bladder cancer, melanoma, leukaemia, lymphomas and ovarian cancer.

It will be appreciated by those skilled in the art that references herein to treatment or therapy may, depending on the condition, extend to prophylaxis as well as the treatment of established conditions.

There is thus provided as a further aspect of the invention a compound of formula (I), or a pharmaceutically acceptable salt thereof, for use in therapy.

It will be appreciated that, when a compound of formula (I) or a pharmaceutically acceptable salt thereof is used in therapy, it is used as an active therapeutic agent.

There is also therefore provided a compound of formula (I), or a pharmaceutically acceptable salt thereof, for use in the treatment of allergic diseases and other inflammatory conditions, infectious diseases, and cancer.

There is also therefore provided a compound of formula (I), or a pharmaceutically acceptable salt thereof, for use in the treatment of allergic rhinitis.

There is also therefore provided a compound of formula (I), or a pharmaceutically acceptable salt thereof, for use in the treatment of asthma.

There is further provided the use of a compound of formula (I), or a pharmaceutically acceptable salt thereof, in the manufacture of a medicament for the treatment of allergic diseases and other inflammatory conditions, infectious diseases, and cancer.

There is further provided the use of a compound of formula (I), or a pharmaceutically acceptable salt thereof, in the manufacture of a medicament for the treatment of allergic rhinitis.

There is further provided the use of a compound of formula (I), or a pharmaceutically acceptable salt thereof, in the manufacture of a medicament for the treatment of asthma.

There is further provided a method of treatment of allergic diseases and other inflammatory conditions, infectious diseases, and cancer, which method comprises administering to a human subject in need thereof, a therapeutically effective amount of a compound of formula (I), or a pharmaceutically acceptable salt thereof.

There is further provided a method of treatment of allergic rhinitis, which method comprises administering to a human subject in need thereof, a therapeutically effective amount of a compound of formula (I), or a pharmaceutically acceptable salt thereof.

There is further provided a method of treatment of asthma, which method comprises administering to a human subject in need thereof, a therapeutically effective amount of a compound of formula (I), or a pharmaceutically acceptable salt thereof.

The compounds of formula (I) and pharmaceutically acceptable salts thereof are also of potential use as vaccine adjuvants.

There is thus provided as a further aspect of the invention a vaccine composition comprising a compound of formula (I), or a pharmaceutically acceptable salt thereof, and an antigen or antigen composition for use in therapy.

There is thus provided as a further aspect of the invention the use of a compound of formula (I), or a pharmaceutically acceptable salt thereof, and an antigen or antigen composition in the manufacture of a medicament for use in therapy.

There is further provided a method of treating or preventing disease comprising the administration to a human subject suffering from or susceptible to disease, a vaccine composition comprising a compound of formula (I), or a pharmaceutically acceptable salt thereof, and an antigen or antigen composition.

Compositions

The compounds of formula (I) and pharmaceutically acceptable salts thereof will normally, but not necessarily, be formulated into pharmaceutical compositions prior to administration to a patient. Accordingly, in another aspect of the invention there is provided a pharmaceutical composition comprising a compound of formula (I), or a pharmaceutically acceptable salt thereof, and one or more pharmaceutically acceptable excipients.

The compounds of formula (I) and pharmaceutically acceptable salts thereof may be formulated for administration in any convenient way. The compounds of formula (I) and pharmaceutically acceptable salts thereof may, for example, be formulated for oral, topical, inhaled, intranasal, buccal, parenteral (for example intravenous, subcutaneous, intradermal, or intramuscular) or rectal administration. In one aspect, the compounds of formula (I) and pharmaceutically acceptable salts thereof are formulated for oral administration. In a further aspect, the compounds of formula (I) and pharmaceutically acceptable salts thereof are formulated for topical administration, for example intranasal or inhaled administration.

Tablets and capsules for oral administration may contain conventional excipients such as binding agents, for example syrup, acacia, gelatin, sorbitol, tragacanth, mucilage of starch, cellulose or polyvinyl pyrrolidone; fillers, for example, lactose, microcrystalline cellulose, sugar, maize starch, calcium phosphate or sorbitol; lubricants, for example, magnesium stearate, stearic acid, talc, polyethylene glycol or silica; disintegrants, for example, potato starch, croscarmellose sodium or sodium starch glycollate; or wetting agents such as sodium lauryl sulphate. The tablets may be coated according to methods well known in the art.

Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, glucosesugar syrup, gelatin, hydroxymethyl cellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example almond oil, fractionated coconut oil, oily esters, propylene glycol or ethyl alcohol; or preservatives, for example, methyl or propyl p-hydroxybenzoates or sorbic acid. The preparations may also contain buffer salts, flavouring, colouring and/or sweetening agents (e.g. mannitol) as appropriate.

Compositions for intranasal administration include aqueous compositions administered to the nose by drops or by pressurised pump. Suitable compositions contain water as the diluent or carrier for this purpose. Compositions for administration to the lung or nose may contain one or more excipients, for example one or more suspending agents, one or more preservatives, one or more surfactants, one or more tonicity adjusting agents, one or more co-solvents, and may include components to control the pH of the composition, for example a buffer system. Further, the compositions may contain other excipients such as antioxidants, for example sodium metabisulphite, and taste-masking agents. Compositions may also be administered to the nose or other regions of the respiratory tract by nebulisation.

Intranasal compositions may permit the compound(s) of formula (I) or (a) pharmaceutically acceptable salt(s) thereof to be delivered to all areas of the nasal cavities (the target tissue) and further, may permit the compound(s) of formula (I) or (a) pharmaceutically acceptable salt(s) thereof to remain in contact with the target tissue for longer periods of time. A suitable dosing regime for intranasal compositions would be for the patient to inhale slowly through the nose subsequent to the nasal cavity being cleared. During inhalation the composition would be administered to one nostril while the other is manually compressed. This procedure would then be repeated for the other nostril. Typically, one or two sprays per nostril would be administered by the above procedure one, two, or three times each day, ideally once daily. Of particular interest are intranasal compositions suitable for once-daily administration.

The suspending agent(s), if included, will typically be present in an amount of from 0.1 to 5% (w/w), such as from 1.5% to 2.4% (w/w), based on the total weight of the composition. Examples of pharmaceutically acceptable suspending agents include, but are not limited to, Avicel® (microcrystalline cellulose and carboxymethylcellulose sodium), carboxymethylcellulose sodium, veegum, tragacanth, bentonite, methylcellulose, xanthan gum, carbopol and polyethylene glycols.

Compositions for administration to the lung or nose may contain one or more excipients may be protected from microbial or fungal contamination and growth by inclusion of one or more preservatives. Examples of pharmaceutically acceptable anti-microbial agents or preservatives include, but are not limited to, quaternary ammonium compounds (for example benzalkonium chloride, benzethonium chloride, cetrimide, cetylpyridinium chloride, lauralkonium chloride and myristyl picolinium chloride), mercurial agents (for example phenylmercuric nitrate, phenylmercuric acetate and thimerosal), alcoholic agents (for example chlorobutanol, phenylethyl alcohol and benzyl alcohol), antibacterial esters (for example esters of para-hydroxybenzoic acid), chelating agents such as disodium edetate (EDTA) and other anti-microbial agents such as chlorhexidine, chlorocresol, sorbic acid and its salts (such as potassium sorbate) and polymyxin. Examples of pharmaceutically acceptable anti-fungal agents or preservatives include, but are not limited to, sodium benzoate, sorbic acid, sodium propionate, methylparaben, ethylparaben, propylparaben and butylparaben. The preservative(s), if included, may be present in an amount of from 0.001 to 1% (w/w), such as from 0.015% to 0.5% (w/w) based on the total weight of the composition.

Compositions (for example wherein at least one compound is in suspension) may include one or more surfactants which functions to facilitate dissolution of the medicament particles in the aqueous phase of the composition. For example, the amount of surfactant used is an amount which will not cause foaming during mixing. Examples of pharmaceutically acceptable surfactants include fatty alcohols, esters and ethers, such as polyoxyethylene (20) sorbitan monooleate (Polysorbate 80), macrogol ethers, and poloxamers. The surfactant may be present in an amount of between about 0.01 to 10% (w/w), such as from 0.01 to 0.75% (w/w), for example about 0.5% (w/w), based on the total weight of the composition.

One or more tonicity-adjusting agent(s) may be included to achieve tonicity with body fluids e.g. fluids of the nasal cavity, resulting in reduced levels of irritancy. Examples of pharmaceutically acceptable tonicity-adjusting agents include, but are not limited to, sodium chloride, dextrose, xylitol, calcium chloride, glucose, glycerine and sorbitol. A tonicity-adjusting agent, if present, may be included in an amount of from 0.1 to 10% (w/w), such as from 4.5 to 5.5% (w/w), for example about 5.0% (w/w), based on the total weight of the composition.

The compositions of the invention may be buffered by the addition of suitable buffering agents such as sodium citrate, citric acid, trometamol, phosphates such as disodium phosphate (for example the dodecahydrate, heptahydrate, dihydrate and anhydrous forms), or sodium phosphate and mixtures thereof.

A buffering agent, if present, may be included in an amount of from 0.1 to 5% (w/w), for example 1 to 3% (w/w) based on the total weight of the composition.

Examples of taste-masking agents include sucralose, sucrose, saccharin or a salt thereof, fructose, dextrose, glycerol, corn syrup, aspartame, acesulfame-K, xylitol, sorbitol, erythritol, ammonium glycyrrhizinate, thaumatin, neotame, mannitol, menthol, eucalyptus oil, camphor, a natural flavouring agent, an artificial flavouring agent, and combinations thereof.

One or more co-solvent(s) may be included to aid solubility of the medicament compound(s) and/or other excipients. Examples of pharmaceutically acceptable co-solvents include, but are not limited to, propylene glycol, dipropylene glycol, ethylene glycol, glycerol, ethanol, polyethylene glycols (for example PEG300 or PEG400), and methanol. In one embodiment, the co-solvent is propylene glycol.

Co-solvent(s), if present, may be included in an amount of from 0.05 to 30% (w/w), such as from 1 to 25% (w/w), for example from 1 to 10% (w/w) based on the total weight of the composition.

Compositions for inhaled administration include aqueous, organic or aqueousorganic mixtures, dry powder or crystalline compositions administered to the respiratory tract by pressurised pump or inhaler, for example, reservoir dry powder inhalers, unit-dose dry powder inhalers, pre-metered multi-dose dry powder inhalers, nasal inhalers or pressurised aerosol inhalers, nebulisers or insufflators. Suitable compositions contain water as the diluent or carrier for this purpose and may be provided with conventional excipients such as buffering agents, tonicity modifying agents and the like. Aqueous compositions may also be administered to the nose and other regions of the respiratory tract by nebulisation. Such compositions may be aqueous solutions or suspensions or aerosols delivered from pressurised packs, such as a metered dose inhaler, with the use of a suitable liquefied propellant.

Compositions for administration topically to the nose (for example, for the treatment of rhinitis) or to the lung, include pressurised aerosol compositions and aqueous compositions delivered to the nasal cavities by pressurised pump. Compositions which are non-pressurised and are suitable for administration topically to the nasal cavity are of particular interest. Suitable compositions contain water as the diluent or carrier for this purpose. Aqueous compositions for administration to the lung or nose may be provided with conventional excipients such as buffering agents, tonicity-modifying agents and the like. Aqueous compositions may also be administered to the nose by nebulisation.

A fluid dispenser may typically be used to deliver a fluid composition to the nasal cavities. The fluid composition may be aqueous or non-aqueous, but typically aqueous. The compound of formula (I), or a pharmaceutically acceptable salt thereof, may be formulated as a suspension or solution. Such a fluid dispenser may have a dispensing nozzle or dispensing orifice through which a metered dose of the fluid composition is dispensed upon the application of a user-applied force to a pump mechanism of the fluid dispenser. Such fluid dispensers are generally provided with a reservoir of multiple metered doses of the fluid composition, the doses being dispensable upon sequential pump actuations. Alternatively, the fluid dispenser for delivery of a fluid composition to the nasal cavities may be designed to be dose-limited, for example a single use dispenser comprising a single dose. The dispensing nozzle or orifice may be configured for insertion into the nostrils of the user for spray dispensing of the fluid composition into the nasal cavity. A fluid dispenser of the aforementioned type is described and illustrated in International Patent Application publication number WO 2005/044354 (Glaxo Group Limited). The dispenser has a housing which houses a fluid-discharge device having a compression pump mounted on a container for containing a fluid composition. The housing has at least one finger-operable side lever which is movable inwardly with respect to the housing to move the container upwardly in the housing by means of a cam to cause the pump to compress and pump a metered dose of the composition out of a pump stem through a nasal nozzle of the housing. In one embodiment, the fluid dispenser is of the general type illustrated in FIGS. 30-40 of WO 2005/044354.

Aqueous compositions containing a compound of formula (I) or a pharmaceutically acceptable salt thereof may also be delivered by a pump as disclosed in International Patent Application publication number WO2007/38084 (Glaxo Group Limited), for example as disclosed with reference to FIGS. 22-46 thereof, or as disclosed in United Kingdom patent application number GB0723418.0 (Glaxo Group Limited), for example as disclosed with reference to FIGS. 7-32 thereof. The pump may be actuated by an actuator as disclosed in FIGS. 1-6 of GB0723418.0.

Dry powder compositions for topical delivery to the lung by inhalation may, for example, be presented in capsules and cartridges of for example gelatine, or blisters of for example laminated aluminium foil, for use in an inhaler or insufflator. Powder blend compositions generally contain a powder mix for inhalation of the compound of formula (I) or a pharmaceutically acceptable salt thereof and a suitable powder base (carrier/diluent/excipient substance) such as mono-, di-, or polysaccharides (for example lactose or starch). Dry powder compositions may also include, in addition to the drug and carrier, a further excipient (for example a ternary agent such as a sugar ester for example cellobiose octaacetate, calcium stearate, or magnesium stearate.

In one embodiment, a composition suitable for inhaled administration may be incorporated into a plurality of sealed dose containers provided on medicament pack(s) mounted inside a suitable inhalation device. The containers may be rupturable, peelable, or otherwise openable one-at-a-time and the doses of the dry powder composition administered by inhalation on a mouthpiece of the inhalation device, as known in the art. The medicament pack may take a number of different forms, for instance a disk-shape or an elongate strip. Representative inhalation devices are the DISKHALER™ and DISKUS™ devices, marketed by GlaxoSmithKline.

A dry powder inhalable composition may also be provided as a bulk reservoir in an inhalation device, the device then being provided with a metering mechanism for metering a dose of the composition from the reservoir to an inhalation channel where the metered dose is able to be inhaled by a patient inhaling at a mouthpiece of the device. Exemplary marketed devices of this type are TURBUHALER™ (AstraZeneca), TWISTHALER™ (Schering) and CLICKHALER™ (Innovata.)

A further delivery method for a dry powder inhalable composition is for metered doses of the composition to be provided in capsules (one dose per capsule) which are then loaded into an inhalation device, typically by the patient on demand. The device has means to rupture, pierce or otherwise open the capsule so that the dose is able to be entrained into the patient's lung when they inhale at the device mouthpiece. As marketed examples of such devices there may be mentioned ROTAHALER™ (GlaxoSmithKline) and HANDIHALER™ (Boehringer Ingelheim.)

Pressurised aerosol compositions suitable for inhalation can be either a suspension or a solution and may contain a compound of formula (I) or a pharmaceutically acceptable salt thereof and a suitable propellant such as a fluorocarbon or hydrogen-containing chlorofluorocarbon or mixtures thereof, particularly hydrofluoroalkanes, especially 1,1,1,2-tetrafluoroethane, 1,1,1,2,3,3,3-heptafluoro-n-propane or a mixture thereof. The aerosol composition may optionally contain additional composition excipients well known in the art such as surfactants e.g. oleic acid, lecithin or an oligo-lactic acid or derivative thereof e.g. as described in WO 9421229 and WO 9834596 (Minnesota Mining and Manufacturing Company) and co-solvents e.g. ethanol. Pressurised compositions will generally be retained in a canister (e.g. an aluminium canister) closed with a valve (e.g. a metering valve) and fitted into an actuator provided with a mouthpiece.

Ointments, creams and gels, may, for example, be formulated with an aqueous or oily base with the addition of suitable thickening and/or gelling agent and/or solvents. Such bases may thus, for example, include water and/or an oil such as liquid paraffin or a vegetable oil such as arachis oil or castor oil, or a solvent such as polyethylene glycol. Thickening agents and gelling agents which may be used according to the nature of the base include soft paraffin, aluminium stearate, cetostearyl alcohol, polyethylene glycols, wool-fat, beeswax, carboxypolymethylene and cellulose derivatives, and/or glyceryl monostearate and/or non-ionic emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents, suspending agents or preservatives.

The compounds of formula (I) and pharmaceutically acceptable salts thereof may, for example, be formulated for transdermal delivery by composition into patches or other devices (e.g. pressurised gas devices) which deliver the active component into the skin.

For buccal administration the compositions may take the form of tablets or lozenges formulated in the conventional manner.

The compounds of formula (I) and pharmaceutically acceptable salts thereof may also be formulated as suppositories, e.g. containing conventional suppository bases such as cocoa butter or other glycerides.

The compounds of formula (I) and pharmaceutically acceptable salts thereof may also be formulated for parenteral administration by bolus injection or continuous infusion and may be presented in unit dose form, for instance as ampoules, vials, small volume infusions or pre-filled syringes, or in multidose containers with an added preservative. The compositions may take such forms as solutions, suspensions, or emulsions in aqueous or non-aqueous vehicles, and may contain formulatory agents such as antioxidants, buffers, antimicrobial agents and/or tonicity adjusting agents. Alternatively, the active ingredient may be in powder form for constitution with a suitable vehicle, e.g. sterile, pyrogen-free water, before use. The dry solid presentation may be prepared by filling a sterile powder aseptically into individual sterile containers or by filling a sterile solution aseptically into each container and freeze-drying.

The compounds of formula (I) and pharmaceutically acceptable salts thereof may also be formulated with vaccines as adjuvants to modulate their activity. Such compositions may contain antibody(ies) or antibody fragment(s) or an antigenic component including but not limited to protein, DNA, live or dead bacteria and/or viruses or virus-like particles, together with one or more components with adjuvant activity including but not limited to aluminium salts, oil and water emulsions, heat shock proteins, lipid A preparations and derivatives, glycolipids, other TLR agonists such as CpG DNA or similar agents, cytokines such as GM-CSF or IL-12 or similar agents.

In a further aspect of the invention, there is provided a vaccine adjuvant comprising a compound of formula (I), or a pharmaceutically acceptable salt thereof.

There is further provided a vaccine composition comprising a compound of formula (I), or a pharmaceutically acceptable salt thereof, and an antigen or antigen composition.

The compounds of formula (I) and pharmaceutically acceptable salts thereof may be employed alone or in combination with other therapeutically-active agents. The invention provides in a further aspect, a combination comprising a compound of formula (I), or a pharmaceutically acceptable salt thereof, together with at least one other therapeutically-active agent.

The compounds of formula (I) and pharmaceutically acceptable salts thereof and the other therapeutically-active agent(s) may be administered together or separately and, when administered separately, administration may occur simultaneously or sequentially, in any order. The amounts of the compound(s) of formula (I) or (a) pharmaceutically acceptable salt(s) thereof and the other therapeutically-active agent(s) and the relative timings of administration will be selected in order to achieve the desired combined therapeutic effect. The administration of a combination of a compound of formula (I) or a pharmaceutically acceptable salt thereof with other treatment agents may be by administration concomitantly in a unitary pharmaceutical composition including both compounds, or in separate pharmaceutical compositions each including one of the compounds. Alternatively, the combination may be administered separately in a sequential manner wherein one treatment agent is administered first and the other second or vice versa. Such sequential administration may be close in time or remote in time.

The compounds of formula (I) and pharmaceutically acceptable salts thereof may be used in combination with one or more agents useful in the prevention or treatment of viral infections. Examples of such agents include, without limitation; polymerase inhibitors such as those disclosed in WO 2004/037818-A1, as well as those disclosed in WO 2004/037818 and WO 2006/045613; JTK-003, JTK-019, NM-283, HCV-796, R-803, R1728, R1626, as well as those disclosed in WO 2006/018725, WO 2004/074270, WO 2003/095441, US2005/0176701, WO 2006/020082, WO 2005/080388, WO 2004/064925, WO 2004/065367, WO 2003/007945, WO 02/04425, WO 2005/014543, WO 2003/000254, EP 1065213, WO 01/47883, WO 2002/057287, WO 2002/057245 and similar agents; replication inhibitors such as acyclovir, famciclovir, ganciclovir, cidofovir, lamivudine and similar agents; protease inhibitors such as the HIV protease inhibitors saquinavir, ritonavir, indinavir, nelfinavir, amprenavir, fosamprenavir, brecanavir, atazanavir, tipranavir, palinavir, lasinavir, and the HCV protease inhibitors BILN2061, VX-950, SCH503034; and similar agents; nucleoside and nucleotide reverse transcriptase inhibitors such as zidovudine, didanosine, lamivudine, zalcitabine, abacavir, stavidine, adefovir, adefovir dipivoxil, fozivudine, todoxil, emtricitabine, alovudine, amdoxovir, elvucitabine, and similar agents; non-nucleoside reverse transcriptase inhibitors (including an agent having anti-oxidation activity such as immunocal, oltipraz etc.) such as nevirapine, delavirdine, efavirenz, loviride, immunocal, oltipraz, capravirine, TMC-278, TMC-125, etravirine, and similar agents; entry inhibitors such as enfuvirtide (T-20), T-1249, PRO-542, PRO-140, TNX-355, BMS-806, 5-Helix and similar agents; integrase inhibitors such as L-870,180 and similar agents; budding inhibitors such as PA-344 and PA-457, and similar agents; chemokine receptor inhibitors such as vicriviroc (Sch-C), Sch-D, TAK779, maraviroc (UK-427,857), TAK449, as well as those disclosed in WO 0274769, WO 2004/054974, WO 2004/055012, WO 2004/055010, WO 2004/055016, WO 2004/055011, and WO 2004/054581, and similar agents; neuraminidase inhibitors such as CS-8958, zanamivir, oseltamivir, peramivir and similar agents; ion channel blockers such as amantadine or rimantadine and similar agents; and interfering RNA and antisense oligonucleotides and such as ISIS-14803 and similar agents; antiviral agents of undetermined mechanism of action, for example those disclosed in WO 2005/05761, WO 2003/085375, WO 2006/122011, ribavirin, and similar agents. The compounds of formula (I) and pharmaceutically acceptable salts thereof may also be used in combination with one or more other agents which may be useful in the prevention or treatment of viral infections for example immune therapies (e.g. interferon or other cytokineschemokines, cytokinechemokine receptor modulators, cytokine agonists or antagonists and similar agents); and therapeutic vaccines, antifibrotic agents, anti-inflammatory agents such as corticosteroids or NSAIDs (non-steroidal anti-inflammatory agents) and similar agents.

The compounds of formula (I) and pharmaceutically acceptable salts thereof may be used in combination with one or more other agents which may be useful in the prevention or treatment of allergic disease, inflammatory disease, autoimmune disease, for example; antigen immunotherapy, anti-histamines, steroids, NSAIDs, bronchodilators (e.g. beta 2 agonists, adrenergic agonists, anticholinergic agents, theophylline), methotrexate, leukotriene modulators and similar agents; monoclonal antibody therapy such as anti-IgE, anti-TNF, anti-IL-5, anti-IL-6, anti-IL-12, anti-IL-1 and similar agents; receptor therapies e.g. entanercept and similar agents; antigen non-specific immunotherapies (e.g. interferon or other cytokineschemokines, cytokinechemokine receptor modulators, cytokine agonists or antagonists, TLR agonists and similar agents).

The compounds of formula (I) and pharmaceutically acceptable salts thereof may be used in combination with one or more other agents which may be useful in the prevention or treatment of cancer, for example chemotherapeutics such as alkylating agents, topoisomerase inhibitors, antimetabolites, antimitotic agents, kinase inhibitors and similar agents; monoclonal antibody therapy such as trastuzumab, gemtuzumab and other similar agents; and hormone therapy such as tamoxifen, goserelin and similar agents.

The pharmaceutical compositions according to the invention may also be used alone or in combination with at least one other therapeutic agent in other therapeutic areas, for example gastrointestinal disease. The compositions according to the invention may also be used in combination with gene replacement therapy.

The invention includes in a further aspect a combination comprising a compound of formula (I), or a pharmaceutically acceptable salt thereof, together with at least one other therapeutically active agent.

The combinations referred to above may conveniently be presented for use in the form of a pharmaceutical composition and thus pharmaceutical compositions comprising a combination as defined above together with at least one pharmaceutically acceptable diluent or carrier thereof represent a further aspect of the invention.

A therapeutically effective amount of a compound of formula (I) or a pharmaceutically acceptable salt thereof will depend upon a number of factors. For example, the species, age, and weight of the recipient, the precise condition requiring treatment and its severity, the nature of the composition, and the route of administration are all factors to be considered. The therapeutically effective amount ultimately should be at the discretion of the attendant physician. Regardless, an effective amount of a compound of the present invention for the treatment of humans suffering from frailty, generally, should be in the range of 0.0001 to 100 mg/kg body weight of recipient per day. More usually the effective amount should be in the range of 0.001 to 10 mg/kg body weight per day. Thus, for a 70 kg adult one example of an actual amount per day would usually be from 7 to 700 mg. For intranasal and inhaled routes of administration, typical doses for a 70 kg adult should be in the range of 0.1 micrograms to 1 mg per day, for example 1 µg, 10 µg or 100 µg. This amount may be given in a single dose per day or in a number (such as two, three, four, five, or more) of sub-doses per day such that the total daily dose is the same. An effective amount of a pharmaceutically acceptable salt of a compound of formula (I) may be determined as a proportion of the effective amount of the compound of formula (I) or a pharmaceutically acceptable salt thereof per se. Similar dosages should be appropriate for treatment of the other conditions referred to herein.

Compounds of formula (I) and pharmaceutically acceptable salts thereof may also be administered at any appropriate frequency e.g. 1-7 times per week. The precise dosing regimen will of course depend on factors such as the therapeutic indication, the age and condition of the patient, and the particular route of administration chosen. In one aspect of the invention, a compound of formula (I), or a pharmaceutically acceptable salt thereof, may be administered once weekly for a period of 4 to 8 weeks, for example 4, 5, 6, 7 or 8 weeks.

Pharmaceutical compositions may be presented in unit-dose forms containing a predetermined amount of active ingredient per unit dose. Such a unit may contain, as a non-limiting example, 0.5 mg to 1 g of a compound of formula (I) or a pharmaceutically acceptable salt thereof, depending on the condition being treated, the route of administration, and the age, weight, and condition of the patient. Preferred unit-dosage compositions are those containing a daily dose or sub-dose, as herein above recited, or an appropriate fraction thereof, of an active ingredient. Such pharmaceutical compositions may be prepared by any of the methods well-known in the pharmacy art.

There is also provided a process for preparing such a pharmaceutical composition which comprises admixing a compound of formula (I), or a pharmaceutically acceptable salt thereof, with one or more pharmaceutically acceptable excipients.

The compounds of formula (I) and salts thereof may be prepared by the methodology described hereinafter, constituting further aspects of this invention.

Aspects of the invention are illustrated by reference to, but are in no way limited by, the following Examples.

Analytical Methodology $^1$H NMR $^1$H NMR spectra were recorded in either CDCl$_3$ or DMSO-d$_6$ on either a Bruker DPX 400 or Bruker Avance DRX, Varian Unity 400 spectrometer or JEOL Delta all working at 400 MHz. The internal standard used was either tetramethylsilane or the residual protonated solvent at 7.25 ppm for CDCl$_3$ or 2.50 ppm for DMSO-d$_6$.

LCMS

System A

Column: 50 mm×2.1 mm ID, 1.7 mm Acquity UPLC BEH C$_{18}$

Flow Rate: 1 mL/min.

Temp: 40° C.

UV detection range: 210 to 350 nm

Mass spectrum: Recorded on a mass spectrometer using alternative-scan positive and negative mode electrospray ionisation Solvents:

A: 0.1% v/v formic acid in water

B: 0.1% v/v formic acid acetonitrile

| Gradient: | | |
| --- | --- | --- |
| Time (min.) | A % | B % |
| 0 | 97 | 3 |
| 1.5 | 0 | 100 |
| 1.9 | 0 | 100 |
| 2.0 | 97 | 3 |

System B

Column: 50 mm×2.1 mm ID, 1.7 µm Acquity UPLC BEH C$_{18}$

Flow Rate: 1 mL/min.

Temp: 40° C.

UV detection range: 210 to 350 nm

Mass spectrum: Recorded on a mass spectrometer using alternative-scan positive and negative mode electrospray ionisation
Solvents:
  A: 10 mM ammonium bicarbonate in water adjusted to pH10 with ammonia solution
  B: acetonitrile

| Gradient: | | |
|---|---|---|
| Time (min.) | A % | B % |
| 0 | 99 | 1 |
| 1.5 | 3 | 97 |
| 1.9 | 3 | 97 |
| 2.0 | 0 | 100 |

Mass Directed Autopreparative HPLC (MDAP)

Mass directed autopreparative HPLC was undertaken under the conditions given below. The UV detection was an averaged signal from wavelength of 210 nm to 350 nm and mass spectra were recorded on a mass spectrometer using alternate-scan positive and negative mode electrospray ionization.

Method A

Method A was conducted on a Sunfire $C_{18}$ column (typically 150 mm×30 mm i.d. 5 μm packing diameter) at ambient temperature. The solvents employed were:
A=0.1% v/v solution of formic acid in water
B=0.1% v/v solution of formic acid in acetonitrile.

Method B

Method B was conducted on an XBridge $C_{18}$ column (typically 100 mm×30 mm i.d. 5 μm packing diameter) at ambient temperature. The solvents employed were:
A=10 mM aqueous ammonium bicarbonate adjusted to pH 10 with ammonia solution.
B=acetonitrile.

Method C

Method C was conducted on a Sunfire $C_{18}$ column (typically 150 mm×30 mm i.d. 5 μm packing diameter) at ambient temperature. The solvents employed were:
A=0.1% v/v solution of trifluoroacetic acid in water
B=0.1% v/v solution of trifluoroacetic acid in acetonitrile.

Abbreviations

The following list provides definitions of certain abbreviations as used herein. It will be appreciated that the list is not exhaustive, but the meaning of those abbreviations not herein below defined will be readily apparent to those skilled in the art.

DCM Dichloromethane
DMF N,1 Dimethylformamide
DMSO Dimethylsulphoxide
THF Tetrahydrofuran
EtOAc Ethyl acetate
MeOH Methanol
EtOH Ethanol
MeCN Acetonitrile
HCl Hydrochloric acid
HPLC High performance liquid chromatography
MDAP Mass Directed Autopreparative HPLC
SPE Solid phase extraction
MeOH Methanol
TBME tert-Butyl methy ether
TFA Trifluoroacetic acid
DIPEA N,N-Diisopropylethylamine Reaction Intermediates Intermediate 1: Ethyl 3-pentanimidamido-1H-pyrrole-2-carboxylate hydrochloride A solution of hydrogen chloride in dioxane (12 mL, 4M, 48 mmol) was added dropwise to a suspension of ethyl 3-amino-1-pyrrole-2-carboxylate hydrochloride (2.04 g, 10.7 mmol) (J. Org. Chem. 1999, 64(22), 8411) in valeronitrile (30 mL). The resultant mixture was heated at 50° C. for 18 hours. The reaction mixture was cooled to room temperature and the solid material collected by filtration and washed with TBME. The title compound was obtained as an off-white solid (2.19 g). A further portion of TBME was added to the filtrate and the mixture re-filtered, the precipitate was washed with TBME and dried to give an additional portion of the title compound (0.275 g).

$^1$H NMR (400 MHz, DMSO-$d_6$) δ ppm 12.22 (br. s., 1H) 10.88 (s, 1H) 9.39 (br. s, 1H) 8.25 (br. s, 1H) 7.09 (t, J=2.9 Hz, 1H) 6.19 (t, J=2.5 Hz, 1H) 4.23 (q, J=7.0 Hz, 2H) 2.52-2.60 (m, 2H) 1.63-1.77 (m, 2H) 1.34-1.47 (m, 2H) 1.27 (t, J=7.2 Hz, 3H) 0.94 (t, J=7.4 Hz, 3H)

Intermediate 2: 2-Butyl-3H-pyrrolo[3,2-d]pyrimidin-4(5H)-one

A solution of sodium hydroxide (1.44 g, 35.9 mmol) in water (7 mL) was added to a solution of ethyl 3-pentanimidamido-1H-pyrrole-2-carboxylate hydrochloride (2.46 g, 8.99 mmol) in ethanol (30 mL). The resultant mixture was heated at reflux for a total of 4 hours. The reaction mixture was cooled to room temperature and the pH adjusted to pH 6.5 with aqueous citric acid. The resultant mixture was extracted with ethyl acetate (2×50 mL). The combined organic phases were washed with saturated aqueous sodium chloride solution, dried ($Na_2SO_4$), filtered and evaporated to give the title compound as a pale brown solid (1.69 g).

LCMS (System B): $t_{RET}$=0.66 min; MH$^+$ 192

Intermediate 3: 2-Butyl-4-chloro-5H-pyrrolo[3,2-d]pyrimidine

Phosphorus oxychloride (20 mL, 21.46 mmol) was added to 2-butyl-3-pyrrolo[3,2-d]pyrimidin-4(5M-one (1.69 g). The resultant mixture was heated at 100° C. After 4 hours the reaction mixture was cooled to room temperature then poured onto ice. The aqueous phase was treated with aqueous sodium hydroxide solution (5M) until the pH was 7. The resultant mixture was extracted with ethyl acetate (2×150 ml). The combined organic phase were washed with brine, dried ($Na_2SO_4$), filtered and evaporated to give the title compound (1.69 g).

LCMS (System B): $t_{RET}$=0.90 min; MH$^+$ 210, 212

Intermediate 4: 2-Butyl-4-chloro-7-iodo-5H-pyrrolo[3,2-d]pyrimidine

N-Iodosuccinimide (2.09 g, 9.29 mmol) was added portionwise to a stirred solution of 2-butyl-4-chloro-5H-pyrrolo[3,2-d]pyrimidine (1.69 g, 8.06 mmol) in THF (35 mL). The resultant mixture was stirred at room temperature for 1 hour. The reaction mixture was diluted with TBME (50 mL) then washed with aqueous sodium thiosulphate solution (50 mL) then saturated aqueous sodium chloride solution (20 mL). The organic phase was dried ($Na_2SO_4$) and evaporated. The sample was dissolved in dichloromethane and purified by chromatography on silica using a gradient of 0-100% dichloromethane-cyclohexane over 30 mins followed by a gradient of 0-100% TBME-cyclohexane followed by 0-20% methanol over 15 minutes. The appropriate fractions were identified by LC-MS then combined and evaporated in vacuo to give the title compound as a yellow solid (2.2 g).

LCMS (System B): $t_{RET}$=1.14 min; MH$^+$ 336, 338

Intermediate 5: 5-((Benzyloxy)methyl)-2-butyl-4-chloro-7-iodo-5H-pyrrolo[3,2-d]pyrimidine Sodium hydride (0.338 g, 60% in oil, 14.08 mmol) was added portionwise to a stirred solution of 4-chloro-7-iodo-2-butyl-5H-pyrrolo[3,2-d]pyrimidine (2.19 g, 6.53 mmol) in DMF (30 mL) cooled in an ice-bath. After 30 minutes benzyl chloromethyl ether (1.13 mL, 1.278 g, 8.16 mmol) was added and the reaction stirred at room temperature. The reaction mixture was quenched with water and the resultant mixture partitioned between ethyl acetate (150 mL) and water (150 mL). The organic phase was washed with water then saturated aqueous sodium chloride solution, dried (Na$_2$SO$_4$), filtered and evaporated. The sample was dissolved in dichloromethane and purified by chromatography on silica (100 g) using a gradient of 0-100% ethyl acetate-cyclohexane over 30 mins. The appropriate fractions were combined and evaporated in vacuo to give the title compound as a yellow oil (2.82 g).

LCMS (System B): $t_{RET}$=1.49 min; MH$^+$ 456, 458

Intermediate 6: 5-((Benzyloxy)methyl)-2-butyl-7-iodo-5H-pyrrolo[3,2-d]pyrimidin-4-amine 5-((Benzyloxy)methyl)-2-butyl-4-chloro-7-iodo-5H-pyrrolo[3,2-d]pyrimidine (1 g, 2.2 mmol) was suspended in 2-propanol (5 mL) and 35% (0.88) ammonia solution (4 mL). The reaction was stirred at 120° C. for 90 minutes in a Biotage Initiator microwave. A further 1 mL of 35% (0.88) ammonia solution was added to the reaction. The reaction was stirred at 120° C. for 90 minutes in a Biotage Initiator microwave. The reaction was evaporated in vacuo to yield a pale yellow oil. The oil was dissolved in the minimum volume of 20% methanol in dichloromethane and purified by chromatography on silica using a gradient of 0-100% ethyl acetate in cyclohexane gradient over 80 minutes. Fractions were combined and evaporated in-vacuo to yield the title compound as a colourless oil (768 mg).

LCMS (System B): $t_{RET}$=1.19 min; MH$^+$ 437

Intermediate 7: 2-(Ethoxymethyl)-3H-pyrrolo[3,2-d]pyrimidin-4(5H)-one

A stirred mixture of 3-amino-2-ethoxycarbonylpyrrole hydrochloride (2.23 g, 11.70 mmol) and 2-ethoxyacetimidamide (2.086 g, 15.21 mmol) in o-xylene (20 mL) was heated to reflux for 23 h. The reaction mixture was concentrated in vacuo to remove most of the o-xylene and give a sample which contained the title compound (3.8 g).

LCMS (System B): $t_{RET}$=0.52 min; MH$^+$ 194

Intermediate 8: 4-Chloro-2-(ethoxymethyl)-5H-pyrrolo[3,2-d]pyrimidine

Phosphorus oxychloride (21.81 mL, 234 mmol) was added to a crude sample of 2-(ethoxymethyl)-3H-pyrrolo[3,2-d]pyrimidin-4(S)-one (2.26 g). The resultant mixture was heated at 100° C. for 3 hours. The reaction mixture was cooled to room temperature then poured carefully onto ice. The mixture was treated with aqueous sodium hydroxide solution (5M) until the pH was 7. The resultant mixture was extracted with ethyl acetate (2×200 mL). The combined organic extracts were washed with brine, dried using an hydrophobic frit and concentrated in vacuo to yield 920 mg of orange oil. The crude product was purified by column chromatography (100 g Si column) using a gradient of 0-100% EtOAc/cyclohexane over 60 minutes. Fractions containing the desired product were combined and concentrated in vacuo to give the title compound as a yellow solid (501 mg).

LCMS (System B): $t_{RET}$=0.67 min; MH$^+$ 212, 214

Intermediate 9: 4-Chloro-2-(ethoxymethyl)-7-iodo-5H-pyrrolo[3,2-d]pyrimidine

Prepared similarly to Intermediate 4 from 4-chloro-2-(ethoxymethyl)-5H-pyrrolo[3,2-d]pyrimidine.

LCMS (System B): $t_{RET}$=0.85 min; MH$^+$ 338, 340

Intermediate 10: 5-((Benzyloxy)methyl)-4-chloro-2-(ethoxymethyl)-7-iodo-5H-pyrrolo[3,2-d]pyrimidine Prepared similarly to Intermediate 5 from 4-chloro-2-(ethoxymethyl)-7-iodo-5H-pyrrolo[3,2-d]pyrimidine.

LCMS (System B): $t_{RET}$=1.27 min; MH$^+$ 458, 460

Intermediate 11: 5-((Benzyloxy)methyl)-2-(ethoxymethyl)-7-iodo-5H-pyrrolo[3,2-d]pyrimidin-4-amine 5-((Benzyloxy)methyl)-2-butyl-4-chloro-7-iodo-6-methyl-5H-pyrrolo[3,2-d]pyrimidine (1.2 g, 2.55 mmol) was suspended in isopropanol (4 mL) and 0.88 ammonia (4.24 mL, 77 mmol) was added. The reaction was stirred and heated at 120° C. for 2 h in a Biotage Initiator microwave. A further portion of 0.88 ammonia (4.24 mL, 77 mmol) was added and the reaction was stirred at 120° C. for 2 h in a Biotage Initiator microwave. A further portion of 0.88 ammonia (4.24 mL, 77 mmol) was added to the reaction and the reaction was stirred at 120° C. for 2 hours in a Biotage Initiator microwave. The reaction was evaporated in vacuo and the crude product was purified by column chromatography (100 g Si column) using a gradient 0-50% EtOAc/cyclohexane over 60 minutes. Appropriate fractions were combined and concentrated in vacuo to give the title compound as a white solid (634 mg).

LCMS (System B): $t_{RET}$=1.24 min; MH$^+$ 451

Intermediate 12: Ethyl 3-(3-methoxypropanimidamido)-1H-pyrrole-2-carboxylate hydrochloride Prepared similarly to Intermediate 1 from ethyl 3-amino-1-pyrrole-2-carboxylate hydrochloride and 3-methoxypropanenitrile.

$^1$H NMR (400 MHz, DMSO-d$_6$) O ppm 12.23 (br. s, 1H) 10.99 (br. s, 1H) 9.48 (br. s, 1H) 8.35 (br. s, 1H) 7.05-7.13 (m, 1H) 6.15-6.20 (m, 1H) 4.23 (q, J=7.0 Hz, 2H) 3.73 (t, J=6.3 Hz, 2H) 3.32 (s, 3H) 2.84 (t, J=6.27 Hz, 2H) 1.27 (t, J=7.2 Hz, 3H)

Intermediate 13: 2-(2-Methoxyethyl)-3H-pyrrolo[3,2-d]pyrimidin-4(S)-one

Prepared similarly to Intermediate 2 from ethyl 3-(3-methoxypropanimidamido)-1H-pyrrole-2-carboxylate hydrochloride.

LCMS (System B): $t_{RET}$=0.48 min; MH$^+$ 194

Intermediate 14: 4-Chloro-2-(2-methoxyethyl)-5H-pyrrolo[3,2-d]pyrimidine

Prepared similarly to Intermediate 3 from 2-(2-methoxyethyl)-3H-pyrrolo[3,2-d]pyrimidin-4(S)-one.
LCMS (System B): $t_{RET}$=0.62 min; MH$^+$ 212, 214

Intermediate 15: 4-Chloro-7-iodo-2-(2-methoxyethyl)-5H-pyrrolo[3,2-d]pyrimidine N-iodosuccinimide (892 mg, 3.97 mmol) was added protionwise to a stirred solution of 4-chloro-2-(2-methoxyethyl)-5H-pyrrolo[3,2-d]pyrimidine (730 mg, 3.45 mmol) in tetrahydrofuran (THF) (30 mL). The resultant mixture was stirred at room temperature for 1 hour. The reaction mixture was diluted with TBME (50 mL) then washed with aqueous sodium thiosulphate solution (50 mL) then saturated aqueous sodium chloride solution (20 mL). The organic phase was dried and filtered using a hydrophobic frit and evaporated to give the title compound (1.17 g).
LCMS (System B): $t_{RET}$=0.81 min; MH$^+$ 338, 340

Intermediate 16: 5-((Benzyloxy)methyl)-4-chloro-7-iodo-2-(2-methoxyethyl)-5H-pyrrolo[3,2-d]pyrimidine To a stirred suspension of sodium hydride 60% wt. on mineral oil (0.180 g, 4.51 mmol) in anhydrous tetrahydrofuran (8 mL) at 0° C. was added a solution of 4-chloro-7-iodo-2-(2-methoxyethyl)-5H-pyrrolo[3,2-d]pyrimidine (1.17 g, 3.47 mmol) in tetrahydrofuran (8 mL) dropwise over 5 minutes. The resultant mixture was stirred at 0° C. for 15 minutes before the addition of a solution of benzylchloromethyl ether (0.504 mL, 3.64 mmol) in tetrahydrofuran (5 mL) dropwise over 5 min. The reaction was stirred for two hours. The reaction was partitioned between ethyl acetate (200 mL) and water (200 mL). The organic layer was separated and washed with brine (200 mL), dried, filtered and concentrated in vacuo to give the crude compound (1.57 g). The sample was dissolved in dichloromethane and purified by chromatography on silica (70 g) using a gradient of 0-50% ethyl acetate-cyclohexane over 60 minutes. The appropriate fractions were combined and evaporated in vacuo to give the title compound as a solid (985 mg).
LCMS (System B): $t_{RET}$=1.23 min; MH$^+$ 458, 460

Intermediate 17: 5-((Benzyloxy)methyl)-7-iodo-2-(2-methoxyethyl)-5H-pyrrolo[3,2-d]pyrimidin-4-amine To solid 5-((benzyloxy)methyl)-4-chloro-7-iodo-2-(2-methoxyethyl)-5H-pyrrolo[3,2-d]pyrimidine (555 mg, 1.213 mmol) was added isopropanol (3 mL) and ammonia 880 (0.75 mL, 13.56 mmol). The reaction vessel was sealed and heated in a Biotage Initiator using initial absorption setting very high to 150° C. for 1 h. To the reaction was added further ammonia 880 (0.75 mL, 13.56 mmol) and the reaction vessel was sealed and heated in a Biotage Initiator using initial absorption setting very high to 150° C. for 1 h. Reaction was concentrated in vacuo and the mixture was partitioned between ethyl acetate (50 mL) and water (50 mL) and separated. The aqueous layer was back extracted with ethyl acetate (25 mL) and the combined organics were washed with brine (25 mL), dried using a hydrophobic frit and concentrated in vacuo to give a brown gum. The sample was dissolved in dichloromethane and purified by chromatography on silica (Si) (50 g) using a 0-100% ethyl acetate-dichloromethane gradient over 40 mins. The appropriate fractions were combined and evaporated in vacuo to give the title compound as a yellow gum (349 mg).
(System B): $t_{RET}$=0.99 min; MH$^+$ 439

Intermediate 18: Ethyl 5-methyl-3-pentanimidamido-1H-pyrrole-2-carboxylate hydrochloride Hydrogen chloride in dioxane (4M, 308 mL, 1.2 mol) was added dropwise to ethyl 3-amino-5-methyl-1-pyrrole-2-carboxylate (38.3 g, 228 mmol) (J. Med. Chem. 2008, 51, 68) in valeronitrile (383 mL). The resultant mixture was heated at 50° C. overnight. An additional portion of acid (160 mL, 0.64 mol) was added and the mixture heated at 55° C. overnight. The reaction mixture was cooled to room temperature, filtered and the filtrate evaporated. The residue was slurried in TBME (1200 ml) for 30 minutes then the solid was filtered and washed with TMBE and dried. The title compound was obtained as a brown solid (58.9 g).
$^1$H NMR (400 MHz, DMSO-d$_6$) δ ppm includes 11.90 (br. s, 1H) 11.09 (s, 1H) 9.52 (br. s, 1H) 8.14 (br. s, 1H) 5.82 (br. s, 1H) 4.12 (q, J=7.1 Hz, 2H) 3.48 (br. s., 1H) 2.14 (s, 3H) 1.51-1.70 (m, 2H) 1.05-1.40 (m, 6H) 0.84 (t, J=7.1 Hz, 3H)

Intermediate 19: 2-Butyl-6-methyl-3-pyrrolo[3,2-d]pyrimidin-4(5H)-one

Aqueous sodium hydroxide solution (6M, 138 mL) was added dropwise to a solution of ethyl 5-methyl-3-pentanimidamido-1-pyrrole-2-carboxylate (58.9 g, 0.2 mol) in ethanol (550 mL) cooled in an ice-bath. The reaction mixture was heated at reflux for 2.5 hours then cooled to room temperature. Water (700 mL) was added and the pH adjusted to pH 6.5 using aqueous citric acid (2M). The resultant mixture was stirred for 45 minutes then filtered and the solid material washed with water. The material was dried in a vacuum oven at 50° C. to give the title compound.
$^1$H NMR (400 MHz, DMSO-d$_6$) δ ppm includes 11.60 (s, 1H) 11.53 (s, 1H) 5.91 (s, 1H) 2.33-2.50 (m, 2H) 2.19 (s, 3H) 1.45-1.60 (m, 2H) 1.10-1.26 (m, 2H) 0.70-0.84 (m, 3H)

Intermediate 20: 2-Butyl-4-chloro-6-methyl-5H-pyrrolo[3,2-d]pyrimidine

Phosphorus oxychloride (42.8 mL, 70.4 g, 0.459 mol) was added dropwise to a solution of 2-butyl-6-methyl-3-pyrrolo[3,2-d]pyrimidin-4(5H)-one (37.5 g, 0.183 mol) in acetonitrile (750 mL) under an atmosphere of nitrogen. The reaction mixture was heated at reflux overnight. After cooling to room temperature an additional portion of phosphorus oxychloride (42.8 mL, 70.4 g, 0.459 mol) was added dropwise and heating continued for a further 3.5 hours. The reaction was cooled to room temperature again and a further portion of phosphorus oxychloride (42.8 mL, 70.4 g, 0.459 mol) was added dropwise and heating continued for 3 hours. The reaction mixture was allowed to stand at room temperature overnight then heated at reflux for 3.5 hours. The reaction mixture was cooled then concentrated. The residue was cooled in an ice-bath and ice-cold water (650 mL) was added carefully. The pH was adjusted to 8 using aqueous potassium hydroxide solution and then mixture stirred for 45 minutes. The mixture was partitioned between dichloromethane (1000 mL) and water (1000 mL). The aqueous layer and solid material was re-extracted with dichloromethane (2×500 mL). The combined organic layers were dried (Na$_2$SO$_4$) and filtered through a plug of neutral alumina. The filtrate was concentrated to a yellow oil, a seed crystal and hexane were added. The solid material was filtered, washed with hexane and dried to give the title compound as an off-white solid (15.5 g).

LCMS (System A): $t_{RET}$=0.81 min; MH+ 224/226

Intermediate 21: 2-Butyl-4-chloro-7-iodo-6-methyl-5H-pyrrolo[3,2-d]pyrimidine Prepared similarly to Intermediate 4 from 2-butyl-4-chloro-6-methyl-5H-pyrrolo[3,2-d]pyrimidine.

LCMS (System B): $t_{RET}$=1.20 min; MH+ 350, 352

Intermediate 22: 5-((Benzyloxy)methyl)-2-butyl-4-chloro-7-iodo-6-methyl-5H-pyrrolo[3,2-d]pyrimidine Prepared similarly to Intermediate 5 from 2-butyl-4-chloro-7-iodo-6-methyl-5H-pyrrolo[3,2-d]pyrimidine.

LCMS (System B): $t_{RET}$=1.54 min; MH+ 470, 472

Intermediate 23: 5-((Benzyloxy)methyl)-2-butyl-7-iodo-6-methyl-5H-pyrrolo[3,2-d]pyrimidin-4-amine Prepared similarly to Intermediate 6 from 5-((benzyloxy)methyl)-2-butyl-4-chloro-7-iodo-6-methyl-5H-pyrrolo[3,2-d]pyrimidine.

LCMS (System B): $t_{RET}$=1.24 min; MH+ 451

Intermediate 24: 2-Butyl-4-chloro-7-iodo-5-((2-(trimethylsilyl)ethoxy)methyl)-5H-pyrrolo[3,2-d]pyrimidine To a stirred suspension of sodium hydride 60% wt. on mineral oil (0.248 g, 6.20 mmol) in anhydrous THF (20 mL) at 0° C. was added a solution of 2-butyl-4-chloro-7-iodo-5H-pyrrolo[3,2-d]pyrimidine (1.3 g, 3.87 mmol) in THF (20 mL) dropwise over 5 min. The resultant mixture was stirred at 0° C. for 15 minutes before the addition of a solution of (2-(chloromethoxy)ethyl)trimethylsilane (0.720 mL, 4.07 mmol) in THF (10 mL) dropwise over 5 min. The reaction was stirred for two hours then quenched with water. The reaction was partitioned between ethyl acetate (100 mL) and water (100 mL). The organic was separated and washed with brine (100 mL), dried, filtered and concentrated in vacuo to give the title compound (1.86 g) as a red oil.

LCMS (System B): $t_{RET}$=1.65 min; MH+ 466

Intermediate 25: 2-Butyl-7-iodo-5-((2-(trimethylsilyl)ethoxy)methyl)-5H-pyrrolo[3,2-d]pyrimidin-4-amine Prepared similarly to Intermediate 17 from 2-butyl-4-chloro-7-iodo-5-((2-(trimethylsilyl)ethoxy)methyl)-5H-pyrrolo[3,2-d]pyrimidine.

LCMS (System B): $t_{RET}$=1.38 min; MH+ 447

Intermediate 26: 1-(Hex-5-yn-1-yl)piperidine

A solution of 6-chlorohex-1-yne (5 mL, 41.3 mmol), piperidine (4.08 mL, 41.3 mmol) and sodium hydrogen carbonate (4.16 g, 49.5 mmol) in DMF (50 mL) was refluxed for 16 hr. The reaction was concentrated in vacuo and the residue partitioned between ether (150 mL) and water (150 mL). The organic was separated and the aqueous back extracted with diethyl ether (50 mL). The combined organics were washed with brine (150 mL), dried (MgSO$_4$), filtered and concentrated in vacuo to give a crude sample of the title compound (3.74 g). Oxalic acid (2.161 g, 24 mmol) was added to the crude product. The resultant solid was recrystallised from ethanol, collected by filtration and dried in vacuo to give 1-(hex-5-yn-1-yl)piperidine oxalic acid salt (4.66 g). The solid was partitioned between diethyl ether (150 mL) and saturated aqueous sodium bicarbonate (150 mL). The organic was separated and dried (MgSO$_4$) filtered and concentrated in vacuo to give the title compound as a yellow oil (1.93 g).

$^1$H NMR (400 MHz, CDCl$_3$) δ ppm 2.31-2.52 (m, 6H) 2.18-2.26 (m, 2H) 1.92-1.96 (m, 1H) 1.40-1.72 (m, 10H)

Intermediate 27: 1-(Pent-4-yn-1-yl)piperidine

A mixture of piperidine (11.6 mL, 117 mmol), 5-chloro-1-pentyne (13.8 mL, 129 mmol) and sodium hydrogen carbonate (11.84 g, 141 mmol) in DMF (100 mL) under argon was heated at 80° C. for 18 hours. The reaction mixture was diluted with ice cold water then extracted with ethyl acetate. The phases were separated and the organic phase washed with water (100 mL), saturated brine (25 mL), dried over sodium sulphate and evaporated in vacuo to give the crude product as an orange liquid. The crude product was purified by chromatography on silica eluting with 10% methanol in DCM. The title compound was obtained as a red liquid (5.05 g).

$^1$H NMR (400 MHz, CDCl$_3$) δ ppm 2.30-2.50 (m, 6H) 2.15-2.30 (m, 2H) 1.90-1.99 (m, 1H), 1.65-1.78 (m, 2H), 1.50-1.63 (m, 4H) 1.33-1.48 (m, 2H)

Intermediate 28: 5-((Benzyloxy)methyl)-2-butyl-7-(6-(piperidin-1-yl)hex-1-yn-1-yl)-5H-Pyrrolo[3,2-d]pyrimidin-4-amine To a degassed solution of 5-((benzyloxy)methyl)-2-butyl-7-iodo-5H-pyrrolo[3,2-d]pyrimidin-4-amine (217 mg, 0.497 mmol) in anhydrous N,N-dimethylformamide (3.5 mL) under a nitrogen atmosphere at room temperature was added copper(I) iodide (19 mg, 0.1 mmol), bis(triphenylphosphine)palladium(II)dichloride (38.4 mg, 0.055 mmol) and finally triethylamine (0.124 mL, 0.895 mmol). The mixture was stirred at room temperature under a nitrogen atmosphere for 10 minutes and then a solution of 1-(hex-5-yn-1-yl)piperidine (132 mg, 0.796 mmol) in anhydrous degassed N,N-dimethylformamide (0.5 mL) was added. The reaction mixture was stirred at 55° C. for 40 minutes. The reaction was evaporated in vacuo to yield a dark red oil. The oil was partitioned between water and dichloromethane. The organic layer was separated and the aqueous back extracted with dichloromethane. The combined organic extracts were passed through a hydrophobic frit and evaporated in vacuo to yield a dark red oil. The oil was dissolved in MeOH:DMSO (1:1) (5×1 mL) purified by MDAP (Method B). Appropriate fractions were combined and evaporated in vacuo to yield the title compound as a yellow oil (161 mg).

LCMS (System B): $t_{RET}$=1.26 min; MH+ 474

Intermediate 29: 2-Butyl-7-(6-(piperidin-1-yl)hex-1-yn-1-yl)-5-((2-(trimethylsilyl)ethoxy)methyl)-5H-pyrrolo[3,2-d]pyrimidin-4-amine To a degassed stirred solution of 2-butyl-7-iodo-5-((2-(trimethylsilyl)ethoxy)methyl)-5H-pyrrolo[3,2-d]pyrimidin-4-amine (400 mg, 0.896 mmol), copper (I) iodide (34 mg, 0.179 mmol) and bis(triphenylphosphine)palladium(II)dichloride (63 mg, 0.090 mmol) in anhydrous N,N-dimethylformamide (6 mL) was added a solution of 1-(hex-5-yn- 1-yl)piperidine (193 mg, 1.165 mmol) and triethylamine (0.186 mL, 1.344 mmol) in anhydrous N,N-dimethylformamide (3 mL) dropwise over 5 minutes. The reaction was stirred at ambient temperature under a nitrogen atmosphere for 20 hours. The reaction was concentrated in vacuo and the residue partitioned between ethyl acetate (50 mL) and water (50 mL). The organic phase was separated and the aqueous back extracted with ethyl acetate (50 mL). The combined organics were washed with brine (50 mL), dried (MgSO$_4$), filtered and concentrated in vacuo to give an orange gum. The sample was dissolved in dichloromethane and purified on a silica (Si) cartridge (50 g) using a 0-10% methanol-dichloromethane gradient over 40 minutes. The appropriate fractions were combined and evaporated in vacuo to give the title compound as a yellow foam (87 mg).

LCMS (System A): $t_{RET}$=0.71 min; MH$^+$ 484

Intermediate 30: 2-Butyl-7-(6-(piperidin-1-yl) hexyl)-5-((2-(trimethylsilyl)ethoxy)methyl)-5H-pyrrolo[3,2-d]pyrimidin-4-amine A solution of 2-butyl-7-(6-(piperidin-1-yl)hex-1-yn-1-yl)-5-((2-(trimethylsilyl)ethoxy)methyl)-5H-pyrrolo[3,2-d]pyrimidin-4-amine (87 mg, 0.180 mmol) in ethanol (8 mL) and acetic acid (1 mL) was hydrogenated using the H-cube (settings: 60° C., Full H$_2$, 1 mL/min flow rate) and 10% Pd/C CatCart 30 as the catalyst. The reaction was concentrated in vacuo and the residue partitioned between DCM (20 mL) and 2N aqueous sodium hydroxide (20 mL). The organic layer was separated and dried using a hydrophobic frit before concentration in vacuo to give the title compound (50 mg).

LCMS (System A): $t_{RET}$=0.86 min; MH$^+$ 488

Intermediate 31: 5-((Benzyloxy)methyl)-2-butyl-7-(5-(piperidin-1-yl)pent-1-yn-1-yl)-5H-pyrrolo[3,2-d] pyrimidin-4-amine To a degassed solution of 5-((benzyloxy)methyl)-2-butyl-7-iodo-5H-pyrrolo[3,2-d]pyrimidin-4-amine (175 mg, 0.401 mmol) in anhydrous N,N-dimethylformamide (3 mL) under nitrogen atmosphere at room temperature was added copper (I) iodide (15 mg, 0.079 mmol), bis(triphenylphosphine) palladium(II)dichloride (31 mg, 0.044 mmol) and finally triethylamine (0.1 mL, 0.722 mmol). The mixture was stirred at room temperature under nitrogen atmosphere for 10 minutes and then a solution of 1-(pent-4-yn-1-yl)piperidine (97 mg, 0.642 mmol) in anhydrous degassed N,N-dimethylformamide (0.5 mL) was added. The reaction mixture was stirred at 55° C. for 40 minutes. The reaction was evaporated in vacuo to yield a dark yellow oil. The oil was partitioned between water and dichloromethane. The organic layer was separated and the aqueous back extracted with dichloromethane. The combined organic extracts were passed through a hydrophobic frit and evaporated in vacuo to yield a dark yellow oil. The oil was dissolved in MeOH:DMSO (1:1) (4×1 mL) and purified by MDAP (Method B). Appropriate fractions were combined and evaporated in vacuo to yield the title compound as a pale yellow solid (73 mg).

LCMS (System B): $t_{RET}$=1.26 min; MH$^+$ 460

Intermediate 32: 5-((Benzyloxy)methyl)-2-butyl-7-(4-(Piperidin-1-yl)but-1-yn-1-yl)-5H-pyrrolo[3,2-d] pyrimidin-4-amine Prepared similarly to Intermediate 26 from 5-((benzyloxy)methyl)-2-butyl-7-iodo-5H-pyrrolo[3,2-d]pyrimidin-4-amine and 1-(but-3-yn-1-yl)piperidine (Eur J. Med. Chem. 2009, 44(10), 4098)

LCMS (System B): $t_{RET}$=1.11 min; MH$^+$ 446.

Intermediate 33: 5-((Benzyloxy)methyl)-2-(ethoxymethyl)-7-(6-(piperidin-1-yl)hex-1-yn-1-yl)-5H-pyrrolo[3,2-d]pyrimidin-4-amine Prepared similarly to Intermediate 26 from 5-((benzyloxy)methyl)-4-chloro-7-iodo-2-(2-methoxyethyl)-5H-pyrrolo[3,2-d]pyrimidine and 1-(hex-5-yn-1-yl)piperidine.

LCMS (System B): $t_{RET}$=1.16 min; MH$^+$ 476

Intermediate 34: 5-((Benzyloxy)methyl)-2-(2-methoxyethyl)-7-(6-(piperidin-1-yl)hex-1-yn-1-yl)-5H-pyrrolo[3,2-d]pyrimidin-4-amine To a degassed solution of 5-((benzyloxy)methyl)-7-iodo-2-(2-methoxyethyl)-5H-pyrrolo[3,2-d]pyrimidin-4-amine (264 mg, 0.602 mmol) in anhydrous N,N-dimethylformamide (7 mL) under nitrogen atmosphere at room temperature was added copper (I) iodide (22.94 mg, 0.120 mmol), bis(triphenylphosphine)palladium(II)dichloride (42.3 mg, 0.060 mmol) and finally triethylamine (0.125 mL, 0.904 mmol). The mixture was stirred at room temperature under a nitrogen atmosphere for 10 minutes and then a solution of 1-(hex-5-yn-1-yl)piperidine (129 mg, 0.783 mmol) in anhydrous degassed N,N-dimethylformamide (1 mL) was added. The reaction mixture was stirred at room temperature for 16 hours. 1-(Hex-5-yn-1-yl)piperidine (129 mg, 0.783 mmol) was added and the mixture was stirred at room temperature for 1 hour. The reaction was evaporated in vacuo to yield a brown oil. The oil was partitioned between water (25 mL) and dichloromethane (25 mL). The organic layer was separated and the aqueous back extracted with dichloromethane (20 mL). The combined organic extracts were passed through a hydrophobic frit and evaporated in vacuo to yield an orange oil. The sample was dissolved in dichloromethane and purified by chromatography on silica (50 g) using a gradient of 0-100% ethyl acetate in cyclohexane over 60 minutes. The appropriate fractions were combined and evaporated in vacuo to give the title compound as an oil (102 mg).

LCMS (System B): $t_{RET}$=1.08 min; MH$^+$ 476

Intermediate 35: 5-((Benzyloxy)methyl)-2-butyl-6-methyl-7-(6-(piperidin-1-yl)hex-1-yn-1-yl)-5H-pyrrolo[3,2-d]pyrimidin-4-amine To a degassed solution of 5-((benzyloxy)methyl)-2-butyl-7-iodo-6-methyl-5H-pyrrolo[3,2-d]pyrimidin-4-amine (215 mg, 0.477 mmol) in anhydrous N,N-dimethylformamide (4 mL) under a nitrogen atmosphere at room temperature was added copper (I) iodide (19 mg, 0.100 mmol), bis(triphenylphosphine)palladium(II)dichloride (36.9 mg, 0.053 mmol) and finally triethylamine (0.119 mL, 0.859 mmol). The mixture was stirred at room temperature under a nitrogen atmosphere for 10 minutes and then a solution of 1-(hex-5-yn-1-yl)piperidine (126 mg, 0.764 mmol) in anhydrous degassed N,N-dimethylformamide (2 mL) was added. The reaction mixture was stirred at 55° C. for 1.5 hours. Copper (I) iodide (19 mg, 0.100 mmol), bis(triphenylphosphine) palladium(II)dichloride (36.9 mg, 0.053 mmol) and 1-(hex-5-yn-1-yl)piperidine (126 mg, 0.764 mmol) were added and the reaction mixture was left to stir at 55° C. for 1 hour. The reaction was evaporated in vacuo to yield a dark red oil. The oil was partitioned between water and dichloromethane. The organic layer was separated and the aqueous back extracted with dichloromethane. The combined organic extracts were passed through a hydrophobic frit and evaporated in vacuo to yield a dark red oil. The crude product was purified by MDAP (Method B). Fractions which contained product were concentrated to give the title compound as a yellow oil (134 mg).

LCMS (System B): $t_{RET}$=1.33 min; MH$^+$ 488

Intermediate 36: 5-((Benzyloxy)methyl)-2-butyl-6-methyl-7-(4-(Piperidin-1-yl)but-1-yn-1-yl)-5H-pyrrolo[3,2-d]pyrimidin-4-amine Prepared similarly to Intermediate 28 from 5-((benzyloxy)methyl)-2-butyl-7-iodo-6-methyl-5H-pyrrolo[3,2-d]pyrimidin-4-amine and 1-(but-3-yn-1-yl)piperidine.

LCMS (System B): $t_{RET}$=1.29 min; MH$^+$ 460

Intermediate 37: 5-((Benzyloxy)methyl)-2-butyl-7-(5-chloropent-1-yn-1-yl)-5H-pyrrolo[3,2-d]pyrimidin-4-amine To a degassed suspension of 5-((benzyloxy)methyl)-2-butyl-7-iodo-5H-pyrrolo[3,2-d]pyrimidin-4-amine (2.768 g, 6.34 mmol), copper (I) iodide (0.242 g, 1.269 mmol), and bis(triphenylphosphine)palladium(II)dichloride (0.445 g, 0.634 mmol) in anhydrous N,N-dimethylformamide (40 mL) was added a solution of 5-chloropent-1-yne (0.781 g, 7.61 mmol) and triethylamine (1.231 mL, 8.88 mmol) in anhydrous N,N-dimethylformamide (20 mL) dropwise over 2 minutes. The reaction was stirred at ambient temperature for 17 hours. The reaction was concentrated in vacuo and the resultant brown oil partitioned between water (500 mL) and ethyl acetate (500 mL). The organic phase was separated and the aqueous back extracted with ethyl acetate (250 mL). The combined organics were washed with brine (400 mL), dried (MgSO$_4$), filtered and concentrated in vacuo. The sample was dissolved in dichloromethane and purified by chromatography on silica (Si) (2×100 g) using a 0-100% ethyl acetate-cyclohexane gradient over 60 minutes. The appropriate fractions were combined and evaporated in vacuo to give a red oil. The sample was dissolved in dichloromethane and purified by chromatography on silica using a 0-100% ethyl acetate-cyclohexane gradient over 80 minutes. The appropriate fractions were combined and evaporated in vacuo to give the title compound as a yellow solid. (1.13 g)

LCMS (System B): $t_{RET}$=1.29 min; MH$^+$ 411, 413

Intermediate 38: 5-((Benzyloxy)methyl)-2-butyl-7-(5-(pyrrolidin-1-yl)pent-1-yn-1-yl)-5H-pyrrolo[3,2-d]pyrimidin-4-amine To a stirred solution of 5-((benzyloxy)methyl)-2-butyl-7-(5-chloropent-1-yn-1-yl)-5H-pyrrolo[3,2-d]pyrimidin-4-amine (150 mg, 0.365 mmol) and triethylamine (0.061 mL, 0.438 mmol) in anhydrous acetonitrile (3 mL) at ambient temperature was added pyrrolidine (0.033 mL, 0.402 mmol) in one charge. The reaction was stirred at ambient temperature for 1.5 hours then at 60° C. for 2.5 hours. Heating at 80° C. was continued for 16 h. Further pyrrolidine (0.033 mL, 0.402 mmol) and triethylamine (0.061 mL, 0.438 mmol) were added and heating at 80° C. continued for 10 hours. The reaction was concentrated in vacuo and the residue partitioned between dichloromethane (10 mL) and water (10 mL). The organic phase was separated and dried (hydrophobic frit) before concentration in vacuo. The sample was dissolved in dichloromethane and purified by chromatography on an aminopropyl (NH$_2$) silica using a 0-100% ethyl acetate-dichloromethane gradient over 20 minutes. The appropriate fractions were combined and evaporated in vacuo to give the title compound as an off-white solid (95 mg).

LCMS (System B): $t_{RET}$=1.23 min; MH$^+$ 446

Intermediate 39: 6-(4-Amino-5-((benzyloxy)methyl)-2-butyl-5H-pyrrolo[3,2-d]pyrimidin-7-yl)hex-5-yn-1-ol To solid 5-((benzyloxy)methyl)-2-butyl-7-iodo-5H-pyrrolo[3,2-d]pyrimidin-4-amine (1.2 g, 2.75 mmol) in N,N-dimethylformamide (20 mL) was added bis(triphenylphosphine)palladium(II)dichloride (0.193 g, 0.275 mmol) and copper(I) iodide (0.105 g, 0.550 mmol). The solution was stirred and degassed with nitrogen for 5 minutes then the reaction mixture placed under a nitrogen atmosphere. A solution of hex-5-yn-1-ol (0.405 g, 4.13 mmol) and triethylamine (0.575 mL, 4.13 mmol) in N,N-dimethylformamide (5 mL) was added dropwise over 5 minutes. The reaction mixture was stirred at ambient temperature for 24 h. Additional hex-5-yn-1-ol (0.1 g, 1.02 mmol) and triethylamine (0.15 mL, 1.08 mmol) in N,N-dimethylformamide (3 mL) was added dropwise over 5 minutes and the reaction mixture stirred at ambient temperature for a further 5 hours. The reaction mixture was concentrated in vacuo at 60° C. and the residue partitioned between ethyl acetate (100 mL) and water (100 mL). The organic layer was separated and the aqueous layer back extracted with ethyl acetate (3×50 mL). The combined organic phases were washed with brine, dried (hydrophobic frit) and concentrated in vacuo to a viscous brown oil (2.00 g). The sample was dissolved in dichloromethane and purified by chromatography on aminopropyl silica (110 g) using a gradient of 0-100% ethyl acetate-cyclohexane followed by a gradient of 0-20% methanol-ethyl acetate over 40 minutes. The appropriate fractions were combined, evaporated in vacuo, then azeotroped with diethyl ether and dried to give a sticky off-white solid (699 mg). The sample was loaded in dichloromethane and re-purified by chromatography on silica (Si) (50 g) using a 0-100% ethyl acetate-dichloromethane gradient over 40 mins. The appropriate fractions were combined and evaporated in vacuo to give the title compound as a white solid (505 mg).

LCMS (System B): $t_{RET}$=1.04 min; MH$^+$ 407

Intermediate 40: 6-(4-Amino-5-((benzyloxy)methyl)-2-butyl-5H-pyrrolo[3,2-d]pyrimidin-7-yl)hex-5-ynal A mixture of 6-(4-amino-5-((benzyloxy)methyl)-2-butyl-5H-pyrrolo[3,2-d]pyrimidin-7-yl)hex-5-yn-1-ol (505 mg, 1.242 mmol), N-methylmorpholine N-oxide (218 mg, 1.863 mmol), powdered 4 Å molecular sieves and tetrapropylammonium perruthenate (21.83 mg, 0.062 mmol) was placed under nitrogen and anhydrous dichloromethane (18 mL) and anhydrous acetonitrile (2 mL) added. The reaction mixture was stirred at ambient temperature for 2 hours. The reaction mixture was concentrated in vacuo at 60° C. The residue was dissolved in dichloromethane, filtered through a pad of celite and concentrated in vacuo to give a as a black gum (678 mg). The sample was dissolved in dichloromethane and purified by chromatography on a silica cartridge (50 g) using a 0-10% methanol-dichloromethane gradient over 40 mins. The appropriate fractions were combined and evaporated in vacuo to give a yellow gum with black discolouration (399 mg). The sample was dissolved in dichloromethane and re-purified on silica (50 g) using a 0-10% methanol-dichloromethane gradient over 40 minutes. The appropriate fractions were combined and evaporated in vacuo to give the title compound as a yellow gum (227 mg).

LCMS (System B): $t_{RET}$=1.11 min; MH$^+$ 405

Intermediate 41: 5-((Benzyloxy)methyl)-2-butyl-7-(6-(pyrrolidin-1-yl)hex-1-yn-1-yl)-5H-pyrrolo[3,2-d]pyrimidin-4-amine A suspension of 6-(4-amino-5-((benzyloxy)methyl)-2-butyl-5H-pyrrolo[3,2-d]pyrimidin-7-yl)hex-5-ynal (117 mg, 0.289 mmol) and 4 Å molecular sieves in anhydrous dichloromethane (7 mL) was placed under nitrogen and pyrrolidine (0.048 mL, 0.578 mmol) added. The reaction mixture was stirred at ambient temperature for 1 minute then sodium triacetoxyborohydride (61.3 mg, 0.289 mmol) added and the reaction stirred for a further 1 hour. Additional pyrrolidine (0.025 mL, 0.301 mmol) and sodium triacetoxyborohydride (80 mg, 0.377 mmol) were added and the reaction mixture stirred for a further 30 minutes. The reaction mixture was filtered through celite and the cake washed with DCM. The solvent was removed in vacuo and the residue redissolved in DCM (20 mL). The organic layer was washed with saturated sodium hydrogen carbonate solution (20 mL), the layers separated and the aqueous layer back-extracted with DCM (20 mL). The combined organic phases were dried through a hydrophobic frit and concentrated in vacuo to give a yellow gum. The sample was dissolved in dichloromethane and purified on aminopropyl silica (10 g) using a 0-100% ethyl acetate-cyclohexane followed 0-20% methanol gradient over 40 minutes. The appropriate fractions were combined and evaporated in vacuo to give the title compound as a white solid (55 mg).

LCMS (System B): $t_{RET}$=1.17 min; MH$^+$ 460

Intermediate 42:
2-Pentyl-3H-pyrrolo[3,2-d]pyrimidin-4(5H)-one

A suspension of ethyl 3-amino-1H-pyrrole-2-carboxylate, hydrochloride (3 g, 15.74 mmol), hexanenitrile (30 g, 309 mmol) and 4M hydrochloric acid in dioxane (20 mL, 80 mmol) was stirred at 50° C. for 20 hours. The reaction mixture was allowed to cool to ambient temperature, upon cooling a precipitate formed. To the reaction was added further 4M hydrochloric acid in dioxane (10 mL) and the reaction mixture was heated at 50° C. for a further 4 hours. The reaction mixture was allowed to cool to ambient temperature then diluted with TBME (300 mL) and the resultant suspension filtered. The solid cake was washed with TBME (150 mL) and diethyl ether (150 mL) and dried in vacuo to give a biege solid (4.4 g). The solid was dissolved in ethanol (45 mL) and treated with a solution of sodium hydroxide (2.52 g, 62.9 mmol) in water (10 mL) then the mixture was heated to 80° C. for 4 hours. The reaction solvent was removed in vacuo. The residue was suspended in water (200 mL) and the pH adjusted to 4 with solid citric acid, and extracted with ethyl acetate (2×200 mL). The combined organic extracts were dried (MgSO$_4$), filtered and concentrated in vacuo to give a sticky biege solid. The solid was triturated with diethyl ether and the resultant suspension filtered and dried in vacuo to give the title compound as an off white solid (1.884 g).

LCMS (System B): $t_{RET}$=0.72 min; MH$^+$ 206

Intermediate 43:
4-Chloro-2-pentyl-5H-pyrrolo[3,2-d]pyrimidine

A stirred suspension of 2-pentyl-3-pyrrolo[3,2-d]pyrimidin-4(5H)-one (1.88 g, 9.16 mmol) in phosphorus (V) oxychloride (20 mL, 215 mmol) was heated to 100° C. for 3 hours. The reaction mixture was concentrated in vacuo and azeotroped with toluene. The resultant gum was dissolved in DCM (100 mL) and washed with water (100 mL) and was dried (hydrophobic frit) before being concentrated in vacuo to give a brown solid. The sample was dissolved in dichloromethane and purified by chromatography on a silica cartridge (50 g) using a 0-25% MeOH:TBME gradient over 40 minutes. The appropriate fractions were combined and evaporated in vacuo to give a brown solid, this was triturated with diethyl ether (ca. 100 mL), the resultant suspension was filtered and the solid dried in vacuo to give the title compound as a pale brown solid (1.04 g).

LCMS (System B): $t_{RET}$=0.99 min; MH$^+$ 224, 226

Intermediate 44: 4-Chloro-7-iodo-2-pentyl-5H-pyrrolo[3,2-d]pyrimidine

Prepared similarly to Intermediate 15 from 4-chloro-2-pentyl-5H-pyrrolo[3,2-d]pyrimidine LCMS (System B): $t_{RET}$=1.21 min; MH$^+$ 350, 352

Intermediate 45: 5-((Benzyloxy)methyl)-4-chloro-7-iodo-2-pentyl-5H-pyrrolo[3,2-d]pyrimidine To a stirred slurry of sodium hydride 60% wt. on mineral oil (0.167 g, 4.17 mmol) in anhydrous THF (15 mL) at 0° C. under a nitrogen atmosphere was added a solution of 4-chloro-7-iodo-2-pentyl-5H-pyrrolo[3,2-d]pyrimidine (1.268 g, 3.63 mmol) in anhydrous THF (10 mL) dropwise over 10 minutes. The reaction was stirred at 0° C. for a further 30 minutes before addition of a solution of ((chloromethoxy)methyl)benzene (0.653 g, 4.17 mmol) in anhydrous THF (10 mL) dropwise over 10 minutes. The reaction was then allowed to warm to ambient temperature and stirred for a further 60 minutes. To the reaction was added further sodium hydride 60% wt. on mineral oil (30 mg, 0.75 mmol) and stirring at ambient temperature was continued for 16 hours. The reaction was partitioned between water (120 mL) and ethyl acetate (120 mL). The organic phase was separated and the aqueous layer back extracted with ethyl acetate (50 mL). The combine organic extracts were washed with brine (100 mL), dried (MgSO$_4$), filtered and concentrated in vacuo to give an orange oil. The sample was dissolved in dichloromethane and purified by chromatography on a silica cartridge (100 g) using a 0-50% ethyl acetate-cyclohexane gradient over 60 mins. The appropriate fractions were combined and evaporated in vacuo to give the title compound as a yellow oil (1.478 g).

LCMS (System B): $t_{RET}$=1.51 min; MH$^+$ 470, 472

Intermediate 46: 5-((Benzyloxy)methyl)-7-iodo-2-pentyl-5H-pyrrolo[3,2-d]pyrimidin-4-amine Prepared similarly to Intermediate 17 from 5-((benzyloxy)methyl)-4-chloro-7-iodo-2-pentyl-5H-pyrrolo[3,2-d]pyrimidine LCMS (System B): $t_{RET}$=1.26 min; MH$^+$ 451

Intermediate 47: 5-((Benzyloxy)methyl)-2-pentyl-7-(6-(piperidin-1-yl)hex-1-yn-1-yl)-5H-Pyrrolo[3,2-d]pyrimidin-4-amine Prepared similarly to Intermediate 29 from 5-((benzyloxy)methyl)-7-iodo-2-pentyl-5H-pyrrolo[3,2-d]pyrimidin-4-amine and 1-(hex-5-yn-1-yl)piperidine LCMS (System B): $t_{RET}$=1.30 min; MH$^+$ 488

Intermediate 48: 7-(5-(Azepan-1-yl)pent-1-yn-1-yl)-5-((benzyloxy)methyl)-2-butyl-5H-pyrrolo[3,2-d]pyrimidin-4-amine Prepared similarly to Intermediate 38 from 5-((benzyloxy)methyl)-2-butyl-7-(5-chloropent-1-yn-1-yl)-5H-pyrrolo[3,2-d]pyrimidin-4-amine and azepane.
LCMS (System B): $t_{RET}$=1.27 min; MH$^+$ 474

Intermediate 49: 4-(4-Amino-5-((benzyloxy)methyl)-2-butyl-6-methyl-5H-pyrrolo[3,2-d]pyrimidin-7-yl)but-3-yn-1-ol Prepared similarly to Intermediate 39 from 5-((benzyloxy)methyl)-2-(ethoxymethyl)-7-iodo-5H-pyrrolo[3,2-d]pyrimidin-4-amine and but-3-yn-1-ol.
LCMS (System B): $t_{RET}$=1.07 min; MH$^+$ 393

Intermediate 50: 4-(4-Amino-5-((benzyloxy)methyl)-2-butyl-6-methyl-5H-pyrrolo[3,2-d]pyrimidin-7-yl)butan-1-ol A filtered solution of 4-(4-amino-5-((benzyloxy)methyl)-2-butyl-6-methyl-5H-pyrrolo[3,2-d]pyrimidin-7-yl)but-3-yn-1-ol (853 mg, 2.173 mmol) in ethanol (80 mL) was hydrogenated using the H-cube (settings: 20° C., Full H$_2$, 1 mL/min flow rate) and a 10% Pd/C CatCart 30 as the catalyst. The solution was re-hydrogenated using the H-cube (settings: 20° C., Full H$_2$, 1 mL/min flow rate) and a new 10% Pd/C CatCart 30 as the catalyst. The reaction mixture was concentrated in vacuo and the residue was dissolved in dichloromethane and purified by chromatography on a silica cartridge (100 g) using a 0-25% methanol-dichloromethane gradient over 60 minutes. The appropriate fractions were combined and evaporated in vacuo to give the title compound as a off-white solid (543 mg).
LCMS (System B): $t_{RET}$=0.83 min; MH$^+$ 397

Intermediate 51: 4-(4-Amino-5-((benzyloxy)methyl)-2-butyl-6-methyl-5H-pyrrolo[3,2-d]pyrimidin-7-yl)butanal To a stirred suspension of 4-(4-amino-5-((benzyloxy)methyl)-2-butyl-6-methyl-5H-pyrrolo[3,2-d]pyrimidin-7-yl)butan-1-ol (230 mg, 0.580 mmol), 4-methylmorpholine N-oxide (82 mg, 0.696 mmol) and powdered 4 Å molecular sieves in a mixture of anhydrous dichloromethane (10 mL) and anhydrous acetonitrile (1 mL) at ambient temperature was added tetrapropylammonium perruthenate (22 mg, 0.063 mmol), and the reaction was stirred at ambient temperature for 2 h. The reaction mixture was concentrated in vacuo (water bath 20° C.). The resultant residue was slurried with DCM (10 mL) and filtered through a pad of celite. The resultant solution was concentrated in vacuo and re-dissolved in dichloromethane and purified by chromatography on a silica cartridge (20 g) using a 0-10% methanol-dichloromethane gradient over 40 mins. The appropriate fractions were combined and evaporated in vacuo to give the title compound as a yellow gum (114 mg).
LCMS (System B): $t_{RET}$=1.13 min; MH$^+$ 395

Intermediate 52: 7-(4-(Azepan-1-yl)butyl)-5-((benzyloxy)methyl)-2-butyl-6-methyl-5H-pyrrolo[3,2-d]pyrimidin-4-amine A suspension of 4-(4-amino-5-((benzyloxy)methyl)-2-butyl-6-methyl-5H-pyrrolo[3,2-d]pyrimidin-7-yl)butanal (68 mg, 0.172 mmol) and 4 Å molecular sieves in anhydrous dichloromethane (5 mL) was placed under nitrogen and azepane (0.039 mL, 0.345 mmol) added. The reaction mixture was stirred at ambient temperature for 1 minute then sodium triacetoxyborohydride (73.1 mg, 0.345 mmol) added and the reaction stirred for a further 1 hour. The reaction mixture was filtered through celite and the cake washed with DCM then Methanol. The solvent was removed in vacuo and the residue redissolved in DCM (50 mL). The organic layer was washed with saturated sodium hydrogen carbonate solution (50 mL), the layers separated and the aqueous layer back-extracted with DCM (25 mL) then 3:1 CHCl$_3$:IPA (40 mL). The combined organics were dried with MgSO$_4$, filtered and concentrated in vacuo to give an off-white gum (180 mg). The sample was loaded in dichloromethane and purified by chromatography on aminopropyl cartridge (11 g) using a 0-25% methanol-dichloromethane gradient over 30 minutes. The appropriate fractions were combined and evaporated in vacuo to give the title compound as a white solid (42 mg).
LCMS (System B): $t_{RET}$=1.36 min; MH$^+$ 478

Intermediate 53: 5-((Benzyloxy)methyl)-2-butyl-7-(6-chlorohex-1-yn-1-yl)-6-methyl-5H-pyrrolo[3,2-d]pyrimidin-4-amine Prepared similarly to Intermediate 28 from 5-((benzyloxy)methyl)-2-butyl-7-iodo-6-methyl-5H-pyrrolo[3,2-d]pyrimidin-4-amine and 6-chlorohex-1-yne.
LCMS (System B): $t_{RET}$=1.33 min; MH$^+$ 439, 441

Intermediate 54: 5-((Benzyloxy)methyl)-2-butyl-6-methyl-7-(6-(pyrrolidin-1-yl)hex-1-yn-1-yl)-5H-pyrrolo[3,2-d]pyrimidin-4-amine To a stirred solution of 5-((benzyloxy)methyl)-2-butyl-7-(6-chlorohex-1-yn-1-yl)-6-methyl-5H-pyrrolo[3,2-d]pyrimidin-4-amine (160 mg, 0.364 mmol) and triethylamine (0.152 mL, 1.093 mmol) in acetonitrile (4 mL) was added pyrrolidine (0.090 mL, 1.093 mmol). The reaction was stirred at 80° C. for 18 hours. Additional pyrrolidine (0.045 mL, 0.547 mmol) and triethylamine (0.075 mL, 0.539 mmol) were added to the reaction mixture which was stirred at 80° C. for a further 2 hours. The reaction mixture was concentrated in vacuo at 60° C. and the residue partitioned between DCM (25 mL) and water (25 mL). The organic layer was separated and the aqueous layer back-extracted with DCM (2×25 mL). The combined organic phases were dried through a hydrophobic frit and concentrated in vacuo to give an orange-brown solid (184 mg). The sample was loaded in dichloromethane and purified by chromatography on an aminopropyl cartridge (NH$_2$) (10 g) using a 0-50% ethyl acetate-dichloromethane gradient over 40 minutes. The appropriate fractions were combined and evaporated in vacuo to the title compound as a pale yellow gum (157 mg).
LCMS (System B): $t_{RET}$=1.18 min; MH$^+$ 474

Intermediate 55: 6-(4-Amino-5-((benzyloxy)methyl)-2-butyl-6-methyl-5H-pyrrolo[3,2-d]pyrimidin-7-yl)hex-5-yn-1-ol To solid 5-((benzyloxy)methyl)-2-butyl-7-iodo-6-methyl-5H-pyrrolo[3,2-d]pyrimidin-4-amine (500 mg, 1.110 mmol) in N,N-dimethylformamide (8 mL) was added bis(triphenylphosphine)palladium(II)dichloride (78 mg, 0.111 mmol) and copper(I) iodide (42.3 mg, 0.222 mmol). The solution was stirred and degassed with nitrogen for 5 minutes then the reaction mixture placed under a nitrogen atmosphere. A solution of hex-5-yn-1-ol (163 mg, 1.665 mmol) and triethylamine (0.232 mL, 1.665 mmol) in N,N-dimethylformamide (2 mL) was added dropwise over 5 minutes. The reaction mixture was stirred at 50° C. for 6 hours. Additional bis(triphenylphosphine)palladium(II)dichloride (40 mg, 0.0569 mmol) and copper(I) iodide (20 mg, 0.105 mmol) was added to the reaction mixture which was degassed with nitrogen for 5 mins then placed under a nitrogen atmosphere. A solution of hex-5-yn-1-ol (80 mg, 0.817 mmol) and triethylamine (0.100 mL, 0.711 mmol) in N,N-dimethylformamide (2 mL) was added dropwise over 5 minutes. The reaction mixture was stirred at 50° C. for a further 2.5 hours then allowed to cool to ambient temperature and stirred for 20 hours (for convenience) and heated to 50° C. for a final 2 hours. The reaction mixture was concentrated in vacuo at 60° C. and the residue separated between ethyl acetate (100 mL) and water (100 mL). The organic layer was separated and the aqueous layer back extracted with ethyl acetate (2×50 mL) and 3:1 CHCl$_3$: IPA (40 mL). The combined organics were dried through a hydrophobic frit and concentrated in vacuo to give a viscous brown oil (1.06 g). The sample was loaded in dichloromethane and purified by chromatography on an aminopropyl cartridge (NH$_2$) (70 g) using a 0-100% ethyl acetate-dichloromethane gradient over 60 minutes. The appropriate fractions were combined, evaporated in vacuo and azeotroped with diethyl ether to give the title compound as an off-white solid (195 mg).

LCMS (System B): $t_{RET}$=1.07 min; MH$^+$ 421.

Intermediate 56: 6-(4-Amino-5-((benzyloxy) methyl)-2-butyl-6-methyl-5H-pyrrolo[3,2-d]pyrimidin-7-yl)hex-5-ynal Prepared similarly to Intermediate 40 from 6-(4-amino-5-((benzyloxy)methyl)-2-butyl-6-methyl-5H-pyrrolo[3,2-d]pyrimidin-7-yl)hex-5-yn-1-ol LCMS (System B): $t_{RET}$=1.16 min; MH$^+$ 419

Intermediate 57: 7-(6-(Azetidin-1-yl)hex-1-yn-1-yl)-5-((benzyloxy)methyl)-2-butyl-6-methyl-5H-pyrrolo[3,2-d]pyrimidin-4-amine Prepared similarly to Intermediate 41 from 6-(4-amino-5-((benzyloxy)methyl)-2-butyl-6-methyl-5H-pyrrolo[3,2-d]pyrimidin-7-yl)hex-5-ynal and azetidine.

LCMS (System B): $t_{RET}$=1.17 min; MH$^+$ 460

Intermediate 58: 5-((Benzyloxy)methyl)-2-butyl-7-(5-chloropent-1-yn-1-yl)-6-methyl-5H-pyrrolo[3,2-d]pyrimidin-4-amine Prepared similarly to Intermediate 28 5-((benzyloxy) methyl)-2-butyl-7-iodo-6-methyl-5H-pyrrolo[3,2-d]pyrimidin-4-amine and 6-chloropent-1-yne.

LCMS (System B): $t_{RET}$=1.29 min; MH$^+$ 425, 427

Intermediate 59: 5-((Benzyloxy)methyl)-2-butyl-6-methyl-7-(5-(pyrrolidin-1-yl)pent-1-yn-1-yl)-5H-pyrrolo[3,2-d]pyrimidin-4-amine Prepared similarly to Intermediate 54 from 5-((benzyloxy)methyl)-2-butyl-7-(5-chloropent-1-yn-1-yl)-6-methyl-5H-pyrrolo[3,2-d]pyrimidin-4-amine and pyrrolidine.

LCMS (System B): $t_{RET}$=1.17 min; MH$^+$ 460

Intermediate 60: 5-(4-Amino-5-((benzyloxy) methyl)-2-butyl-5H-pyrrolo[3,2-d]pyrimidin-7-yl) pent-4-yn-1-ol Prepared similarly to Intermediate 39 from 5-((benzyloxy)methyl)-2-butyl-7-iodo-5H-pyrrolo[3,2-d]pyrimidin-4-amine and pent-4-yn-1-ol.

LCMS (System B): $t_{RET}$=1.05 min; MH$^+$ 393

Intermediate 61: 5-(4-Amino-5-((benzyloxy) methyl)-2-butyl-5H-pyrrolo[3,2-d]pyrimidin-7-yl) pent-4-ynal Prepared similarly to Intermediate 40 from 5-(4-amino-5-((benzyloxy)methyl)-2-butyl-5H-pyrrolo[3,2-d]pyrimidin-7-yl)pent-4-yn-1-ol.

LCMS (System B): $t_{RET}$=1.08 min; MH$^+$ 391

Intermediate 62: 7-(5-(Azetidin-1-yl)pent-1-yn-1-yl)-5-((benzyloxy)methyl)-2-butyl-5H-pyrrolo[3,2-d]pyrimidin-4-amine Prepared similarly to Intermediate 41 from 5-(4-amino-5-((benzyloxy)methyl)-2-butyl-5H-pyrrolo[3,2-d]pyrimidin-7-yl)pent-4-ynal and azetidine.

LCMS (System B): $t_{RET}$=1.17 min; MH$^+$ 432

Intermediate 63: 5-(4-Amino-5-((benzyloxy) methyl)-2-butyl-6-methyl-5H-pyrrolo[3,2-d]pyrimidin-7-yl)bent-4-yn-1-ol Prepared similarly to Intermediate 55 from 5-((benzyloxy)methyl)-2-butyl-7-iodo-6-methyl-5H-pyrrolo[3,2-d]pyrimidin-4-amine and pent-4-yn-1-ol.

LCMS (System B): $t_{RET}$=1.03 min; MH$^+$ 407

Intermediate 64: 5-(4-Amino-5-((benzyloxy) methyl)-2-butyl-6-methyl-5H-pyrrolo[3,2-d]pyrimidin-7-yl)pent-4-ynal Prepared similarly to Intermediate 40 from 5-(4-amino-5-((benzyloxy)methyl)-2-butyl-6-methyl-5H-pyrrolo[3,2-d]pyrimidin-7-yl)pent-4-yn-1-ol.

LCMS (System B): $t_{RET}$=1.09 min; MH$^+$ 405

Intermediate 65: 7-(5-(Azetidin-1-yl)pent-1-yn-1-yl)-5-((benzyloxy)methyl)-2-butyl-6-methyl-5H-pyrrolo[3,2-d]pyrimidin-4-amine Prepared similarly to Intermediate 41 from 5-(4-amino-5-((benzyloxy)methyl)-2-butyl-6-methyl-5H-pyrrolo[3,2-d]pyrimidin-7-yl)pent-4-ynal and azetidine.

LCMS (System B): $t_{RET}$=1.14 min; MH$^+$ 446

Intermediate 66: 5-((Benzyloxy)methyl)-2-butyl-6-methyl-7-(4-(pyrrolidin-1-yl)butyl)-5H-Pyrrolo[3,2-d]pyrimidin-4-amine Prepared similarly to Intermediate 52 from 4-(4-amino-5-((benzyloxy)methyl)-2-butyl-6-methyl-5H-pyrrolo[3,2-d]pyrimidin-7-yl)butanal and pyrrolidine.

LCMS (System B): $t_{RET}$=1.19 min; MH$^+$ 450

Intermediate 67: 5-((Benzyloxy)methyl)-2-butyl-7-(5-(4,4-difluoropiperidin-1-yl)pent-1-yn-1-yl)-5H-pyrrolo[3,2-d]pyrimidin-4-amine To a stirred suspension of 5-((benzyloxy)methyl)-2-butyl-7-(5-chloropent-1-yn-1-yl)-5H-pyrrolo[3,2-d]pyrimidin-4- amine (150 mg, 0.365 mmol) and 4,4-difluoropiperidine hydrochloride (86 mg, 0.548 mmol) in anhydrous acetonitrile (3 mL) at ambient temperature was added triethylamine (0.153 mL, 1.095 mmol) in one charge. The reaction was sealed and heated in a Biotage Initiator microwave (absorption setting normal) to 150° C. for 30 minutes. The reaction was re-sealed and heated in a Biotage Initiator microwave (absorption setting normal) to 170° C. for 60 minutes. To the reaction was added further 4,4-difluoropiperidine hydrochloride (86 mg, 0.548 mmol) and triethylamine (0.153 mL, 1.095 mmol) and the reaction was re-sealed and heated in a Biotage Initiator microwave (absorption setting normal) to 150° C. for 60 minutes. The reaction was concentrated in vacuo and partitioned between DCM (10 mL) and water (10 mL). The organic was separated and dried (hydrophobic frit) and concentrated in vacuo before being dissolved in DCM and purified by chromatography on aminopropyl functionalised silica (11 g) using a 0-100% ethyl acetate:DCM gradient over 20 minutes. The material eluted at the solvent front and so did not collect. The waste stream was concentrated in vacuo to give the title compound (77 mg).

LCMS (System A): $t_{RET}$=0.62 min; MH$^+$ 496

Intermediate 68: 5-((Benzyloxy)methyl)-2-butyl-7-(5-(4-fluoropiperidin-1-yl)pent-1-yn-1-yl)-5H-pyrrolo[3,2-d]pyrimidin-4-amine Prepared similarly to Intermediate 54 from 5-((benzyloxy)methyl)-2-butyl-7-(5-chloropent-1-yn-1-yl)-5H-pyrrolo[3,2-d]pyrimidin-4-amine and 4-fluoropiperidine hydrochloride.

LCMS (System B): $t_{RET}$=1.24 min; MH$^+$ 478

Intermediate 69: 5-((Benzyloxy)methyl)-7-(5-chloropent-1-yn-1-yl)-2-(2-methoxyethyl)-5H-pyrrolo[3,2-d]pyrimidin-4-amine Prepared similarly to Intermediate 37 from 5-((benzyloxy)methyl)-7-iodo-2-(2-methoxyethyl)-5H-pyrrolo[3,2-d]pyrimidin-4-amine and 5-chloropent-1-yne.

LCMS (System B): $t_{RET}$=1.11 min; MH$^+$ 413, 415

Intermediate 70: 5-((Benzyloxy)methyl)-7-(5-(4-fluoropiperidin-1-yl)pent-1-yn-1-yl)-2-(2-methoxyethyl)-5H-pyrrolo[3,2-d]pyrimidin-4-amine Prepared similarly to Intermediate 54 from 5-((benzyloxy)methyl)-7-(5-chloropent-1-yn-1-yl)-2-(2-methoxyethyl)-5H-pyrrolo[3,2-d]pyrimidin-4-amine and 4-fluoropiperidine hydrochloride.

LCMS (System B): $t_{RET}$=1.07 min; MH$^+$ 480

Intermediate 71: 1-(5-(4-Amino-5-((benzyloxy)methyl)-2-butyl-5H-pyrrolo[3,2-d]pyrimidin-7-yl)pent-4-yn-1-yl)piperidin-4-ol Prepared similarly to Intermediate 54 from 5-((benzyloxy)methyl)-2-butyl-7-(5-chloropent-1-yn-1-yl)-5H-pyrrolo[3,2-d]pyrimidin-4-amine and piperidin-4-ol.

LCMS (System B): $t_{RET}$=1.04 min; MH$^+$ 476

Intermediate 72: (R)-5-((Benzyloxy)methyl)-2-butyl-7-(5-(3-fluoropyrrolidin-1-yl)pent-1-yn-1-yl)-5H-pyrrolo[3,2-d]pyrimidin-4-amine Prepared similarly to Intermediate 54 from 5-((benzyloxy)methyl)-2-butyl-7-(5-chloropent-1-yn-1-yl)-5H-pyrrolo[3,2-d]pyrimidin-4-amine and (R)-(−)-3-fluoropyrrolidine hydrochloride.

LCMS (System B): $t_{RET}$=1.18 min; MH$^+$ 464

Intermediate 73: (S)-5-((Benzyloxy)methyl)-2-butyl-7-(5-(3-fluoropyrrolidin-1-yl)pent-1-yn-1-yl)-5H-pyrrolo[3,2-d]pyrimidin-4-amine Prepared similarly to Intermediate 54 from 5-((benzyloxy)methyl)-2-butyl-7-(5-chloropent-1-yn-1-yl)-5H-pyrrolo[3,2-d]pyrimidin-4-amine and (S)-(−)-3-fluoropyrrolidine hydrochloride.

LCMS (System B): $t_{RET}$=1.18 min; MH$^+$ 464

Intermediate 74: (R)-5-((Benzyloxy)methyl)-7-(5-(3-fluoropyrrolidin-1-yl)pent-1-yn-1-yl)-2-(2-methoxyethyl)-5H-pyrrolo[3,2-d]pyrimidin-4-amine Prepared similarly to Intermediate 54 from 5-((benzyloxy)methyl)-7-(5-chloropent-1-yn-1-yl)-2-(2-methoxyethyl)-5H-pyrrolo[3,2-d]pyrimidin-4-amine and (R)-(−)-3-fluoropyrrolidine hydrochloride.

LCMS (System B): $t_{RET}$=1.02 min; MH$^+$ 466

Intermediate 75: (S)-5-((Benzyloxy)methyl)-7-(5-(3-fluoropyrrolidin-1-yl)pent-1-yn-1-yl)-2-(2-methoxyethyl)-5H-pyrrolo[3,2-d]pyrimidin-4-amine Prepared similarly to Intermediate 54 from 5-((benzyloxy)methyl)-7-(5-chloropent-1-yn-1-yl)-2-(2-methoxyethyl)-5H-pyrrolo[3,2-d]pyrimidin-4-amine and (S)-(−)-3-fluoropyrrolidine hydrochloride.

LCMS (System B): $t_{RET}$=1.02 min; MH$^+$ 466

Intermediate 76: (S)-1-(5-(4-Amino-5-((benzyloxy)methyl)-2-butyl-5H-pyrrolo[3,2-d]pyrimidin-7-yl)bent-4-yn-1-yl)pyrrolidin-3-ol Prepared similarly to Intermediate 41 from 5-(4-amino-5-((benzyloxy)methyl)-2-butyl-5H-pyrrolo[3,2-d]pyrimidin-7-yl)pent-4-ynal and (S)-3-pyrrolidinol.

LCMS (System B): $t_{RET}$=1.04 min; MH$^+$ 462

Intermediate 77: 1-(5-(4-Amino-5-((benzyloxy)methyl)-2-butyl-5H-pyrrolo[3,2-d]pyrimidin-7-yl)pent-4-yn-1-yl)azetidin-3-ol A mixture of 5-(4-amino-5-((benzyloxy)methyl)-2-butyl-5H-pyrrolo[3,2-d]pyrimidin-7-yl)pent-4-ynal (150 mg, 0.384 mmol), 3-hydroxyazetidine hydrochloride (84 mg, 0.768 mmol) and triethylamine (0.107 mL, 0.768 mmol) in anhydrous dichloromethane (DCM) (2.5 mL) was stirred at room temperature under nitrogen for 1 hour. Molecular sieves were added to the reaction mixture. Sodium triacetoxyborohydride (163 mg, 0.768 mmol) was added and the reaction was left to stir at room temperature for 1 hour. The reaction mixture was filtered and water was added. The phases were separated, the aqueous phase were neutralised with aqueous 2M NaOH solution and extracted with EtOAc. The organic layers were combined and concentrated in vacuo.

The residue was dissolved in 1:1 MeOH:DMSO (1 mL) and purified by MDAP (Method A). Fractions which contain the product were concentrated to give the title compound as an orange oil (68 mg).

LCMS (System B): $t_{RET}$=0.99 min; MH$^+$ 448

Intermediate 78: 5-((Benzyloxy)methyl)-2-butyl-7-(6-chlorohex-1-yn-1-yl)-5H-pyrrolo[3,2-d]pyrimidin-4-amine Prepared similarly to Intermediate 37 from 5-((benzyloxy)methyl)-2-butyl-7-iodo-5H-pyrrolo[3,2-d]pyrimidin-4-amine and 6-chlorohex-1-yne. The product was purified by in two stages, firstly by chromatography on silica using a 0-50% ethyl acetate-dichloromethane gradient over 60 mins followed by purification on an aminopropyl (NH2) cartridge (110 g) using a 0-100% ethyl acetate-cyclohexane gradient over 40 mins.
LCMS (System B): $t_{RET}$=1.29 min; MH$^+$ 425, 427

Intermediate 79: 5-((Benzyloxy)methyl)-7-(6-chlorohex-1-yn-1-yl)-2-(2-methoxyethyl)-5H-pyrrolo[3,2-d]pyrimidin-4-amine Prepared similarly to Intermediate 37 from 5-((benzyloxy)methyl)-7-iodo-2-(2-methoxyethyl)-5H-pyrrolo[3,2-d]pyrimidin-4-amine and 6-chlorohex-1-yne.
LCMS (System B): $t_{RET}$=1.14 min; MH$^+$ 427, 429

Intermediate 80: 7-(6-(Azepan-1-yl)hex-1-yn-1-yl)-5-((benzyloxy)methyl)-2-(2-methoxyethyl)-5H-pyrrolo[3,2-d]pyrimidin-4-amine Prepared similarly to Intermediate 54 from 5-((benzyloxy)methyl)-7-(6-chlorohex-1-yn-1-yl)-2-(2-methoxyethyl)-5H-pyrrolo[3,2-d]pyrimidin-4-amine and azepane but with heating at 80° C. for 72 hours and purification on silica using a 0-25% methanol-DCM gradient over 40 mins.
LCMS (System B): $t_{RET}$=1.10 min; MH$^+$ 490

Intermediate 81: 5-((Benzyloxy)methyl)-2-butyl-7-(6-(4-fluoropiperidin-1-yl)hex-1-yn-1-yl)-5H-pyrrolo[3,2-d]pyrimidin-4-amine To a suspension 5-((benzyloxy)methyl)-2-butyl-7-(6-chlorohex-1-yn-1-yl)-5H-pyrrolo[3,2-d]pyrimidin-4-amine (435 mg, 1.024 mmol) and 4-fluoropiperidine hydrochloride (367 mg, 2.63 mmol) in acetonitrile (7 mL) was added triethylamine (0.856 mL, 6.14 mmol) at ambient temperature. The reaction mixture was stirred at 60° C. under nitrogen for 88 h. The reaction mixture was evaporated in vacuo to give an brown solid which was partitioned between ethyl acetate (50 mL) and water (50 mL). The organic layer was separated, washed with brine (50 mL), dried using a hydrophobic frit and concentrated in vacuo to give a brown oil. This crude product was purified by sequential chromatography on aminopropyl (NH2) cartridge using firstly a 0-50% ethyl acetate-cyclohexane gradient and then a 0-100% tert-butyl methyl ether (TBME)-cyclohexane gradient and finally a 0-10% methanol-dichloromethane gradient. Final purification by MDAP (Method B) gave the title compound as an off-white solid (50 mg).
LCMS (System B): $t_{RET}$=1.24 min; MH$^+$ 492

Intermediate 82: (R)-5-((Benzyloxy)methyl)-2-butyl-7-(6-(3-fluoropyrrolidin-1-yl)hex-1-yn-1-yl)-5H-pyrrolo[3,2-d]pyrimidin-4-amine Prepared similarly to Intermediate 54 from 5-((benzyloxy)methyl)-2-butyl-7-(6-chlorohex-1-yn-1-yl)-5H-pyrrolo[3,2-d]pyrimidin-4-amine and (R)(−)3-fluoropyrrolidine hydrochloride but with heating at 60° C. for 88 hours and purification on aminopropyl (NH2) cartridge using a 0-50% ethyl acetate-cyclohexane gradient.
LCMS (System B): $t_{RET}$=1.20 min; MH$^+$ 478

Intermediate 83: (S)-5-((Benzyloxy)methyl)-2-butyl-7-(6-(3-fluoropyrrolidin-1-yl)hex-1-yn-1-yl)-5H-pyrrolo[3,2-d]pyrimidin-4-amine Prepared similarly to Intermediate 82 from 5-((benzyloxy)methyl)-2-butyl-7-(6-chlorohex-1-yn-1-yl)-5H-pyrrolo[3,2-d]pyrimidin-4-amine and (S)(+)3-fluoropyrrolidine hydrochloride
LCMS (System B): $t_{RET}$=1.20 min; MH$^+$ 478

Intermediate 84: (S)-5-((Benzyloxy)methyl)-2-butyl-7-(5-(2-methylpyrrolidin-1-yl)pent-1-yn-1-yl)-5H-pyrrolo[3,2-d]pyrimidin-4-amine To a stirred solution of 5-((benzyloxy)methyl)-2-butyl-7-(5-chloropent-1-yn-1-yl)-5H-pyrrolo[3,2-d]pyrimidin-4-amine (200 mg, 0.487 mmol) in acetonitrile (4 mL) was added triethylamine (0.204 mL, 1.460 mmol) and (S)-2-methylpyrrolidine (0.149 mL, 1.460 mmol). The resultant mixture was heated at 60° C. for 72 h when more (S)-2-methylpyrrolidine (0.05 mL, 0.49 mmol) and triethylamine (0.068 mL, 0.49 mmol) were added and the reaction heated to 80° C. for 5 h. The reaction mixture was concentrated in vacuo and the residue partitioned between DCM (20 mL) and water (20 mL). The organic layer was separated and dried (hydrophobic frit) before concentration in vacuo to give a red oil. This material was dissolved in dichloromethane and purified on an aminopropyl functionalised silica cartridge (11 g) using a 0-50% ethyl acetate-cyclohexane gradient over 40 mins. The appropriate fractions were combined and evaporated in vacuo to give the title compound as a colourless oil which solidified (142 mg).
LCMS (System B): $t_{RET}$=1.15 min; MH$^+$ 460

Intermediate 85: (R)-5-((Benzyloxy)methyl)-2-butyl-7-(5-(2-methylpyrrolidin-1-yl)bent-1-yn-1-yl)-5H-pyrrolo[3,2-d]pyrimidin-4-amine Prepared similarly to Intermediate 84 from 5-((benzyloxy)methyl)-2-butyl-7-(5-chloropent-1-yn-1-yl)-5H-pyrrolo[3,2-d]pyrimidin-4-amine and (R)-2-methylpyrrolidine.
LCMS (System B): $t_{RET}$=1.12 min; MH$^+$ 460

Intermediate 86: 5-((Benzyloxy)methyl)-2-butyl-7-(5-(3-methylazetidin-1-yl)pent-1-yn-1-yl)-5H-pyrrolo[3,2-d]pyrimidin-4-amine To a stirred suspension of 5-(4-amino-5-((benzyloxy)methyl)-2-butyl-5H-pyrrolo[3,2-d]pyrimidin-7-yl)pent-4-ynal (90 mg, 0.230 mmol) and 4 Å molecular sieves in anhydrous DCM (4 mL) under nitrogen was added a solution of 3-methylazetidine hydrochloride (28 mg, 0.260 mmol) and triethylamine (0.04 mL, 0.287 mmol) in anhydrous DCM (1 mL). The reaction mixture was stirred at ambient temperature for 1 min before addition of sodium triacetoxyborohydride (98 mg, 0.461 mmol) and stirring was continued at ambient temperature for 4 h. The reaction mixture was diluted with DCM (15 mL) and filtered through celite. The filtrate was washed with saturated aqueous sodium bicarbonate (20 mL), dried (hydrophobic frit) and concentrated in vacuo to give a brown oil. This material was dissolved in dichloromethane and purified on an aminopropyl functionalised silica cartridge (11 g) using a 0-100% ethyl acetate-cyclohexane gradient over 30 mins. The appropriate fractions were combined and evaporated in vacuo to give the title compound as a colourless oil (33 mg).

LCMS (System B): $t_{RET}$=1.19 min; MH+ 446

Intermediate 87: 5-((Benzyloxy)methyl)-2-butyl-7-(5-(3-fluoroazetidin-1-yl)pent-1-yn-1-yl)-5H-pyrrolo[3,2-d]pyrimidin-4-amine Prepared similarly to Intermediate 86 from 5-(4-amino-5-((benzyloxy)methyl)-2-butyl-51 pyrrolo[3,2-d]pyrimidin-7-yl)pent-4-ynal and 3-fluoroazetidine hydrochloride LCMS (System B): $t_{RET}$=1.12 min; MH+ 450

Intermediate 88: 5-((Benzyloxy)methyl)-2-butyl-6-methyl-7-(6-(pyrrolidin-1-yl)hex-1-yn-1-yl)-5H-pyrrolo[3,2-d]pyrimidin-4-amine To a stirred solution of 5-((benzyloxy)methyl)-2-butyl-7-(6-chlorohex-1-yn-1-yl)-6-methyl-5H-pyrrolo[3,2-d]pyrimidin-4-amine (160 mg, 0.364 mmol) and triethylamine (0.152 mL, 1.093 mmol) in acetonitrile (4 mL) was added pyrrolidine (0.090 mL, 1.093 mmol). The reaction was stirred at 80° C. for 18 h when more pyrrolidine (0.045 mL, 0.547 mmol) and triethylamine (0.075 mL, 0.539 mmol) were added and the mixture was stirred at 80° C. for a further 2 h. The reaction mixture was then concentrated in vacuo at 60° C. and the residue partitioned between DCM (25 mL) and water (25 mL). The organic layer was separated and the aqueous layer back-extracted with DCM (2×25 mL). The combined organic phases were dried through a hydrophobic frit and concentrated in vacuo to give an orange-brown solid. This material was loaded in dichloromethane and purified on aminopropyl (NH2) cartridge (10 g) using a 0-50% ethyl acetate-DCM gradient over 40 mins. The appropriate fractions were combined and evaporated in vacuo to give the title compound as a pale yellow gum (157 mg).

LCMS (System B): $t_{RET}$=1.18 min; MH+ 474

Intermediate 89: 5-((Benzyloxy)methyl)-2-butyl-7-(5-(4-fluoropiperidin-1-yl)pent-1-yn-1-yl)-6-methyl-5H-pyrrolo[3,2-d]pyrimidin-4-amine To a stirred solution of 5-((benzyloxy)methyl)-2-butyl-7-(5-chloropent-1-yn-1-yl)-6-methyl-5H-pyrrolo[3,2-d]pyrimidin-4-amine (140 mg, 0.329 mmol) in acetonitrile (3 mL) was added triethylamine (0.276 mL, 1.977 mmol) and 4-fluoropiperidine hydrochloride (138 mg, 0.988 mmol). The resultant mixture was heated at 60° C. for 18 h when more 4-fluoropiperidine hydrochloride (50 mg, 0.36 mmol) and triethylamine (0.1 mL, 0.72 mmol) were added and heating at 60° C. continued for 20 h. More triethylamine (0.1 mL, 0.72 mmol) was added and the mixture heated to 80° C. for a further 4 h. The reaction mixture was concentrated in vacuo and the residue partitioned between DCM (20 mL) and water (20 mL). The organic layer was separated and dried (hydrophobic frit) before concentration in vacuo to a red oil. This material was dissolved in dichloromethane and purified on an aminopropyl functionalised silica cartridge (11 g) using a 0-100% ethyl acetate-cyclohexane gradient over 30 mins. The appropriate fractions were combined and evaporated in vacuo to give the title compound as a colourless gum (85 mg).

LCMS (System B): $t_{RET}$=1.24 min; MH+ 492

Intermediate 90: (S)-5-((Benzyloxy)methyl)-2-butyl-7-(5-(3-fluoropyrrolidin-1-yl)pent-1-yn-1-yl)-6-methyl-5H-pyrrolo[3,2-d]pyrimidin-4-amine To a stirred solution of 5-((benzyloxy)methyl)-2-butyl-7-(5-chloropent-1-yn-1-yl)-6-methyl-5H-pyrrolo[3,2-d]pyrimidin-4-amine (334 mg, 0.786 mmol) in DMF (6 mL) was added triethylamine (0.657 mL, 4.72 mmol) and (S)-3-fluoropyrrolidine hydrochloride (296 mg, 2.358 mmol). The resultant mixture was heated at 60° C. for 52 h and then concentrated in vacuo. The residue was partitioned between DCM (40 mL) and water (40 mL) and the organic layer was separated. The aqueous layer was re-extracted with DCM (50 mL) and the organic extracts were combined, dried (hydrophobic frit) and concentrated in vacuo to give a yellow oil (534 mg). This crude product was dissolved in dichloromethane and loaded onto an aminopropyl (NH2) cartridge (50 g) and eluted with a 0-100% ethyl acetate-cyclohexane gradient over 60 min. The appropriate fractions were combined and evaporated in vacuo to give the title compound as a colourless oil (265.7 mg).

LCMS (System B): $t_{RET}$=1.19 min; MH+ 478

Intermediate 91: (k)-5-((Benzyloxy)methyl)-2-butyl-7-(5-(3-fluoropyrrolidin-1-yl)pent-1-yn-1-yl)-6-methyl-5H-pyrrolo[3,2-d]pyrimidin-4-amine Prepared similarly to Intermediate 89 from 5-((benzyloxy)methyl)-2-butyl-7-(5-chloropent-1-yn-1-yl)-6-methyl-5H-pyrrolo[3,2-d]pyrimidin-4-amine and (R)-3-fluoropyrrolidine hydrochloride.

LCMS (System B): $t_{RET}$=1.20 min; MH+ 478

Intermediate 92: 5-((Benzyloxy)methyl)-2-butyl-7-(5-(3-fluoroazetidin-1-yl)pent-1-yn-1-yl)-6-methyl-5H-pyrrolo[3,2-d]pyrimidin-4-amine Prepared similarly to Intermediate 86 from 5-(4-amino-5-((benzyloxy)methyl)-2-butyl-6-methyl-5H-pyrrolo[3,2-d]pyrimidin-7-yl)pent-4-ynal and 3-fluoroazetidine hydrochloride LCMS (System B): $t_{RET}$=1.16 min; MH+ 464

Intermediate 93: 5-((Benzyloxy)methyl)-2-(2-methoxyethyl)-7-(5-(pyrrolidin-1-yl)pentyl)-5H-pyrrolo[3,2-d]pyrimidin-4-amine Prepared similarly to Intermediate 89 from 5-((benzyloxy)methyl)-7-(5-chloropent-1-yn-1-yl)-2-(2-methoxyethyl)-5H-pyrrolo[3,2-d]pyrimidin-4-amine and pyrrolidine.

LCMS (System B): $t_{RET}$=1.01 min; MH+ 448

Example Preparation

Example 1

2-Butyl-7-(6-(Piperidin-1-yl)hexyl)-5H-pyrrolo[3,2-d]pyrimidin-4-amine formate

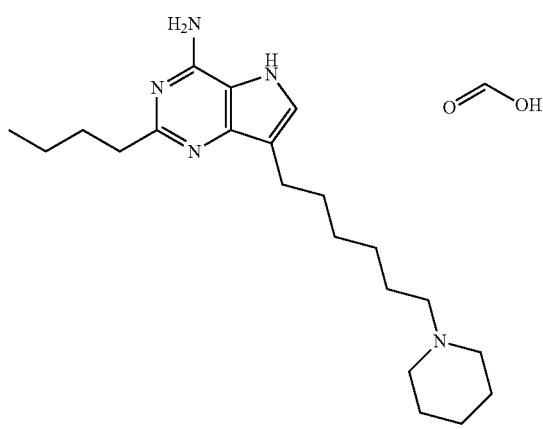 [SMILES: CCCCc1nc(N)c2[nH]cc(CCCCCCN3CCCCC3)c2n1 ; O=CO]

Method A

A solution of 5-((benzyloxy)methyl)-2-butyl-7-(6-(piperidin-1-yl)hex-1-yn-1-yl)-5H-pyrrolo[3,2-d]pyrimidin-4-amine (157 mg, 0.331 mmol) in ethanol (15 ml) was passed through the H-cube (settings: 20° C., full hydrogen, 1 mL/min flow rate and 10% palladium on carbon CatCart30 as the catalyst). A new 10% palladium on carbon CatCart30 cartridge was inserted into the H-cube and the solution was passed again through the H-cube (settings: 40° C., full hydrogen, 1 mL/min flow rate). The process was repeated a further twice using a new cartridge and identical settings on each occassion. The solution was evaporated in-vacuo to yield a white solid. The solid was dissolved in DMSO (7×1 ml) and purified by MDAP (Method A). Appropriate fractions were combined and evaporated in vacuo to yield the title compound as a colourless oil (66 mg).

LCMS (System A): $t_{RET}$=0.50 min; MH$^+$ 358

Method B

A mixture of 2-butyl-7-(6-(piperidin-1-yl)hexyl)-5-((2-(trimethylsilyl)ethoxy)methyl)-5H-pyrrolo[3,2-d]pyrimidin-4-amine (50 mg, 0.103 mmol), ethylenediamine (11 μl, 0.163 mmol) and tetrabutylammonium fluoride 1 M in tetrahydrofuran (310 μl, 0.310 mmol) was heated to 70° C. for 3.5 hours. The reaction was concentrated in vacuo and the residue was dissolved in 1:1 MeOH:DMSO (1 mL) and purified by MDAP (Method A). The solvent was dried under a stream of nitrogen in the Radleys blowdown apparatus to give the title compound (23 mg).

LCMS (System B): $t_{RET}$=1.03 min; MH$^+$ 358

Example 2

2-Butyl-7-(5-(piperidin-1-yl)pentyl)-5H-pyrrolo[3,2-d]pyrimidin-4-amine

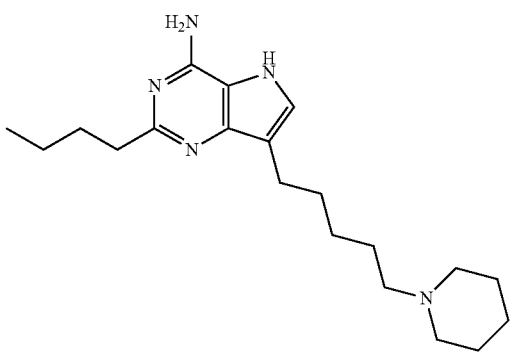 [SMILES: CCCCc1nc(N)c2[nH]cc(CCCCCN3CCCCC3)c2n1]

5-((Benzyloxy)methyl)-2-butyl-7-(5-(piperidin-1-yl)pent-1-yn-1-yl)-5H-pyrrolo[3,2-d]pyrimidin-4-amine (70 mg, 0.152 mmol) in ethanol (20 ml) was filtered and passed through the H-cube (settings: 20° C., full hydrogen, 1 mL/min flow rate and 10% palladium on carbon CatCart30 as the catalyst). A new 10% palladium on carbon CatCart30 cartridge was inserted into the H-cube and the solution was passed again through the H-cube (settings: 45° C., full hydrogen, 1 mL/min flow rate). The process was repeated using a new CatCart each time then the solution was evaporated in vacuo to yield a white solid. The solid was dissolved in MeOH:DMSO (1:1) (1 ml) and purified by MDAP (Method A). Appropriate fractions were combined and evaporated in vacuo to yield the title compound as a colourless oil (4.8 mg).

LCMS (System B): $t_{RET}$=0.94 min; MH$^+$ 344

Example 3

2-Butyl-7-(4-(Piperidin-1-yl)butyl)-5H-pyrrolo[3,2-d]pyrimidin-4-amine

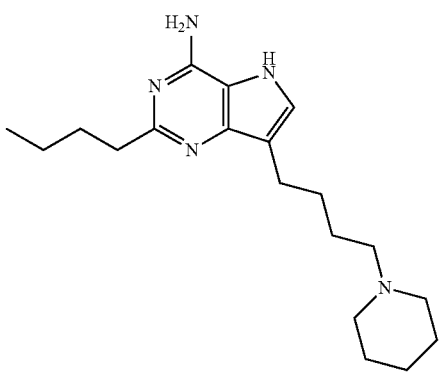 [SMILES: CCCCc1nc(N)c2[nH]cc(CCCCN3CCCCC3)c2n1]

A solution of 5-((benzyloxy)methyl)-2-butyl-7-(4-(piperidin-1-yl)but-1-yn-1-yl)-5H-pyrrolo[3,2-d]pyrimidin-4-amine (95 mg, 0.213 mmol) in ethanol (20 mL) was passed through the H-cube (settings: 20° C., full hydrogen, 1 mL/min flow rate and 10% palladium on carbon CatCart30 as the catalyst). A new 10% palladium on carbon CatCart30 cartridge was inserted into the H-cube and the solution was passed again through the H-cube (settings: 45° C., full hydrogen, 1 mL/min flow rate). The process was repeated a further twice using a new CatCart each time. The solution was evaporated in vacuo to yield a white solid. The solid was dissolved in MeOH:DMSO (1:1) (1 mL) and purified by MDAP (Method B). The appropriate fraction was evaporated in vacuo to yield the title compound as a white solid (6.43 mg).

LCMS (System B): $t_{RET}$=0.90 min; MH$^+$ 330

Example 4

2-(Ethoxymethyl)-7-(6-(piperidin-1-yl)hexyl)-5H-pyrrolo[3,2-d]pyrimidin-4-amine

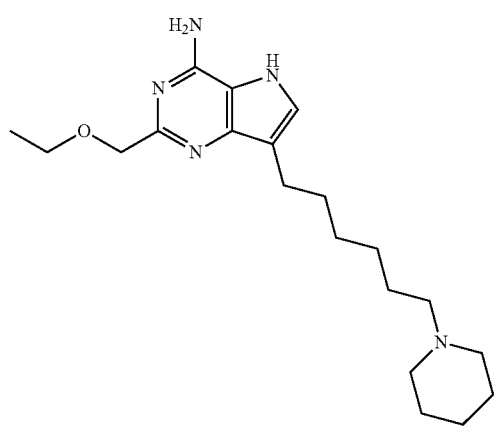 [SMILES: CCOCc1nc(N)c2[nH]cc(CCCCCCN3CCCCC3)c2n1]

A solution of 5-((benzyloxy)methyl)-2-(ethoxymethyl)-7-(6-(piperidin-1-yl)hex-1-yn-1-yl)-5H-pyrrolo[3,2-d]pyrimidin-4-amine (0.296 mL, 0.296 mmol) in methanol (15 mL) was passed through the H-cube (settings: 45° C., full hydrogen, 1 mL/min flow rate and 10% palladium on carbon CatCart30 as the catalyst). The solution was re-run through the H-cube (same settings) then concentrated in vacuo. The residue was dissolved in 50:50 DMSO/MeOH (2 mL) and purified by MDAP (Method B). The fractions which contained product were concentrated to give the title compound as a white solid (41 mg).

LCMS (System B): $t_{RET}$=0.87 min; MH$^+$ 360

Example 5

2-(2-Methoxyethyl)-7-(6-(Piperidin-1-yl)hexyl)-5H-pyrrolo[3,2-d]pyrimidin-4-amine hydrochloride

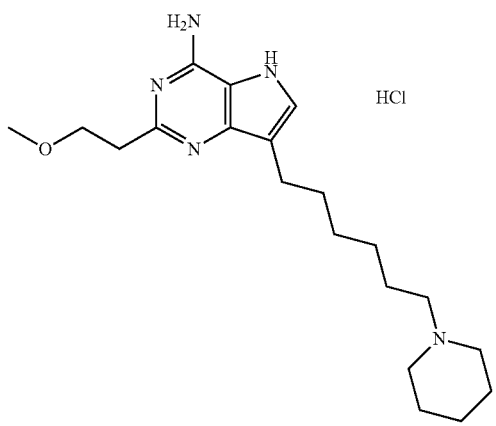 [SMILES: COCCc1nc(N)c2[nH]cc(CCCCCCN3CCCCC3)c2n1 ; Cl]

A solution of 5-((benzyloxy)methyl)-2-(2-methoxyethyl)-7-(6-(piperidin-1-yl)hex-1-yn-1-yl)-5H-pyrrolo[3,2-d]pyrimidin-4-amine (95.5 mg, 0.201 mmol) in methanol (15 mL) was hydrogenated using the H-Cube (settings: 60° C., full H$_2$, 1 mL/min flow rate) and 10% Pd/C CatCart 30 as the catalyst. The methanol was removed in vacuo to give a white solid. The sample was dissolved in 1:1 MeOH:DMSO (1 mL) and purified by MDAP (Method A). The solvent was dried under a stream of nitrogen in the Radleys blowdown apparatus to give the formate salt (31 mg). 4M HCl in dioxane was added and the product was dried under a stream of nitrogen in the Radleys blowdown apparatus to give the title compound (34 mg).

LCMS (System B): $t_{RET}$=0.84 min; MH$^+$ 360

Example 6

2-Butyl-6-methyl-7-(6-(Piperidin-1-yl)hexyl)-5H-pyrrolo[3,2-d]pyrimidin-4-amine

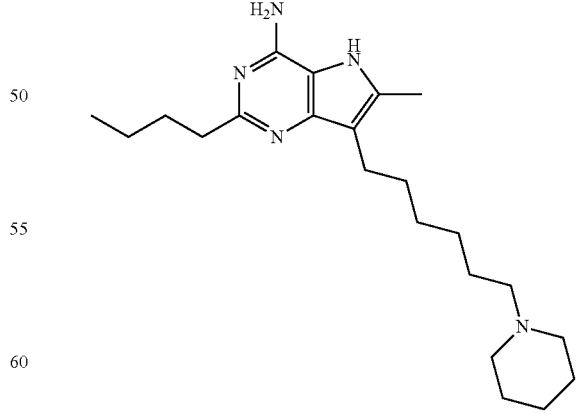

A solution of 5-((benzyloxy)methyl)-2-butyl-6-methyl-7-(6-(piperidin-1-yl)hex-1-yn-1-yl)-5H-pyrrolo[3,2-d]pyrimidin-4-amine (0.275 mL, 0.275 mmol) in methanol (15 mL) was passed through the H-cube (settings: 40° C., full hydrogen, 1 mL/min flow rate and 10% palladium on carbon CatCart30 as the catalyst). The solution was re run through the H-cube (same settings) then evaporated in vacuo to yield a pale brown oil (35 mg). The compound was dissolved in 1 mL of 50:50 DMSO/MeOH and the crude product was purified by MDAP (Method B). Fractions which contained product were concentrated to give the title compound as a white solid (22 mg).

LCMS (System B): $t_{RET}$=1.08 min; MH$^+$ 372

Example 7

2-Butyl-6-methyl-7-(5-(piperidin-1-yl)pentyl)-5H-pyrrolo[3,2-d]pyrimidin-4-amine

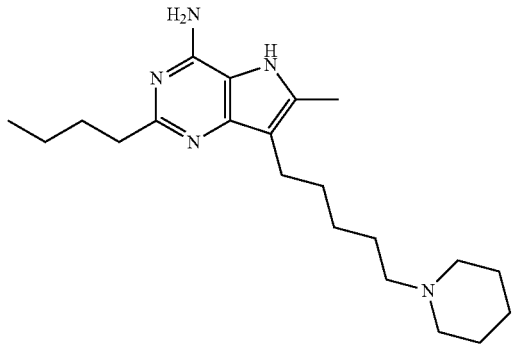 [SMILES: CCCCc1nc(N)c2[nH]c(C)c(CCCCCN3CCCCC3)c2n1]

Prepared similarly to Example 3 from 5-((benzyloxy)methyl)-2-butyl-6-methyl-7-(5-(piperidin-1-yl)pent-1-yn-1-yl)-5H-pyrrolo[3,2-d]pyrimidin-4-amine.

LCMS (System B): $t_{RET}$=1.02 min; MH$^+$ 358

Example 8

2-Butyl-6-methyl-7-(4-(piperidin-1-yl)butyl)-5H-pyrrolo[3,2-d]pyrimidin-4-amine

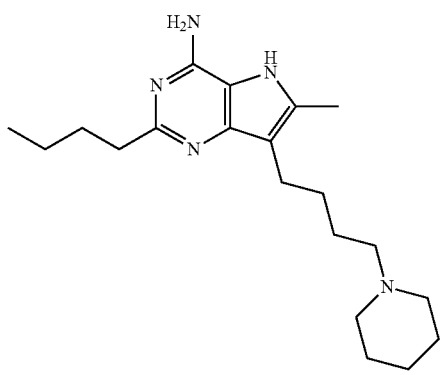 [SMILES: CCCCc1nc(N)c2[nH]c(C)c(CCCCN3CCCCC3)c2n1]

Prepared similarly to Example 4 from 5-((benzyloxy)methyl)-2-butyl-6-methyl-7-(4-(piperidin-1-yl)but-1-yn-1-yl)-5H-pyrrolo[3,2-d]pyrimidin-4-amine.

LCMS (System B): $t_{RET}$=0.98 min; MH$^+$ 344

Example 9

2-Butyl-7-(5-(pyrrolidin-1-yl)pentyl)-5H-pyrrolo[3,2-d]pyrimidin-4-amine formate

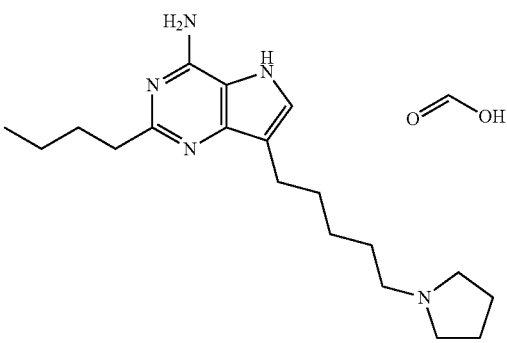 [SMILES: CCCCc1nc(N)c2[nH]cc(CCCCCN3CCCC3)c2n1 ; O=CO]

A solution of 5-((benzyloxy)methyl)-2-butyl-7-(5-(pyrrolidin-1-yl)pent-1-yn-1-yl)-5H-pyrrolo[3,2-d]pyrimidin-4-amine (90 mg, 0.202 mmol) in ethanol (10 mL) was hydrogenated using the H-cube (settings: 60° C., Full H$_2$, 1 mL/min flow rate) and 10% Pd/C CatCart 30 as the catalyst. The reaction mixture was passed through the H-cube again using identical conditions. The reaction was concentrated in vacuo. The residue were dissolved in 1:1 MeOH:DMSO 1 mL and purified by MDAP (Method A). The solvent was dried under a stream of nitrogen in the Radleys blowdown apparatus to give the title compound as a white gum (16 mg).

LCMS (System A): $t_{RET}$=0.44 min; MH$^+$ 330

Example 10

2-Butyl-7-(6-(pyrrolidin-1-yl)hexyl)-5H-pyrrolo[3,2-d]pyrimidin-4-amine

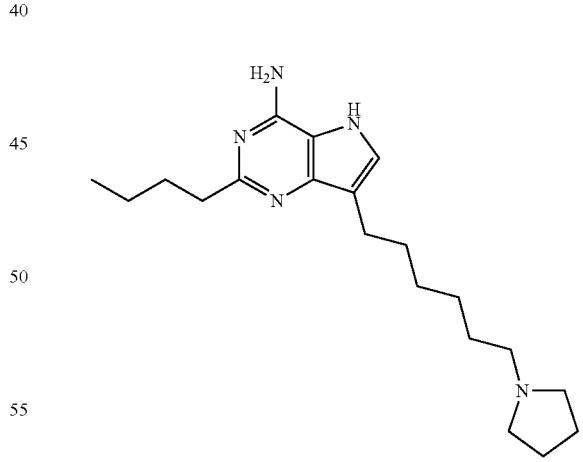

A solution of 5-((benzyloxy)methyl)-2-butyl-7-(6-(pyrrolidin-1-yl)hex-1-yn-1-yl)-5H-pyrrolo[3,2-d]pyrimidin-4-amine (55 mg, 0.120 mmol) in ethanol (4.5 mL) and acetic acid (0.5 mL) was hydrogenated using the H-cube (settings: 60° C., Full H$_2$, 1 mL/min flow rate) and 10% Pd/C CatCart 30 as the catalyst. The reaction mixture was concentrated in vacuo at 60° C. to give a colourless oil (45 mg). The samples was dissolved in 1:1 DMF:DMSO (1 mL) and purified by MDAP (Method B). The majority of the solvent was evaporated in vacuo at 60° C. and the remainder removed in a Radleys blowdown apparatus at 50° C. to give the title compound as a white solid (20 mg).

LCMS (System B): $t_{RET}$=0.93 min; MH⁺ 342

Example 11

2-Pentyl-7-(6-(Piperidin-1-yl)hexyl)-5H-pyrrolo[3,2-d]pyrimidin-4-amine

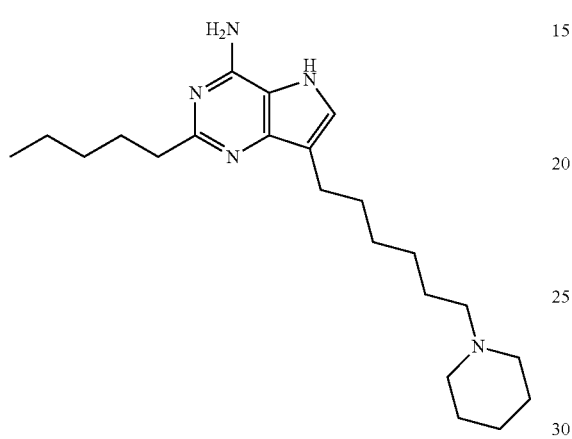

Prepared similarly to Example 10 from 5-((benzyloxy)methyl)-2-pentyl-7-(6-(piperidin-1-yl)hex-1-yn-1-yl)-5H-pyrrolo[3,2-d]pyrimidin-4-amine.

LCMS (System B): $t_{RET}$=1.17 min; MH⁺ 372

Example 12

7-(5-(Azepan-1-yl)pentyl)-2-butyl-5H-pyrrolo[3,2-d]pyrimidin-4-amine

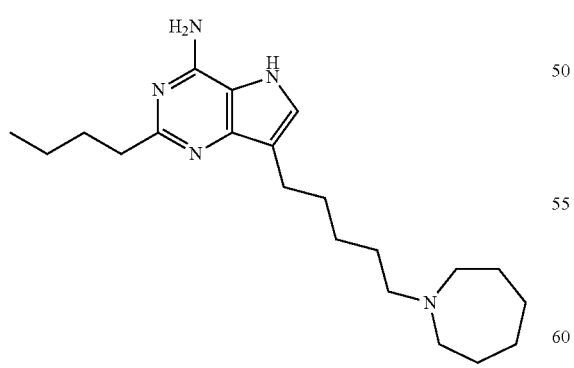

Prepared similarly to Example 10 from 7-(5-(azepan-1-yl)pent-1-yn-1-yl)-5-((benzyloxy)methyl)-2-butyl-5H-pyrrolo[3,2-d]pyrimidin-4-amine.

LCMS (System B): $t_{RET}$=0.89 min; MH⁺ 358

Example 13

7-(4-(Azepan-1-yl)butyl)-2-butyl-6-methyl-5H-pyrrolo[3,2-d]pyrimidin-4-amine

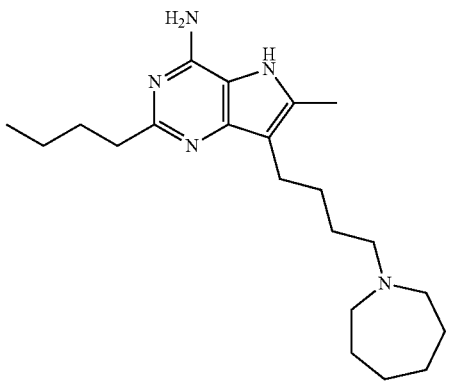 [SMILES: CCCCc1nc(N)c2[nH]c(C)c(CCCCN3CCCCCC3)c2n1]

Prepared similarly to Example 10 from 7-(4-(azepan-1-yl)butyl)-5-((benzyloxy)methyl)-2-butyl-6-methyl-5H-pyrrolo[3,2-d]pyrimidin-4-amine.

LCMS (System B): $t_{RET}$=0.93 min; MH⁺ 358

Example 14

2-Butyl-6-methyl-7-(6-(pyrrolidin-1-yl)hexyl)-5H-pyrrolo[3,2-d]pyrimidin-4-amine

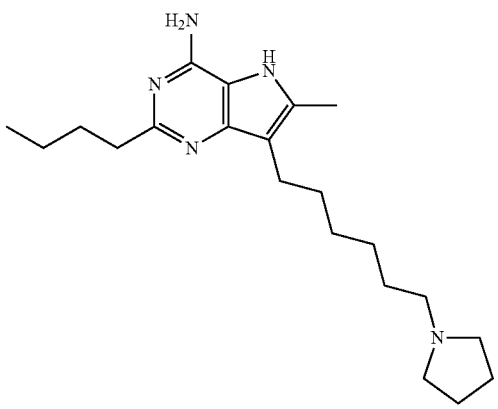 [SMILES: CCCCc1nc(N)c2[nH]c(C)c(CCCCCCN3CCCC3)c2n1]

Prepared similarly to Example 10 from 5-((benzyloxy)methyl)-2-butyl-6-methyl-7-(6-(pyrrolidin-1-yl)hex-1-yn-1-yl)-5H-pyrrolo[3,2-d]pyrimidin-4-amine.

LCMS (System B): $t_{RET}$=0.94 min; MH⁺ 358

Example 15

7-(6-(Azetidin-1-yl)hexyl)-2-butyl-6-methyl-5H-pyrrolo[3,2-d]pyrimidin-4-amine

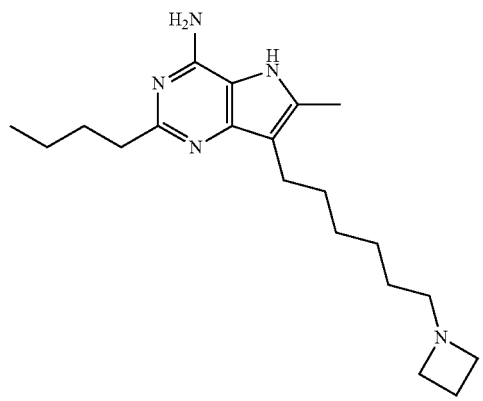 [SMILES: CCCCc1nc(N)c2[nH]c(C)c(CCCCCCN3CCC3)c2n1]

Prepared similarly to Example 10 from 7-(6-(azetidin-1-yl)hex-1-yn-1-yl)-5-((benzyloxy)methyl)-2-butyl-6-methyl-5H-pyrrolo[3,2-d]pyrimidin-4-amine.

LCMS (System B): $t_{RET}$=0.96 min; MH⁺ 342

Example 16

2-Butyl-6-methyl-7-(5-(pyrrolidin-1-yl)pentyl)-5H-pyrrolo[3,2-d]pyrimidin-4-amine

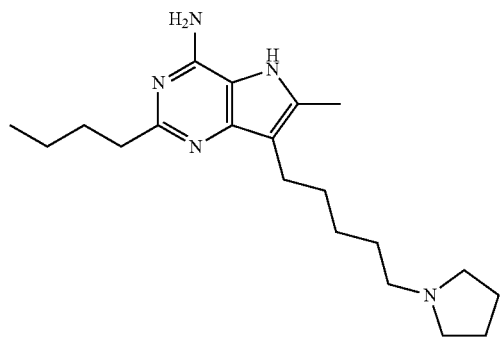 [SMILES: CCCCc1nc(N)c2[nH]c(C)c(CCCCCN3CCCC3)c2n1]

Prepared similarly to Example 10 from 5-((benzyloxy)methyl)-2-butyl-6-methyl-7-(5-(pyrrolidin-1-yl)pent-1-yn-1-yl)-5H-pyrrolo[3,2-d]pyrimidin-4-amine.

LCMS (System B): $t_{RET}$=0.89 min; MH⁺ 344

Example 17

7-(5-(Azetidin-1-yl)pentyl)-2-butyl-5H-pyrrolo[3,2-d]pyrimidin-4-amine

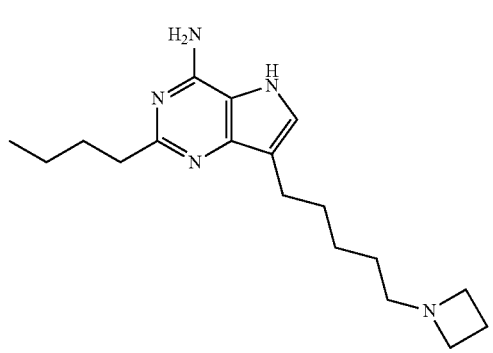 [SMILES: CCCCc1nc(N)c2[nH]cc(CCCCCN3CCC3)c2n1]

Prepared similarly to Example 10 from 7-(5-(azetidin-1-yl)pent-1-yn-1-yl)-5-((benzyloxy)methyl)-2-butyl-5H-pyrrolo[3,2-d]pyrimidin-4-amine.

LCMS (System B): $t_{RET}$=0.89 min; MH⁺ 316

Example 18

7-(5-(Azetidin-1-yl)pentyl)-2-butyl-6-methyl-5H-pyrrolo[3,2-d]pyrimidin-4-amine

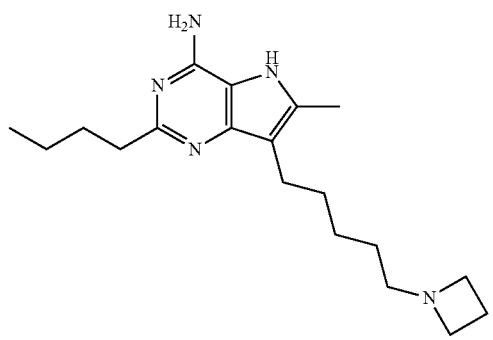 [SMILES: CCCCc1nc(N)c2[nH]c(C)c(CCCCCN3CCC3)c2n1]

Prepared similarly to Example 10 from 7-(5-(azetidin-1-yl)pent-1-yn-1-yl)-5-((benzyloxy)methyl)-2-butyl-6-methyl-5H-pyrrolo[3,2-d]pyrimidin-4-amine.

LCMS (System B): $t_{RET}$=0.82 min; MH⁺ 330

Example 19

2-Butyl-6-methyl-7-(4-(pyrrolidin-1-yl)butyl)-5H-pyrrolo[3,2-d]pyrimidin-4-amine

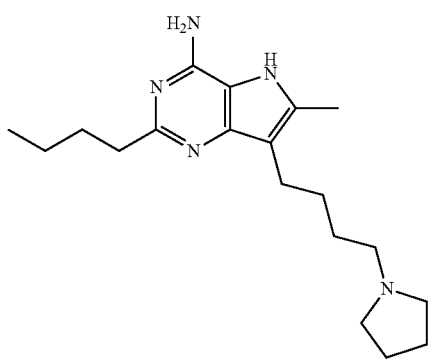 [SMILES: CCCCc1nc(N)c2[nH]c(C)c(CCCCN3CCCC3)c2n1]

Prepared similarly to Example 10 from 5-((benzyloxy)methyl)-2-butyl-6-methyl-7-(4-(pyrrolidin-1-yl)butyl)-5H-pyrrolo[3,2-d]pyrimidin-4-amine LCMS (System B): $t_{RET}$=1.00 min; MH$^+$ 330

Example 20

2-Butyl-7-(5-(4,4-difluoropiperidin-1-yl)pentyl)-5H-pyrrolo[3,2-d]pyrimidin-4-amine

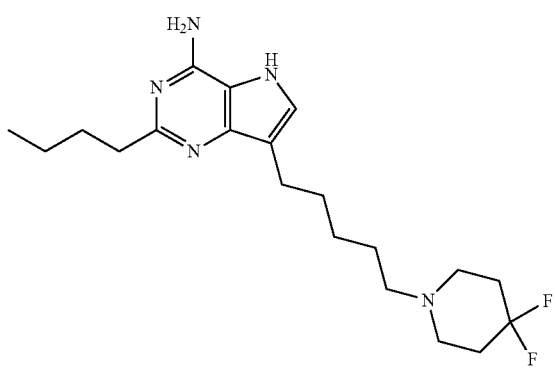 [SMILES: CCCCc1nc(N)c2[nH]cc(CCCCCN3CCC(F)(F)CC3)c2n1]

Prepared similarly to Example 10 from 5-((benzyloxy)methyl)-2-butyl-7-(5-(4,4-difluoropiperidin-1-yl)pent-1-yn-1-yl)-5H-pyrrolo[3,2-d]pyrimidin-4-amine LCMS (System B): $t_{RET}$=1.06 min; MH$^+$ 380

Example 21

2-Butyl-7-(5-(4-fluoropiperidin-1-yl)pentyl)-5H-pyrrolo[3,2-d]pyrimidin-4-amine

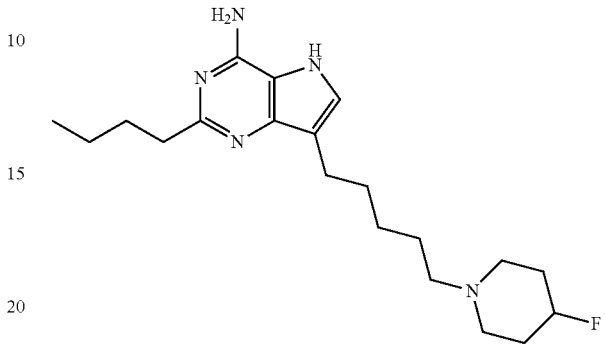

Prepared similarly to Example 10 from 5-((benzyloxy)methyl)-2-butyl-7-(5-(4-fluoropiperidin-1-yl)pent-1-yn-1-yl)-5H-pyrrolo[3,2-d]pyrimidin-4-amine.

LCMS (System B): $t_{RET}$=1.00 min; MH$^+$ 362

Example 22

7-(5-(4-Fluoropiperidin-1-yl)pentyl)-2-(2-methoxyethyl)-5H-pyrrolo[3,2-d]pyrimidin-4-amine

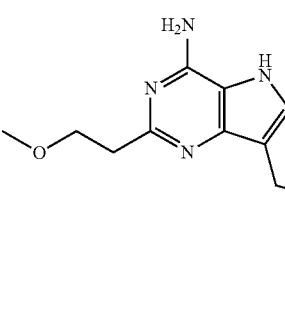

Prepared similarly to Example 10 from 5-((benzyloxy)methyl)-7-(5-(4-fluoropiperidin-1-yl)pent-1-yn-1-yl)-2-(2-methoxyethyl)-5H-pyrrolo[3,2-d]pyrimidin-4-amine.

LCMS (System B): $t_{RET}$=0.81 min; MH$^+$ 364

Example 23

1-(5-(4-Amino-2-butyl-5H-pyrrolo[3,2-d]pyrimidin-7-yl)pentyl)piperidin-4-ol

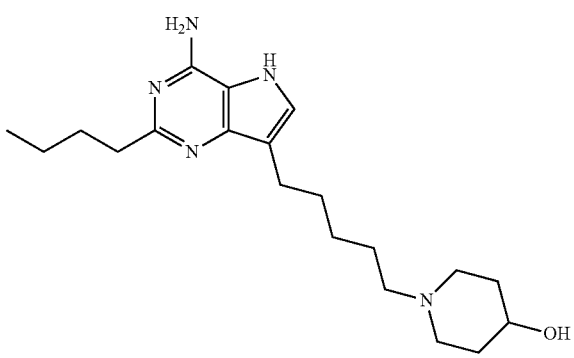 [SMILES: CCCCc1nc(N)c2[nH]cc(CCCCCN3CCC(O)CC3)c2n1]

Prepared similarly to Example 10 from 1-(5-(4-amino-5-((benzyloxy)methyl)-2-butyl-5H-pyrrolo[3,2-d]pyrimidin-7-yl)pent-4-yn-1-yl)piperidin-4-ol.

LCMS (System B): $t_{RET}$=0.75 min; MH$^+$ 360

Example 24

(R)-2-Butyl-7-(5-(3-fluoropyrrolidin-1-yl)pentyl)-5H-pyrrolo[3,2-d]pyrimidin-4-amine

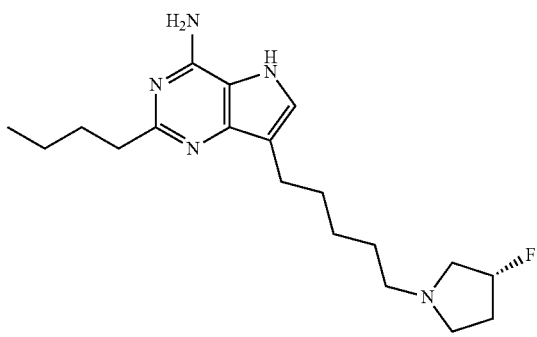 [SMILES: CCCCc1nc(N)c2[nH]cc(CCCCCN3CC[C@@H](F)C3)c2n1]

Prepared similarly to Example 10 from (R)-5-((benzyloxy)methyl)-2-butyl-7-(5-(3-fluoropyrrolidin-1-yl)pent-1-yn-1-yl)-5H-pyrrolo[3,2-d]pyrimidin-4-amine.

LCMS (System B): $t_{RET}$=0.93 min; MH$^+$ 348

Example 25

(S)-2-Butyl-7-(5-(3-fluoropyrrolidin-1-yl)pentyl)-5H-pyrrolo[3,2-d]pyrimidin-4-amine

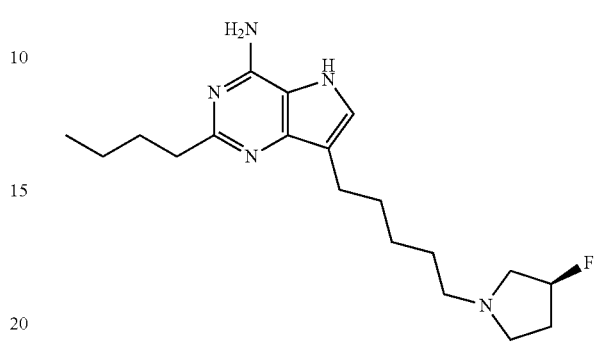

Prepared similarly to Example 10 from (S)-5-((benzyloxy)methyl)-2-butyl-7-(5-(3-fluoropyrrolidin-1-yl)pent-1-yn-1-yl)-5H-pyrrolo[3,2-d]pyrimidin-4-amine.

LCMS (System B): $t_{RET}$=0.93 min; MH$^+$ 348

Example 26

(R)-7-(5-(3-Fluoropyrrolidin-1-yl)pentyl)-2-(2-methoxyethyl)-5H-Pyrrolo[3,2-d]pyrimidin-4-amine formate

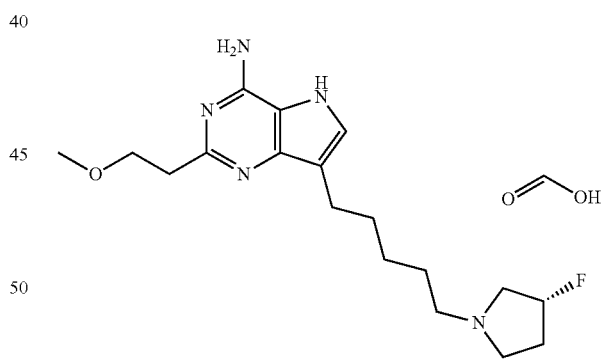

A solution of crude (R)-5-((benzyloxy)methyl)-7-(5-(3-fluoropyrrolidin-1-yl)pent-1-yn-1-yl)-2-(2-methoxyethyl)-5H-pyrrolo[3,2-d]pyrimidin-4-amine (278 mg, 0.597 mmol) in ethanol (25 mL) and acetic Acid (2.5 mL) was hydrogenated using the H-cube (settings: 60° C., Full H$_2$, 1 mL/min flow rate) and 10% Pd/C CatCart 30 as the catalyst. The material was re run 3 times through the H-cube. The crude material was dissolved in DMSO MeOH (3 mL) and a sample (1 mL) purified by MDAP (Method A). Fractions containing desired product were combined and concentrated in vacuo to give the title compound as a clear oil (31.3 mg).

LCMS (System B): $t_{RET}$=0.75 min; MH$^+$ 350

Example 27

(S)-7-(5-(3-Fluoropyrrolidin-1-yl)pentyl)-2-(2-methoxyethyl)-5H-pyrrolo[3,2-d]pyrimidin-4-amine formate

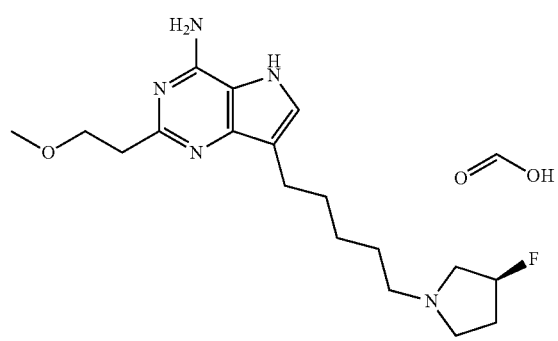 [SMILES: COCCc1nc(N)c2[nH]cc(CCCCCN3CC[C@H](F)C3)c2n1 ; O=CO]

Prepared similarly to Example 26 from (S)-5-((benzyloxy)methyl)-7-(5-(3-fluoropyrrolidin-1-yl)pent-1-yn-1-yl)-2-(2-methoxyethyl)-5H-pyrrolo[3,2-d]pyrimidin-4-amine.

LCMS (System B): $t_{RET}$=0.73 min; MH$^+$ 350

Example 28

(S)-1-(5-(4-Amino-2-butyl-5H-pyrrolo[3,2-d]pyrimidin-7-yl)pentyl)pyrrolidin-3-ol

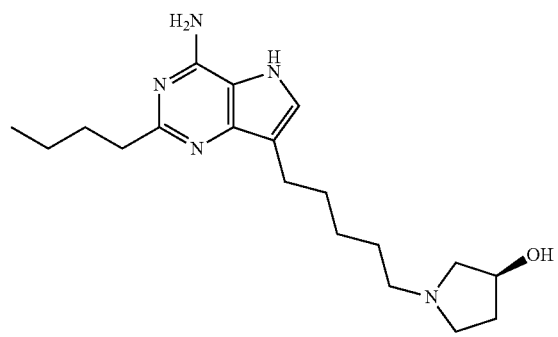 [SMILES: CCCCc1nc(N)c2[nH]cc(CCCCCN3CC[C@H](O)C3)c2n1]

Prepared similarly to Example 10 from (S)-1-(5-(4-amino-5-((benzyloxy)methyl)-2-butyl-5H-pyrrolo[3,2-d]pyrimidin-7-yl)pent-4-yn-1-yl)pyrrolidin-3-ol.

LCMS (System B): $t_{RET}$=0.77 min; MH$^+$ 348

Example 29

1-(5-(4-Amino-2-butyl-5H-pyrrolo[3,2-d]pyrimidin-7-yl)pentyl)azetidin-3-ol formate

Prepared similarly to Example 27 from 1-(5-(4-amino-5-((benzyloxy)methyl)-2-butyl-5H-pyrrolo[3,2-d]pyrimidin-7-yl)pent-4-yn-1-yl)azetidin-3-ol.

LCMS (System B): $t_{RET}$=0.73 min; MH$^+$ 332

Example 30

7-(6-(Azepan-1-yl)hexyl)-2-(2-methoxyethyl)-5H-pyrrolo[3,2-d]pyrimidin-4-amine

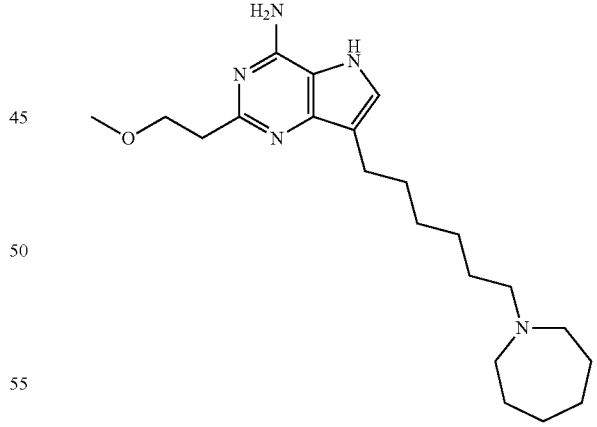

Prepared similarly to Example 10 from 7-(6-(azepan-1-yl)hex-1-yn-1-yl)-5-((benzyloxy)methyl)-2-(2-methoxyethyl)-5H-pyrrolo[3,2-d]pyrimidin-4-amine.

LCMS (System B): $t_{RET}$=0.82 min; MH$^+$ 374

Example 31

2-Butyl-7-(6-(4-fluoropiperidin-1-yl)hexyl)-5H-pyrrolo[3,2-d]pyrimidin-4-amine

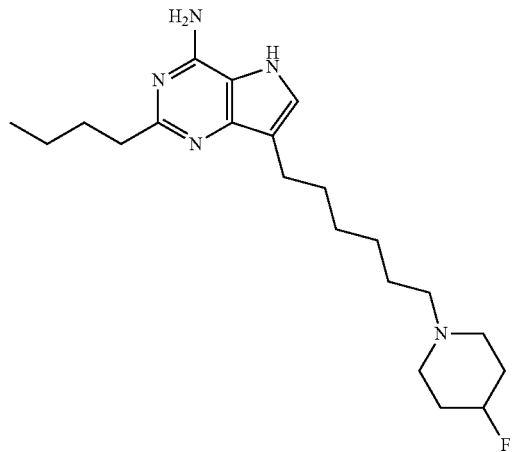 [SMILES: CCCCc1nc(N)c2[nH]cc(CCCCCCN3CCC(F)CC3)c2n1]

Prepared similarly to Example 10 from 5-((benzyloxy)methyl)-2-butyl-7-(6-(4-fluoropiperidin-1-yl)hex-1-yn-1-yl)-5H-pyrrolo[3,2-d]pyrimidin-4-amine.

LCMS (System B): $t_{RET}$=1.00 min; MH$^+$ 376

Example 32

(R)-2-Butyl-7-(6-(3-fluoropyrrolidin-1-yl)hexyl)-5H-pyrrolo[3,2-d]pyrimidin-4-amine

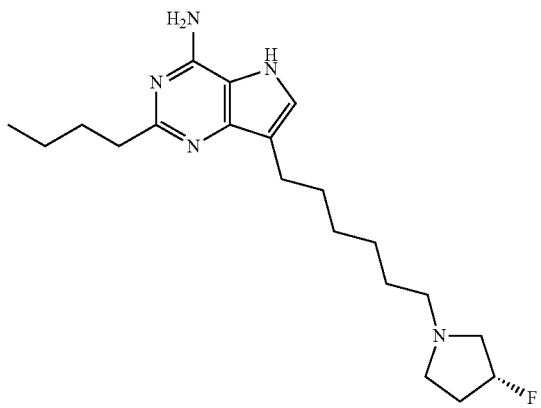 [SMILES: CCCCc1nc(N)c2[nH]cc(CCCCCCN3CC[C@@H](F)C3)c2n1]

Prepared similarly to Example 10 from (R)-5-((benzyloxy)methyl)-2-butyl-7-(6-(3-fluoropyrrolidin-1-yl)hex-1-yn-1-yl)-5H-pyrrolo[3,2-d]pyrimidin-4-amine but using 5% Pd/C CatCart 30 cartridges and running twice through the H-cube.

LCMS (System B): $t_{RET}$=0.96 min; MH$^+$ 362

Example 33

(S)-2-Butyl-7-(6-(3-fluoropyrrolidin-1-yl)hexyl)-5H-pyrrolo[3,2-d]pyrimidin-4-amine

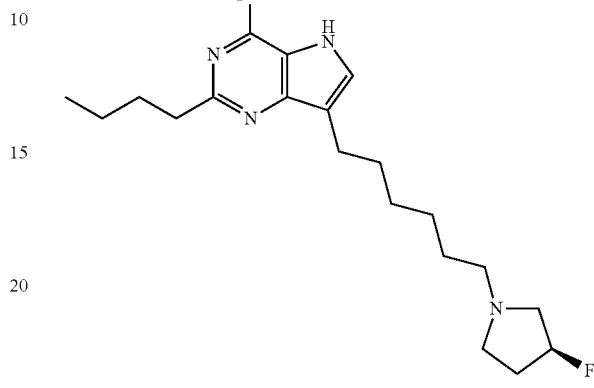

Prepared similarly to Example 32 from (S)-5-((benzyloxy)methyl)-2-butyl-7-(6-(3-fluoropyrrolidin-1-yl)hex-1-yn-1-yl)-5H-pyrrolo[3,2-d]pyrimidin-4-amine.

LCMS (System B): $t_{RET}$=0.95 min; MH$^+$ 362

Example 34

(S)-2-Butyl-7-(5-(2-methylpyrrolidin-1-yl)pentyl)-5H-pyrrolo[3,2-d]pyrimidin-4-amine

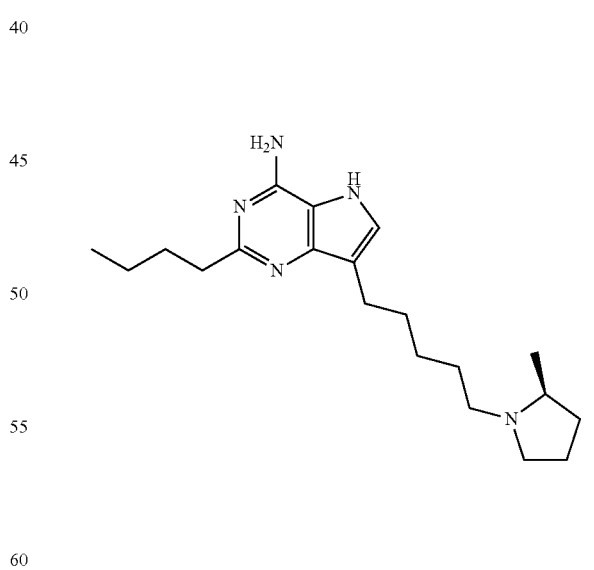

Prepared similarly to Example 10 from (S)-5-((benzyloxy)methyl)-2-butyl-7-(5-(2-methylpyrrolidin-1-yl)pent-1-yn-1-yl)-5H-pyrrolo[3,2-d]pyrimidin-4-amine.

LCMS (System B): $t_{RET}$=0.86 min; MH$^+$ 344

Example 35

(R)-2-Butyl-7-(5-(2-methylpyrrolidin-1-yl)pentyl)-5H-pyrrolo[3,2-d]pyrimidin-4-amine

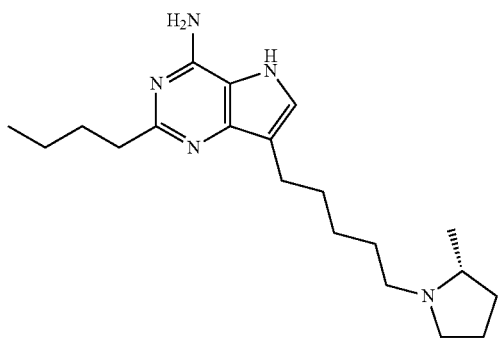 [SMILES: CCCCc1nc(N)c2[nH]cc(CCCCCN3CCC[C@H]3C)c2n1]

Prepared similarly to Example 34 from (R)-5-((benzyloxy)methyl)-2-butyl-7-(5-(2-methylpyrrolidin-1-yl)pent-1-yn-1-yl)-5H-pyrrolo[3,2-d]pyrimidin-4-amine but with passing twice through the H-cube using the same 10% Pd/C CatCart 30 cartridge.

LCMS (System B): $t_{RET}$=0.85 min; MH$^+$ 344

Example 36

2-Butyl-7-(5-(3-methylazetidin-1-yl)pentyl)-5H-pyrrolo[3,2-d]pyrimidin-4-amine

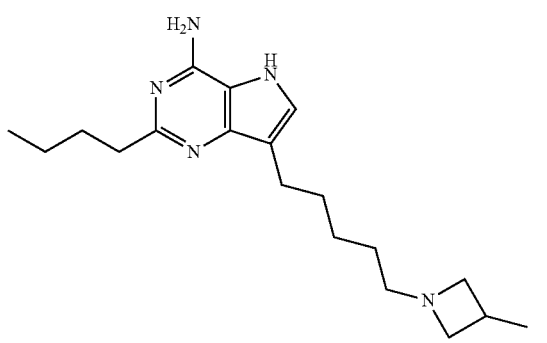 [SMILES: CCCCc1nc(N)c2[nH]cc(CCCCCN3CC(C)C3)c2n1]

Prepared similarly to Example 10 from 5-((benzyloxy)methyl)-2-butyl-7-(5-(3-methylazetidin-1-yl)pent-1-yn-1-yl)-5H-pyrrolo[3,2-d]pyrimidin-4-amine.

LCMS (System B): $t_{RET}$=0.90 min; MH$^+$ 330

Example 37

2-Butyl-7-(5-(3-fluoroazetidin-1-yl)pentyl)-5H-pyrrolo[3,2-d]pyrimidin-4-amine

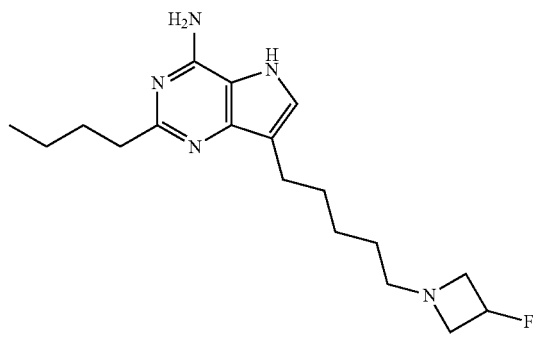 [SMILES: CCCCc1nc(N)c2[nH]cc(CCCCCN3CC(F)C3)c2n1]

Prepared similarly to Example 35 from 5-((benzyloxy)methyl)-2-butyl-7-(5-(3-fluoroazetidin-1-yl)pent-1-yn-1-yl)-5H-pyrrolo[3,2-d]pyrimidin-4-amine.

LCMS (System B): $t_{RET}$=0.89 min; MH$^+$ 334

Example 38

2-Butyl-6-methyl-7-(6-(pyrrolidin-1-yl)hexyl)-5H-pyrrolo[3,2-d]pyrimidin-4-amine Prepared similarly to Example 35 from 5-((benzyloxy)methyl)-2-butyl-6-methyl-7-(6-(pyrrolidin-1-yl)hex-1-yn-1-yl)-5H-pyrrolo[3,2-d]pyrimidin-4-amine.

LCMS (System B): $t_{RET}$=0.94 min; MH$^+$ 358

Example 39

2-Butyl-7-(5-(4-fluoropiperidin-1-yl)pentyl)-6-methyl-5H-pyrrolo[3,2-d]pyrimidin-4-amine

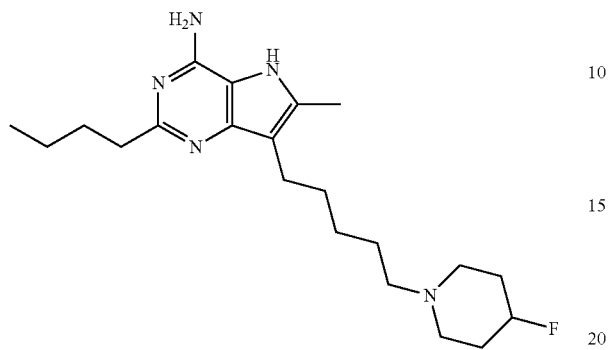

Prepared similarly to Example 10 from 5-((benzyloxy)methyl)-2-butyl-7-(5-(4-fluoropiperidin-1-yl)pent-1-yn-1-yl)-6-methyl-5H-pyrrolo[3,2-d]pyrimidin-4-amine but in this case the product obtained from the MDAP was dissolved in DCM (10 mL) and washed with saturated aqueous sodium bicarbonate (10 mL). The organic phase was separated and the aqueous layer back extracted with 1:1 ethyl acetate:chloroform (3×10 mL). The combined organic extracts were dried (hydrophobic frit) and concentrated in vacuo to give the title compound as a white solid (19 mg).

LCMS (System B): $t_{RET}$=1.01 min; MH+ 376

Example 40

(S)-2-Butyl-7-(5-(3-fluoropyrrolidin-1-yl)pentyl)-6-methyl-5H-pyrrolo[3,2-d]pyrimidin-4-amine

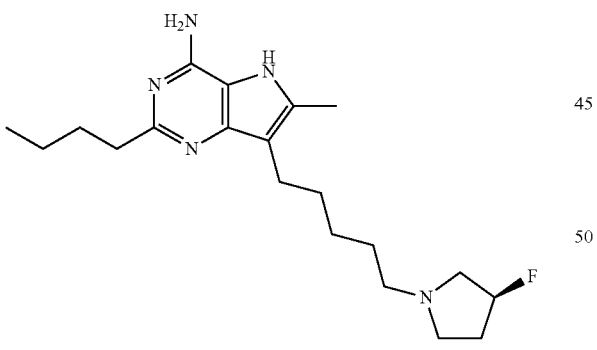

(S)-5-((benzyloxy)methyl)-2-butyl-7-(5-(3-fluoropyrrolidin-1-yl)pent-1-yn-1-yl)-6-methyl-5H-pyrrolo[3,2-d]pyrimidin-4-amine (265.7 mg, 0.556 mmol) was dissolved in methanol (30 mL) and acetic acid (3 mL) and hydrogenated using the H-cube (settings: 60° C., full hydrogen, 1 mL/min flow rate) and 10% Pd/C CatCart 30 as the catalyst. The mixture was passed though the H-cube a second time and then the methanol was evaporated and the crude material was purified MDAP (Method B). Appropriate fractions were combined and evaporated in vacuo to yield the title compound as a clear oil (116 mg).

LCMS (System B): $t_{RET}$=0.92 min; MH+ 362

Example 41

(R)-2-Butyl-7-(5-(3-fluoropyrrolidin-1-yl)pentyl)-6-methyl-5H-pyrrolo[3,2-d]pyrimidin-4-amine

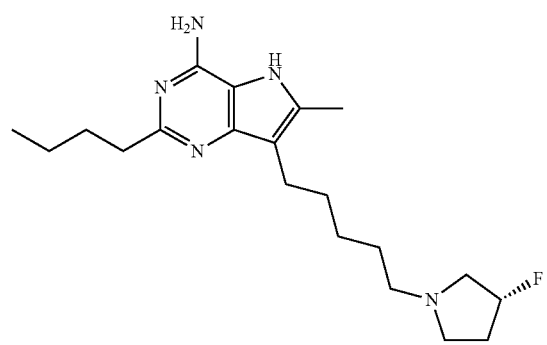 [SMILES: CCCCc1nc(N)c2[nH]c(C)c(CCCCCN3CC[C@@H](F)C3)c2n1]

Prepared similarly to Example 10 from (R)-5-((benzyloxy)methyl)-2-butyl-7-(5-(3-fluoropyrrolidin-1-yl)pent-1-yn-1-yl)-6-methyl-5H-pyrrolo[3,2-d]pyrimidin-4-amine.

LCMS (System B): $t_{RET}$=0.96 min; MH+ 362

Example 42

2-Butyl-7-(5-(3-fluoroazetidin-1-yl)pentyl)-6-methyl-5H-pyrrolo[3,2-d]pyrimidin-4-amine

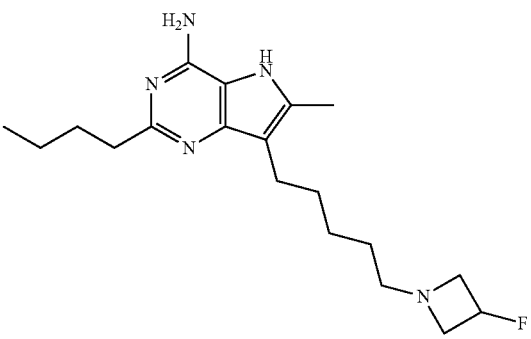 [SMILES: CCCCc1nc(N)c2[nH]c(C)c(CCCCCN3CC(F)C3)c2n1]

Prepared similarly to Example 10 from 5-((benzyloxy)methyl)-2-butyl-7-(5-(3-fluoroazetidin-1-yl)pent-1-yn-1-yl)-6-methyl-5H-pyrrolo[3,2-d]pyrimidin-4-amine.

LCMS (System B): $t_{RET}$=0.91 min; MH+ 348

Example 43

2-(2-Methoxyethyl)-7-(5-(pyrrolidin-1-yl)pentyl)-5H-pyrrolo[3,2-d]pyrimidin-4-amine

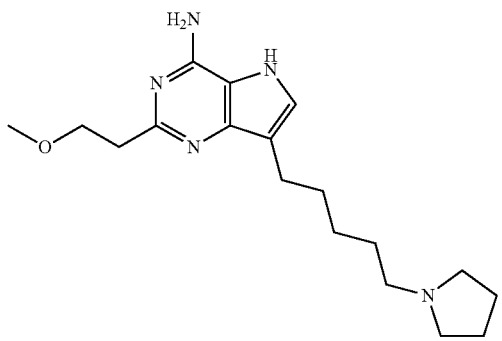 [SMILES: COCCc1nc(N)c2[nH]cc(CCCCCN3CCCC3)c2n1]

Prepared similarly to Example 10 from 5-((benzyloxy)methyl)-2-(2-methoxyethyl)-7-(5-(Pyrrolidin-1-yl)pentyl)-5H-pyrrolo[3,2-d]pyrimidin-4-amine.

LCMS (System B): $t_{RET}$=0.70 min; MH⁺ 332

Biological Evaluation

Compounds of the invention were tested for in vitro biological activity in accordance with the following assay.

Assay for the Induction of Interferon-α and TNF-α Using Fresh Human Whole Blood (WB)

Compound Preparation

Compounds were prepared at 100× required concentration in DMSO in flat-bottom microtitre plates at a volume of 1.5 μL. Columns 1-10 contained a 1 in 4 serial dilution of the test compound. Included on each plate was a serial dilution of the TLR78 agonist resiquimod as a standard and Column 11 contained 1.5 μl of 200 μM resiquimod (giving a 2 μM final concentration, used to define the approximate maximal response to resiquimod). Each compound was assayed in duplicate for each donor.

Incubation and Assays for Interferon-α and TNF-α

Blood samples from three human donors were collected into sodium heparin (10 U/ml). 150 μl of whole Blood was dispensed into Col 1 to 11 of assay plates containing 1.5 μl of test compound or standard in DMSO. Plates were placed in an incubator overnight (37° C., 95% air, 5% $CO_2$). Following the overnight incubation, plates were removed from the incubator & mixed on an orbital shaker for approximately 1 minute. 100 μl of 0.9% saline was added to each well and the plates mixed again on an orbital shaker. Plates were then centrifuged (2500 rpm, 10 mins), after which a sample of plasma was removed using a Biomek FX and assayed for both IFN-α and TNF-α using the MSD (Mesoscale Discovery) electrochemiluminescence assay platform. The IFN-α assay was carried out similarly to that described above. The TNF-α assay was carried out as per kit instructions (Cat No K111BHB).

Cytokine released was expressed as a percentage of the 2 μM resiquimod control (column 11). This percentage was plotted against compound concentration and the $pEC_{50}$ for the response determined by non-linear least squares curve fitting. For the IFN-α responses, generally a 4 parameter logistic model was selected. For the TNF-α responses where a clear maximum response was obtained (i.e. a well defined plateau in the response was observed) then a 4 parameter model was generally used. If the upper asymptote of the curve wasn't well defined then the curve fitting was generally constrained to a maximal response of 100% (i.e. to the response to 2 μM resiquimod) or to the response of the highest concentration tested if this was greater than the resiquimod response. Some curves were bell shaped for one or both cytokines and the cytokine data on the down slope of the bell shaped response (i.e. concentrations above those giving the maximal response) were generally excluded from the fit, usually with the exception of the concentration immediately above the peak response. Curve fitting thus concentrated on the up slope of the dose response curve.

Results

Examples 1 to 43 had a mean $pEC_{50}$ for IFN-α≥5.3.

Examples 1 to 43 had a mean $pEC_{50}$ for TNF-α of ≤5.3.

What is claimed is:

1. A compound of formula (I), or a pharmaceutically acceptable salt thereof:

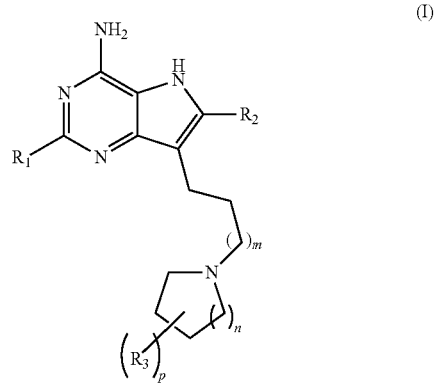

wherein:
$R_1$ is n-$C_{4-6}$alkyl or $C_{1-2}$alkoxy$C_{1-2}$alkyl-;
$R_2$ is hydrogen or methyl;
each $R_3$ is hydroxy, halo or n-$C_{1-3}$alkyl;
m is an integer having a value of 2 to 4;
n is an integer having a value of 0 to 3;
p is an integer having a value of 0 to 2.

2. The compound or a pharmaceutically acceptable salt thereof according to claim 1 wherein $R_1$ is n-butyl.

3. The compound or a pharmaceutically acceptable salt thereof according to claim 1 wherein $R_1$ is ethoxymethyl.

4. The compound or a pharmaceutically acceptable salt thereof according to claim 1 wherein $R_1$ is 2-methoxyethyl.

5. The compound or a pharmaceutically acceptable salt thereof according to claim 1 wherein $R_2$ is hydrogen.

6. The compound or a pharmaceutically acceptable salt thereof according to claim 1 wherein $R_2$ is methyl.

7. The compound or a pharmaceutically acceptable salt thereof according to claim 1 wherein n is an integer having a value of 1 or 2.

8. The compound or a pharmaceutically acceptable salt thereof according to claim 1 wherein p is 0.

9. The compound or a pharmaceutically acceptable salt thereof according to claim 1 wherein $R_3$ is hydroxy or halo.

10. The compound or a pharmaceutically acceptable salt thereof according to claim 1 wherein p is 1 and $R_3$ is hydroxy or fluoro.

11. The compound or a pharmaceutically acceptable salt thereof according to claim 1 wherein p is 2 and $R_3$ is fluoro.

12. The compound or a pharmaceutically acceptable salt thereof according to claim 1 selected from the group consisting of:

2-Butyl-7-(6-(piperidin-1-yl)hexyl)-5H-pyrrolo[3,2-d]pyrimidin-4-amine;
2-Butyl-7-(5-(piperidin-1-yl)pentyl)-5H-pyrrolo[3,2-d]pyrimidin-4-amine;
2-Butyl-7-(4-(piperidin-1-yl)butyl)-5H-pyrrolo[3,2-d]pyrimidin-4-amine;
2-(Ethoxymethyl)-7-(6-(piperidin-1-yl)hexyl)-5H-pyrrolo[3,2-d]pyrimidin-4-amine;
2-(2-Methoxyethyl)-7-(6-(piperidin-1-yl)hexyl)-5H-pyrrolo[3,2-d]pyrimidin-4-amine;
2-Butyl-6-methyl-7-(6-(piperid in-1-yl)hexyl)-5H-pyrrolo[3,2-d]pyrimidin-4-amine;
2-Butyl-6-methyl-7-(5-(piperidin-1-yl)pentyl)-5H-pyrrolo[3,2-d]pyrimidin-4-amine;
2-Butyl-6-methyl-7-(4-(piperidin-1-yl)butyl)-5H-pyrrolo[3,2-d]pyrimidin-4-amine;
2-Butyl-7-(5-(pyrrolidin-1-yl)pentyl)-5H-pyrrolo[3,2-d]pyrimidin-4-amine;
2-Butyl-7-(6-(pyrrolidin-1-yl)hexyl)-5H-pyrrolo[3,2-d]pyrimidin-4-amine;
2-Pentyl-7-(6-(piperidin-1-yl)hexyl)-5H-pyrrolo[3,2-d]pyrimidin-4-amine;
7-(5-(Azepan-1-yl)pentyl)-2-butyl-5H-pyrrolo[3,2-d]pyrimidin-4-amine;
7-(4-(Azepan-1-yl)butyl)-2-butyl-6-methyl-5H-pyrrolo[3,2-d]pyrimidin-4-amine;
2-Butyl-6-methyl-7-(6-(pyrrolidin-1-yl)hexyl)-5H-pyrrolo[3,2-d]pyrimidin-4-amine;
7-(6-(Azetidin-1-yl)hexyl)-2-butyl-6-methyl-5H-pyrrolo[3,2-d]pyrimidin-4-amine;
2-Butyl-6-methyl-7-(5-(pyrrolidin-1-yl)pentyl)-5H-pyrrolo[3,2-d]pyrimidin-4-amine;
7-(5-(Azetidin-1-yl)pentyl)-2-butyl-5H-pyrrolo[3,2-d]pyrimidin-4-amine;
7-(5-(Azetidin-1-yl)pentyl)-2-butyl-6-methyl-5H-pyrrolo[3,2-d]pyrimidin-4-amine;
2-Butyl-6-methyl-7-(4-(pyrrolidin-1-yl)butyl)-5H-pyrrolo[3,2-d]pyrimidin-4-amine;
2-Butyl-7-(5-(4,4-difluoropiperidin-1-yl)pentyl)-5H-pyrrolo[3,2-d]pyrimidin-4-amine;
2-Butyl-7-(5-(4-fluoropiperidin-1-yl)pentyl)-5H-pyrrolo[3,2-d]pyrimidin-4-amine;
7-(5-(4-Fluoropiperidin-1-yl)pentyl)-2-(2-methoxyethyl)-5H-pyrrolo[3,2-d]pyrimidin-4-amine;
1-(5-(4-Amino-2-butyl-5H-pyrrolo[3,2-d]pyrimidin-7-yl)pentyl)piperidin-4-ol;
(R)-2-Butyl-7-(5-(3-fluoropyrrolidin-1-yl)pentyl)-5H-pyrrolo[3,2-d]pyrimidin-4-amine;
(S)-2-Butyl-7-(5-(3-fluoropyrrolidin-1-yl)pentyl)-5H-pyrrolo[3,2-d]pyrimidin-4-amine;
(R)-7-(5-(3-Fluoropyrrolidin-1-yl)pentyl)-2-(2-methoxyethyl)-5H-pyrrolo[3,2-d]pyrimidin-4-amine;
(S)-7-(5-(3-Fluoropyrrolidin-1-yl)pentyl)-2-(2-methoxyethyl)-5H-pyrrolo[3,2-d]pyrimidin-4-amine;
(S)-1-(5-(4-Amino-2-butyl-5H-pyrrolo[3,2-d]pyrimidin-7-yl)pentyl)pyrrolidin-3-ol;
1-(5-(4-Amino-2-butyl-5H-pyrrolo[3,2-d]pyrimidin-7-yl)pentyl)azetidin-3-ol;
7-(6-(Azepan-1-yl)hexyl)-2-(2-methoxyethyl)-5H-pyrrolo[3,2-d]pyrimidin-4-amine;
2-Butyl-7-(6-(4-fluoropiperidin-1-yl)hexyl)-5H-pyrrolo[3,2-d]pyrimidin-4-amine;
(R)-2-Butyl-7-(6-(3-fluoropyrrolidin-1-yl)hexyl)-5H-pyrrolo[3,2-d]pyrimidin-4-amine;
(S)-2-Butyl-7-(6-(3-fluoropyrrolidin-1-yl)hexyl)-5H-pyrrolo[3,2-d]pyrimidin-4-amine;
(S)-2-Butyl-7-(5-(2-methylpyrrolidin-1-yl)pentyl)-5H-pyrrolo[3,2-d]pyrimidin-4-amine;
(R)-2-Butyl-7-(5-(2-methylpyrrolidin-1-yl)pentyl)-5H-pyrrolo[3,2-d]pyrimidin-4-amine;
2-Butyl-7-(5-(3-methylazetidin-1-yl)pentyl)-5H-pyrrolo[3,2-d]pyrimidin-4-amine;
2-Butyl-7-(5-(3-fluoroazetidin-1-yl)pentyl)-5H-pyrrolo[3,2-d]pyrimidin-4-amine;
2-Butyl-6-methyl-7-(6-(pyrrolidin-1-yl)hexyl)-5H-pyrrolo[3,2-d]pyrimidin-4-amine;
2-Butyl-7-(5-(4-fluoropiperidin-1-yl)pentyl)-6-methyl-5H-pyrrolo[3,2-d]pyrimidin-4-amine;
(S)-2-Butyl-7-(5-(3-fluoropyrrolidin-1-yl)pentyl)-6-methyl-5H-pyrrolo[3,2-d]pyrimidin-4-amine;
(R)-2-Butyl-7-(5-(3-fluoropyrrolidin-1-yl)pentyl)-6-methyl-5H-pyrrolo[3,2-d]pyrimidin-4-amine;
2-Butyl-7-(5-(3-fluoroazetidin-1-yl)pentyl)-6-methyl-5H-pyrrolo[3,2-d]pyrimidin-4-amine; and
2-(2-Methoxyethyl)-7-(5-(pyrrolidin-1-yl)pentyl)-5H-pyrrolo[3,2-d]pyrimidin-4-amine.

13. The compound according to claim 1 which is in the form of a pharmaceutically acceptable salt.

14. The compound according to claim 1 which is in the form of a free base.

15. A pharmaceutical composition comprising a compound as defined in claim 1, or a pharmaceutically acceptable salt thereof, and one or more pharmaceutically acceptable excipients.

16. A method of treatment of allergic rhinitis, which method comprises administering to a human subject in need thereof, a therapeutically effective amount of a compound as defined in claim 1, or a pharmaceutically acceptable salt thereof.

17. A method of treatment of asthma, which method comprises administering to a human subject in need thereof, a therapeutically effective amount of a compound as defined in claim 1, or a pharmaceutically acceptable salt thereof.

18. A compound according to claim 1, or a pharmaceutically acceptable salt thereof, which is 2-butyl-7-(5-(pyrrolidin-1-yl)pentyl)-5H-pyrrolo[3,2-d]pyrimidin-4-amine:

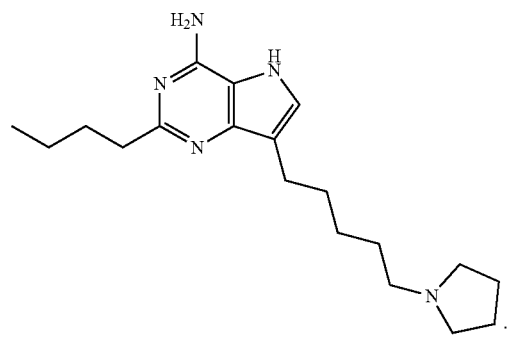 [SMILES: CCCCc1nc(N)c2[nH]cc(CCCCCN3CCCC3)c2n1]

* * * * *